US008623614B2

(12) United States Patent
Schüler et al.

(10) Patent No.: US 8,623,614 B2
(45) Date of Patent: Jan. 7, 2014

(54) METHOD FOR THE RECOMBINANT PRODUCTION OF MAGNETIC NANOPARTICLES

(75) Inventors: Dirk Schüler, München (DE); André Scheffel, Berlin (DE)

(73) Assignees: Ludwig-Maximilians-Univeristat, Munich (DE); Max-Planck-Gesellschaft zur Forderung der Wissenschaften e.V., Munich (DE)

( * ) Notice: Subject to any disclaimer, the term of this patent is extended or adjusted under 35 U.S.C. 154(b) by 619 days.

(21) Appl. No.: 12/682,510

(22) PCT Filed: Oct. 9, 2008

(86) PCT No.: PCT/EP2008/063551
§ 371 (c)(1),
(2), (4) Date: Jul. 30, 2010

(87) PCT Pub. No.: WO2009/047301
PCT Pub. Date: Apr. 16, 2009

(65) Prior Publication Data
US 2010/0292495 A1      Nov. 18, 2010

(30) Foreign Application Priority Data

Oct. 11, 2007  (EP) .................................... 07019965

(51) Int. Cl.
*C12N 15/00*      (2006.01)
(52) U.S. Cl.
USPC .......................................... 435/69.1; 977/773
(58) Field of Classification Search
None
See application file for complete search history.

(56) References Cited

U.S. PATENT DOCUMENTS

| 4,385,119 A | 5/1983 | Blakemore |
| 6,251,365 B1 | 6/2001 | Báuerlein et al. |

FOREIGN PATENT DOCUMENTS

WO    WO 2006/119102 A    11/2006

OTHER PUBLICATIONS

Prozorov et al., "Protein-mediated synthesis of uniform superparamagnetic magnetite nanocrystals", Adv. Funct. Mater. 17:951-957 (2007).*
Bazylinski, D.A. & Frankel, R.B., "Magnetosome Formation in Prokaryotes," *Nature Rev. Microbiol.*, 2:217-230, Nature Publishing Group, United States (2004).
Grünberg, et al., "Biochemical and Proteomic Analysis of the Magnetosome Membrane in *Magnetospirillum gryphiswaldense*," *Appl. Environ. Microbiol.*, 70:1040-1050, American Chemical Society, United States (2004).
Hergt, P., et al., "Magnetic properties of bacterial magnetosomes as potential diagnostic and therapeutic tools," *J. Magn. Magn. Mater.*, 293:80-86, Elsevier B.V., Holland (2005).
Heyen, U. & Schüler, D., "Growth and magnetosome formation by microaerophilic *Magnetospirillum* strains in an oxygen-controlled fermentor," *Appl. Micriobiol. Biotechnol.*, 61:536-544, Springer-Verlag, Germany (2003).
Hoell, A., et al., "Nanostructure and field-induced arrangement of magnetosomes studied by SANSPOL," *Physica. B.*, 350:e309-e313, Elsevier B.V., Holland (2004).
Jana, N.R., et al., "Size- and Shape-Controlled Magnetic (Cr, Mn, Fe, Co, Ni) Oxide Nanocrystals via a Simple and General Approach," *Chem. Mater.*, 16:3931-3935, American Chemical Society, United States (2004).
Komeili, A., et al., "Magnetosome vesicles are present before magnetite formation, and MamA is required for their activation," *PNAS*, 101:3839-3844, The National Academy of Sciences of the USA, United States (2004).
Komeili, A., et al., "Magnetosomes Are Cell Membrane Invaginations Organized by the Actin-Like Protein MamK," *Science*, 311:242-245, American Association for the Advancement of Science, United States (2006).
Lu, A-H, et al., "Magnetic Nanoparticles: Synthesis, Protection, Functionalization, and Application," *Angew. Chem. Int. Ed.*, 46:1222-1244, Wiley-VCH Verlag GmbH & Co. KGaA, Weinheim (2007).
Park, J., et al., "Ultra-large-scale syntheses of monodisperse nanocrystals," *Nature Materials*p. 1-5, Advance Online Publication, United States (2004).
Richter, M., et al., "Comparative Genome Analysis of Four Magnetotactic Bacteria Reveals a Complex Set of Group-Specific Genes Implicated in Magnetosome Biomineralization and Function," *J. Bacteriol.*, 189:4899-4910, American Society for Microbiology, United States (2007).
Scheffel, A., et al., "An acidic protein aligns magnetosomes along a filamentous structure in magnetotactic bacteria," *Nature*, 440:110-114, Nature Publishing Group, United States (2006).

(Continued)

*Primary Examiner* — Anand Desai
(74) *Attorney, Agent, or Firm* — Sterne, Kessler, Goldstein & Fox P.L.L.C.

(57) ABSTRACT

The present invention relates to methods and compositions for the size-adjusted recombinant production of magnetic nanoparticles. More particular, the invention relates to a method, comprising: providing one or more cells being capable of producing magnetic nanoparticles; modifying in the one or more cells the expression of one or more genes involved in the formation of the magnetic nanoparticles; cultivating the modified cells obtained in step (b); and isolating the magnetic nanoparticles from the cultivated cells, wherein the magnetic nanoparticles have a defined size. In preferred embodiments, the method comprises modifying the expression of one or more genes of the mamGFDC operon in magnetotactic bacterial cells. The invention is further directed to host cells bearing said modifications, the recombinant magnetic particles isolated from such cells as well as to the use of such particles for the detection and/or separation of biomolecules or as a contrast agent in magnetic resonance imaging.

11 Claims, 8 Drawing Sheets

(56) References Cited

OTHER PUBLICATIONS

Schultheiss, D. & Schüler, D., "Development of a genetic system for *Magnetospirillum gryphiswaldense*," *Arch. Microbiol.*, 179:89-94, Springer-Verlag, Germany (2003).

Taoka, A., et al., "Spatial Localizations of Mam22 and Mam12 in the Magnetosomes of *Magnetospirillum magnetotacticum*," *J. Bacteriol.*, 188:3805-3812, American Society for Microbiology, United States (2006).

Ullrich, S., et al., "A Hypervariable 130-Kilobase Genomic Region of *Magnetospirillum gryphiswaldense* Comprises a Magnetosome Island Which Undergoes Frequent Rearrangements during Stationary Growth," *J. Bacteriol.*, 187:7176-7184, American Society for Microbiology, United States (2005).

Lang, C., et al., "Synthesis of magnetite nanoparticles for bio- and nanotechnology: genetic engineering and biomimetics of bacterial magnetosomes," *Macromol. Biosci.* 7(2):144-151, Wiley, Germany (2007).

\* cited by examiner

METHOD FOR THE RECOMBINANT PRODUCTION OF MAGNETIC NANOPARTICLES

This application is the U.S. National Stage of International Application No. PCT/EP2008/063551, filed Oct. 9, 2008, which claims the benefit of European Patent Application No. 07019965.8, filed Oct. 11, 2007, both of which are incorporated herein by reference in their entirety.

REFERENCE TO A SEQUENCE LISTING SUBMITTED ELECTRONICALLY VIA EFS-WEB

The content of the electronically submitted sequence listing (Name: Sequence Listing.txt, Size: 85,400 bytes; and Date of Creation: Apr. 8, 2010) is herein incorporated by reference in its entirety.

FIELD OF THE INVENTION

The present invention relates to methods and compositions for the size-adjusted recombinant production of magnetic nanoparticles, particularly of nanoparticles derived of magnetotactic bacteria.

BACKGROUND

Magnetic nanoparticles typically comprise nanocrystals made of oxides (or to a lesser extent of sulfides) of the elements in the forth row of the periodic table (i.e. Cr, Mn, Fe, Co, and Ni). The ability to produce such magnetic nanoparticles is inevitable not only for the general understanding of magnetic properties in a nanometer regime but also for manifold technical applications ranging from magnetic resonance imaging, drug delivery, catalysts, and biosensing to nanoelectronics, semiconductor materials, and magnetic storage media (reviewed in Lu, A. et al. (2007) *Angew. Chem. Int. Ed.* 46, 1222-1224). Importantly, the magnetic properties of these nanocrystals strongly depend on their dimensions, that is, on their size and shape. For example, larger nanocrystals having a size of >35 nm in diameter have a permanent single magnetic domain (i.e. they are ferromagnetic), whereas smaller particles of <25 nm in diameter exhibit superparamagnetic properties (i.e. they are not permanently magnetic at ambient temperature). In previous years, research has thus mainly focused on the production of "size-adjusted" magnetic nanoparticles having "tailored" magnetic and physicochemical properties.

Traditionally, magnetic nanoparticles are synthesized chemically through precipitation of the crystals from basic aqueous solutions. However, the production of particularly dimensioned nanocrystals via these synthesis routes is significantly hampered by the broad size distribution of the crystal populations obtained. More recently, the synthesis of nanocrystals has been directed to non-aqueous approaches generally resulting in the formation of crystals having not only an improved overall quality but also a narrower size distribution. Nevertheless, in most chemical syntheses reported so far only sub-gram to low gram quantities of monodisperse nanocrystals were obtained, not sufficient for many applications. Furthermore, only a fraction of such synthetic particles constitutes monocrystalline particles having defined magnetic properties. By varying the experimental conditions employed the size of the particles could be controlled to some extent. However, the typical maximal diameters of the resulting particles were only in the range of about 25 nm, which is too small for clinically relevant applications such as magneto-hyperthermic treatment of tumors (Jana, N. R. et al. (2004) *Chem. Mater.* 16, 3931-3935; Park, J. et al. (2004) *Nature Materials* 3, 891-895; Hergt, R. et al. (2005) *J. Magnetism Magnetic Materials* 293, 80-86).

Alternatively, biogenic magnetic nanoparticles can be employed that are produced by magnetotactic organisms, predominantly magnetotactic bacteria. The ability of magnetotactic bacteria to orient in the Earth's magnetic field is based on the presence of specific organelles, the magnetosomes, which are membrane-enveloped monocrystalline crystals (i.e. crystals having a single magnetic domain) of a magnetic mineral that are arranged in chain-like structures within the cell. Magnetosomes display a variety of species-specific shapes within the single magnetic domain size range (reviewed in Bazylinski, D. A. and Frankel, R. B. (2004) *Nature Rev. Microbiol.* 2, 217-230). In the prototypical *Magnetospirillum*, cubo-octahedral nanocrystals of the mineral magnetite ($Fe_3O_4$) having a maximal diameter of 50 nm are synthesized within magnetosome membrane (MM) vesicles. The MM is a phospholipid bilayer of a distinctive biochemical composition. Different methods for both the cultivation of magnetotactic bacteria and the isolation of magnetosomes thereof are well established in the art (U.S. Pat. Nos. 4,385,119 and 6,251,365; Heyen, U. and Schüler, D. (2003) *Appl. Microbial. Biotechnol.* 61, 536-544).

In *Magnetospirillum (M.) gryphiswaldense* approximately 20 magneto some membrane proteins (MMPs) were identified so far, which are supposed to be involved in magnetosome biomineralization. However, the individual functions of MMPs have remained largely unknown, and only few magnetosome proteins are currently characterized in greater detail. Based on the data available magnetosome formation appears a highly complex process with strict control over MM-vesicle differentiation and formation, iron transport as well as nucleation, growth, and assembly of the magnetite crystals into chain-like structures. In order to function effectively in magnetic orientation, crystal sizes have to be controlled precisely within the single magnetic domain range, as the magnetic properties of magnetic nanocrystals change drastically with the particle's dimensions (see above). In previous studies, it was shown that decreasing the iron concentration in the growth medium or an increase in oxygen pressure resulted in the formation of smaller magnetite nanocrystals than under normal growth conditions. However, changing such environmental parameters does not allow for a reliable and accurate control of crystal size and shape. Rather recently, the isolation of spontaneous *M. gryphiswaldense* mutants producing smaller and aberrantly-shaped particles than wild-type cells (Hoell, A. et al. (2004) *Phys. B.* 350, e309-e313; Ullrich, S. et al. (2005) *J. Bacterial.* 187, 7176-7184) indicated that crystal dimensions are under genetic control as well. However, it is currently unknown how this regulation is achieved at the molecular level, and least of all what are the genetic factors the control of whose expression would enable the synthesis of "size-adjusted" magnetosomes.

Thus, there still remains a need for methods for producing magnetic nanoparticles that overcome the above-mentioned limitations. In particular, there is a need for methods enabling the reliable controlled production of monocrystalline particles having a (pre-determined) defined size suitable for a given application not only in high quantities but also in an easy-to-do and cost-efficient manner not requiring any sophisticated instrumentation and/or specific reactants.

Furthermore, there is also a need for corresponding monocrystalline magnetic nanoparticles having a defined size and thus displaying specific magnetic and/or physicochemical properties. In particular, there is a need for "customized" magnetic nanoparticles whose size and shape are specifically adapted for a particular use.

Accordingly, it is an object of the present invention to provide such "size-adjusted" magnetic nanoparticles as well as methods for their production.

These goals are accomplished by the recombinant magnetic nanoparticles and the method for producing the same as defined in the present invention.

SUMMARY OF THE INVENTION

In a first aspect, the present invention relates to a method for the recombinant production of magnetic nanoparticles, comprising: providing one or more cells being capable of producing magnetic nanoparticles; modifying in the one or more cells the expression of one or more genes involved in the formation of the magnetic nanoparticles; cultivating the modified cells obtained; and isolating the magnetic nanoparticles from the cultivated cells, wherein the magnetic nanoparticles have a defined size. In preferred embodiments, the "size-adjustment" of the magnetic nanoparticles produced results from of the modification of gene expression performed in the one or more target cells, that is, the size of the magnetic nanoparticles varies depending on the type and/or the extent of said modification.

Typically, the size of the recombinant magnetic nanoparticles produced is 20 nm to 150 nm in diameter. In some embodiments, the size of the nanoparticles is 25 nm to 50 nm in diameter. In other specific embodiments, the size of the nanoparticles is >50 nm in diameter. In other embodiments, the size of at least 50%, preferably of at least 80%, of the magnetic nanoparticles produced is within the range given by the mean diameter±10%.

Preferably, the recombinant magnetic nanoparticles produced by the method of the invention are monocrystalline (monocrystals), particularly preferably magnetite monocrystals. In other preferred embodiments, the magnetic nanoparticles further comprise a phospholipid outer membrane.

In other embodiments, the one or more cells provided are magnetotactic bacterial cells, preferably derived of *Magnetospirillum* spec.

In further preferred embodiments of the inventive method, the one or more genes involved in the formation of the magnetic nanoparticles (i.e. whose expression is to be modified) are selected from the group consisting of the mamG, mamF, mamD, and mamC genes of *M. gryphiswaldense* and functional equivalents thereof.

In specific embodiments, modifying the expression of the one or more genes involved in the formation of the magnetic nanoparticles comprises deleting in the one or more cells one or more of said genes. The one or more genes that are deleted in said cells are preferably selected from the group consisting of the mamG, mamF, mamD, and mamC genes of *Magnetospirillum gryphiswaldense* and functional equivalents thereof.

In other specific embodiments of the invention, modifying the expression of the one or more genes comprises introducing into the one or more cells a nucleic acid molecule comprising a nucleotide sequence encoding one or more copies of any one or more genes involved in the formation of the magnetic nanoparticles (also referred to as "genetic construct"). The one or more copies of the any one or more genes encoded by the nucleotide sequence may be operably linked to each other. Furthermore, the nucleotide sequence comprised in the nucleic acid molecule may be operably linked to a regulatory sequence in order to allow expression of the nucleotide sequence. Typically, the regulatory sequence comprises a promoter sequence and a transcription termination sequence. In some embodiments, the nucleic acid molecule encoding the nucleic acid sequence is comprised in a vector. In specific embodiments, the nucleic acid molecule may become stably integrated into the genome of the one or more cells in which it is introduced.

In preferred embodiments of the method, the one or more genes comprised in the nucleotide sequence to be introduced in the one or more cells provided are selected from the group consisting of the mamG, mamF, mamD, and mamC genes of *M. gryphiswaldense* and functional equivalents thereof.

Particularly preferred, the nucleotide sequence encodes a genetic construct selected from the group consisting of the mamG, mamF, mamD, mamC, mamGF, mamGD, mamGC, mamFD, mamFC mamDC, mamGFD, mamGFC, mamGDC, mamFDC, and mamGFDC, genes of *M. gryphiswaldense* and functional equivalents thereof. Preferably, the nucleotide sequence encodes a genetic construct selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, and SEQ ID NO: 14.

In a second aspect, the invention relates to a host cell comprising a nucleic acid molecule comprising a nucleotide sequence encoding a genetic construct of one or more copies of any of the one or more genes involved in the formation of the magnetic nanoparticles. In particular, the host cell may be a magnetotactic bacterial cell, preferably derived of *Magnetospirillum* spec.

In a third aspect, the invention relates to a recombinantly produced magnetic nanoparticle having a defined size of 20 nm to 150 nm in diameter as defined herein. In specific embodiments, the size of the magnetic nanoparticles is >50 nm in diameter.

The magnetic nanoparticle may be a monocrystal (monocrystalline), preferably a magnetite monocrystal. In some embodiments, the magnetic nanoparticles may further comprise a phospholipid outer membrane. In preferred embodiments, the magnetic nanoparticle is derived of a magnetotactic bacterial cell, in particular of *Magnetospirillum* spec.

In further preferred embodiments, the magnetic nanoparticle is produced by a method according to the present invention.

In a forth aspect, the invention relates to the use of said recombinant magnetic nanoparticles as an analytical tool for the detection and/or separation of biomolecules or as a contrast agent in magnetic resonance imaging.

DESCRIPTION OF THE DRAWINGS

FIG. 3 depicts the phenotypic analysis of ΔmamC and ΔmamGFDC mutant strains.

The inserts show (I) a magnification of a prevalent magnetosome chain, (II) the prevalent crystal shapes and (III) the purified magnetosomes which were negatively stained with uranylacetate. Arrowheads indicate magnetosome membrane junctions between isolated crystals.

DETAILED DESCRIPTION OF THE INVENTION

Figure 1:
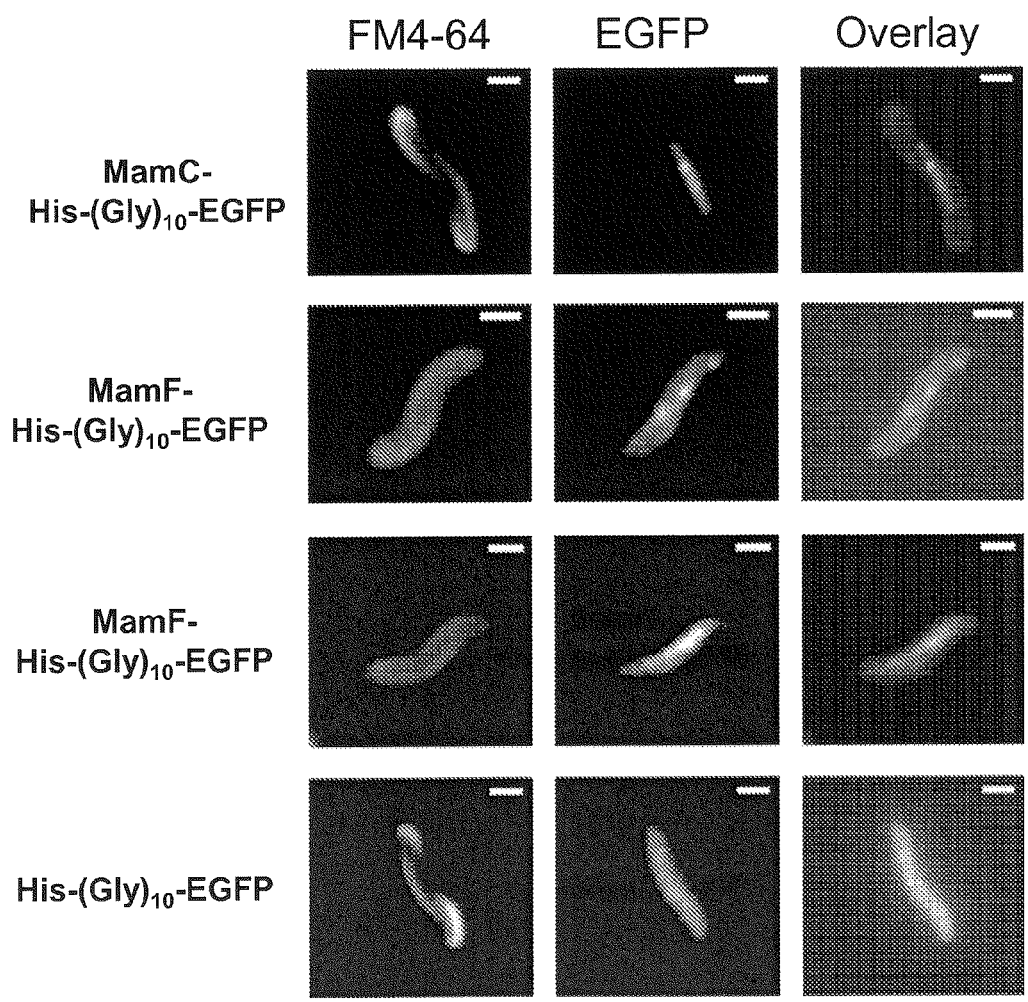
FIG. 1 depicts fluorescence micrographs showing the in viva localization of MamC-, MamF-, and MamG-EGFP fusion proteins in *Magnetospirillum gryphiswaldense*. The fluorescence signals of the fusion proteins localize at midcell in a linear pattern. As a control, the localization of His-(Gly)$_{10}$-EGFP is shown. Cell membranes were stained with the dye FM4-64. The length of the scale bar is 0.5 µm.

The present invention is based on the unexpected finding that neither the deletion of the mamC gene encoding the most abundant magnetosome protein in *Magnetospirillum* (*M.*) *gryphiswaldense* nor the deletion of the entire mamGFDC operon (collectively encoding nearly 35% of all proteins associated with the magneto some membrane) did abolish magnetite biomineralization in this organism. Rather, cells lacking the mamGFDC operon produced magnetite crystals having only 75% of the wild-type size. However, the formation of wild-type-sized magnetite crystals could be gradually restored by the in trans complementation with one, two, or three genes of the mamGFDC operon, respectively, regardless of their combination, whereas the expression of all four genes resulted in crystals even exceeding wild-type size.

In a first aspect, the present invention relates to a method for the recombinant production of magnetic nanoparticles, comprising:
(a) providing one or more cells being capable of producing magnetic nanoparticles;
(b) modifying in the one or more cells the expression of one or more genes involved in the formation of the magnetic nanoparticles;
(c) cultivating the modified cells obtained in step (b); and
(d) isolating the magnetic nanoparticles from the cultivated cells,
wherein the magnetic nanoparticles have a defined size.

The term "magnetic nanoparticles", as used herein, denotes any particle having a size in the nanometer scale that exhibits magnetic properties (i.e. that orients in a magnetic field along the magnetic field lines). The particles may either be ferromagnetic or superparamagnetic or may show an intermediate characteristic. The term "nanometer scale", as used herein, refers to a particle diameter of less than 1000 nm (i.e. 1 μm), preferably of less than 500 nm, and particular preferably of less than 200 nm.

More particularly, the term "magnetic nanoparticles" refers to particles comprising one or more magnetic (nano) crystals. In preferred embodiments, a magnetic particle according to the invention comprises only a single nanocrystal. Such particles are also referred to as being "monocrystalline" or "monocrystals".

Typical nanocrystals comprised in the magnetic particles used in the invention are made of one or more metal oxides and/or metal sulfides, preferably of the elements in the forth row of the periodic table (i.e. chrome, manganese, iron, cobalt, and nickel). In some embodiments, the magnetic nanocrystals are made of a single metal oxide or a single metal sulfide, preferably of an iron oxide such as magnetite ($Fe_3O_4$) or an iron sulfide such as greigite ($Fe_3S_4$), with magnetite being particular preferred.

In other preferred embodiments, the magnetic nanoparticles further comprise an outer membrane surrounding the one or more nanocrystals. Within the scope of the present invention, such particles are also referred to as "magnetosomes", particularly when used in connection with magnetotactic bacteria.

Typically, the outer membrane of the magnetic nanoparticles described herein is a lipid bilayer membrane, preferably a phospholipid membrane that may comprise any combination of one or more naturally occurring or synthetic phospholipids such as phosphatidyl glycerole, phosphatidyl ethanolamine, and phosphatidyl choline. The phospholipids may contain one or more fatty acids such as palmitic acid, palmitoleic acid, and oleic acid. In preferred embodiments, the phospholipid membranes comprise 35-40% (w/w) phosphatidyl glycerole, 50-55% (w/w) phosphatidyl ethanolamine, and 5-10% (w/w) phosphatidyl choline, with palmitic acid (15-20% (w/w)), palmitoleic acid (25-30% (w/w)), and oleic acid (45-50% (w/w)) being the main fatty acids present. Exemplary membrane compositions are also disclosed, e.g., in Grünberg, K. et al. (2004) *Appl. Environ. Microbiol.* 70, 1040-1050.

The terms "recombinant" and "recombinant production", as used herein, refer to the fact that the magnetic nanoparticles according to the invention are not chemically synthesized but generated by means of recombinant gene technology well established in the art (see, e.g., Sambrook, J., and Russel, D. W. (2001) *Molecular cloning: A laboratory manual* (3rd ed.). Cold Spring Harbor, N.Y.: Cold Spring Harbor Laboratory Press). In other words, the magnetic nanoparticles of the invention are produced in host cells whose genome (i.e. the entirety of the cell's genetic information) comprises at least one modification compared to wild-type cells. Examples for such modifications include the insertion, deletion and/or substitution of one or more nucleotides within the host cell's genome (i.e. the chromosome(s) and any additional episomal genetic entities such as plasmids or phagemids), the introduction of additional copies of one or more genes into the host cell as well as, optionally, their stable integration into the genome, and the insertion or deletion of genetic elements (e.g., promoters, repressors, enhancers but also miRNAs, siRNAs, anti-sense RNAs, and the like) interfering with or promoting the expression of one or more host genes at transcriptional, post-transcriptional or translational level.

The recombinant magnetic nanoparticles according to the present invention are characterized by a defined (i.e. predetermined) size and thus by particular magnetic and physicochemical properties which are known to vary as a function of particle size. The term "production of magnetic nanoparticles having a defined size", as used herein, is to be understood that the method for producing said particles is precisely controlled in order to enable the generation of specifically dimensioned particles that are, for example, ideally adapted for an intended application. In the present invention, precise control of the conditions is accomplished by modifying in the one or more target cells provided the expression of one or more genes involved in the formation of the magnetic nanoparticles. In preferred embodiments, the size of the magnetic nanoparticles produced varies directly depending on the type and/or the extent of the modification of gene expression performed (see below).

The terms "size" and "dimension", as used herein, are not solely to be interpreted literally (i.e. with regard to the length and width of the magnetic nanoparticles) but should also refer to the overall shape of the particles such as spherical or cubic, regular or deformed, and the like. Preferably, the size of the magnetic nanoparticles is expressed as the mean diameter of the particles, expressed in nm, resulting from the analysis of at least two, typically of at least ten, preferably of at least 20, and particularly preferably of at least 50 individual nanoparticles.

In specific embodiments, the size of the magnetic nanoparticles according to the invention is 20 nm to 150 nm in diameter. However, it may also be possible to produce smaller and larger particles as well. In preferred embodiments, the size of the magnetic nanoparticles produced is 25 nm to 50 nm in diameter, for example particles having a size of 25-30 nm, 30-35 nm, 35-40 nm, 40-45 nm or 45-50 nm. In other preferred embodiments, the size of the magnetic nanoparticles is >50 nm in diameter, for example at least 52 nm, at least 55 nm, at least 60 nm, at least 65 nm or at least 70 nm.

Since the method according to the present invention involves the use of genetically engineered target cells as a source for producing the magnetic nanoparticles, the size distribution of the particles may not be entirely uniform due to the genetic and/or physiological variations inherent to cellular populations. Rather, the size of the particles produced in a single assay may differ slightly within given limits depending on the reaction conditions used. In specific embodiments of the invention, the size of at least 50%, preferably of at least 80%, and particularly preferably of at least 90% of the magnetic nanoparticles produced (in a single assay) is within the range given by the mean diameter±15%, preferably by the mean diameter±10%, and particularly preferably by the mean diameter±5%.

The term "providing one or more cells being capable of producing magnetic nanoparticles", as used herein, is to be understood to denote that the method according to the present invention requires the presence of particular host cells (herein also referred to as "target cells"), namely cells having the "genetic competence" to synthesize magnetic nanoparticles (i.e. bear in their genome the respective genes required for the formation of magnetosome).

In specific embodiments of the invention, the one or more cells provided are magnetotactic bacterial cells. The term "magnetotactic bacterial cells", as used herein, refers to any prokaryotic cells displaying a magnetotactic response, that is, they orient in a magnetic field along the magnetic field lines. Preferably, the one or more magnetotactic cells are derived (i.e. are members) of the genus *Magnetosprillum* such as *M. magneticum, M. magnetotacticum*, and *M. gryphiswaldense*, with the latter one being particularly preferred. Further examples of suitable magnetotactic bacteria include inter cilia the magnetotactic proteobacteria MV-1 and MC-1.

The term "one or more genes involved in the formation of the magnetic nanoparticles", as used herein, denotes any genes associated with the magnetotactic phenotype, that is, any genes coding for proteins participating in magneto some synthesis such as proteins regulating the formation of the membrane envelope or nanocrystal biomineralization. Preferably, the one or more genes encode magnetosome membrane proteins (MMPs) which associate with the magnetosome membrane and are supposed to be involved in the control of biomineralization. In particular preferred embodiments of the invention, the one or more genes are selected from the group consisting of the mamG, mamF, mamD, and mamC genes of *M. gryphiswaldense* (cf. *M. gryphiswaldense* MSR-1, Working Draft Sequence, GenBank Accession Number: CU459003) and functional equivalents thereof.

The term "functional equivalent", as used herein, denotes any other gene than the four above-mentioned mam genes of *M. gryphiswaldense* that encodes a protein having the same presumed cellular function as any of MamG, MamF, MamD, and MamC of *M. gryphiswaldense* (i.e. an ortholog). Typically, such orthologs share a high degree of amino acid sequence similarity. Within the scope of the present invention, functional equivalent genes are understood to encode proteins having at least 30% or at least 40%, preferably at least 50% or at least 80%, and particularly preferably at least 90% amino acid sequence identity with any of MamG, MamF, MamD, and MamC of *M. gryphiswaldense*, as determined using the NCBI/BLAST program according to the default standard parameters (http://www.ncbi.nlm.nih.gov/BLAST/bl2seq/wblast2.cgi; Tatusova, T. and Madden, T. L. (1999) *FEMS Microbiol Lett.* 174, 247-250). An example of such a functional equivalent gene, as defined herein, is the mmsF gene of *M. gryphiswaldense* MSR-1 encoding another MMP (Richter, M. et al. (2007) *J. Bacteriol.* 189, 4899-4910).

The term "modifying in the one or more cells the expression of one or more genes involved in the formation of magnetic nanoparticles", as used herein, refers to the fact that the one or more host or target cells used in the invention for synthesizing the magnetic nanoparticles bear in their genome at least one change as compared to wild-type cells resulting in a modified expression of any one or more genes involved in the synthesis of said particles such as genes encoding protein factors regulating the formation of the membrane envelope and/or nanocrystal biomineralization.

The term "modifying gene expression", as used herein, denotes any manipulation of a particular gene (or more than one genes) resulting in an altered expression level of said gene (or said genes), that is, the production of a different amount of corresponding mRNA and/or protein as compared to the expression of the wild-type gene (or genes). The term "different amount", as used herein, includes both a higher amount and a lower amount than wild-type. In other words, a manipulation, as defined herein, may either enhance (i.e. activate) or repress (i.e. inhibit) the expression of a gene. The term "repression", as used herein, includes abolishing the expression a gene (for example, by deleting the gene sequence). It is also within the scope of the present invention that a particular modification of gene expression affects a plurality of genes in a different manner. For example, it may be possible that such modification activates the expression of a first gene and concomitantly inhibits the expression of a second gene.

The term "genome", as used herein" denotes the entirety of genetic information comprised in a host cell, that is, the chromosome(s) (which in bacteria is also referred to as the "lineom") and any additional episomal genetic entities propagated in the host cells such as plasmids, cosmids, phagemids, artificial chromosomes, or the like. It is within the scope of the present invention that the one or more (host) cells provided comprise one or more genes involved in the formation of magnetic nanoparticles, whose expression is modified, wherein all said genes are encoded on the chromosome(s) or wherein all said genes are encoded on one or more episomal entities, or wherein at least one gene is encoded on the chromosom(s) and at least one gene is encoded on an episomal entity.

Examples for such modifications affecting the expression of the one or more genes involved in the formation of magnetic nanoparticles, as defined herein, include inter alia the insertion, deletion and/or substitution of one or more nucleotides within the host cell's genome, the introduction of additional copies of one or more genes into the host cell as well as, optionally, their stable integration into the genome, and the introduction or deletion of genetic elements (e.g., promoters, repressors, enhancers but also miRNAs, siRNAs, anti-sense RNAs, and the like) interfering with or promoting the expression of one or more host genes at transcriptional, post-transcriptional or translational level. The term "insertion, deletion or substitution of one or more nucleotides", as used herein, is to be understood that at least one nucleotide of a particular gene sequence whose expression is to be modified is altered by insertion, deletion and/or substitution, optionally giving rise to an change of the corresponding amino acid sequence as well. It is also within the scope of the present invention to alter the nucleotide sequence of regulatory elements controlling the expression of one or more genes involved in the formation of magnetic nanoparticles. Examples for such elements include inter alia promoters, transcriptional enhancers, repressors, and the like). Many genes involved in the formation of magnetic nanoparticles, particularly most MMPs, are arranged in polycistronic operon (herein also referred to as "operable linkage", see below), that is, at least two genes (typically encoding functionally related proteins) are located adjacent to each other and are under the control of common transcriptional and/or translational regulatory elements such as a common promoter sequence. An example of such an operon is the mamGFDC operon of *M. gryphiswaldense*. Thus, it is also within the scope of the present invention, to modify the expression of such an operon, for example, by insertion, deletion and/or substitution of one or more nucleotides (including the insertion, deletion and/or substitution of one or more entire genes).

In specific embodiments of the inventive method, modifying the expression of the one or more genes involved in the formation of the magnetic nanoparticles comprises deleting in the one or more cells provided one or more of such genes. Preferably, the one or more genes that are deleted are selected from the group consisting of the mamG, mamF, mamD, and mamC genes of *Magnetospirillum gryphiswaldense* and functional equivalents thereof. It is within the scope of the present invention to delete only a single gene, for example mamC (herein said deletion is also denoted "ΔmamC"), to delete any combination of two or three genes, for example mamFC (i.e. a deletion of both mamF and mamC), or to delete the entire mamGFDC operon. As used herein, the term "deletion" not only refers to the removal of an entire gene but also to the removal of a portion thereof sufficient to modify (e.g., to abolish) gene expression in order to render the encoded corresponding protein non-functional.

In further specific embodiments, modifying the expression of the one or more genes comprises introducing into the one or more cells provided a nucleic acid molecule (preferably a DNA molecule) comprising a nucleotide sequence encoding a genetic construct of one or more copies of any of the one or more genes involved in the formation of the magnetic nanoparticles. Thus, for example, it is also within the scope of the present invention to introduce a nucleic acid molecule as defined above in addition to deleting in the one or more cells one or more genes involved in the formation of the magnetic nanoparticles. Moreover, it is also within the scope of the present invention to introduce into the one or more cells provided two or more nucleic acid molecules, each comprising a nucleotide sequence encoding a genetic construct of one or more copies of any of the one or more genes involved in the formation of the magnetic nanoparticles.

In particular embodiments, the one or more copies of any of the one or more genes encoded by the nucleotide sequence to be introduced in the one or more cells provided are operably linked to each other (i.e. they are arranged as a single "functional" unit, optionally under the control of common transcriptional and/or translational regulatory elements). In further embodiments, the nucleotide sequence to be introduced in the one or more cells provided is operably linked to a regulatory sequence in order to allow expression of the nucleotide sequence.

A nucleic acid molecule is referred to as "capable of expressing a nucleic acid molecule" or capable "to allow expression of a nucleotide sequence" if it comprises sequence elements which contain information regarding to transcriptional and/or translational regulation, and such sequences are "operably linked" to the nucleotide sequence encoding the polypeptide. An operable linkage is a linkage in which the regulatory sequence elements and the sequence to be expressed (and/or the sequences to be expressed among each other) are connected in a way that enables gene expression. The precise nature of the regulatory regions necessary for gene expression may vary among species, but in general these regions comprise a promoter which, in prokaryotes, contains both the promoter per se, i.e. DNA elements directing the initiation of transcription, as well as DNA elements which, when transcribed into RNA, will signal the initiation of translation. Such promoter regions normally include 5' non-coding sequences involved in initiation of transcription and translation, such as the −35/−10 boxes and the Shine-Dalgarno element in prokaryotes or the TATA box, CAAT sequences, and 5'-capping elements in eukaryotes. These regions can also include enhancer or repressor elements as well as translated signal and leader sequences for targeting the native polypeptide to a specific compartment of a host cell.

In addition, the 3' non-coding sequences may contain regulatory elements involved in transcriptional termination, polyadenylation or the like. If, however, these termination sequences are not satisfactory functional in a particular host cell, then they may be substituted with signals functional in that cell.

Therefore, a nucleic acid molecule of the invention to be introduced into the one or more cells provided may include a regulatory sequence, preferably a promoter sequence, and optionally also a transcriptional termination sequence. The promoters may allow for either a constitutive or an inducible gene expression. Suitable prokaryotic promoters are, for example, the *E. coli* lacUV5 and tet (tetracycline-responsive) promoters, the T7 promoter as well as any promoters derived of magnetotactic bacteria, preferably of *Magnetosprillum* spec. Particularly preferred examples include inter alia the mamGFDC promoter and the mamAB promoter of *M. gryphiswaldense*. Examples of promoters useful for expression in eukaryotic cells are the SV40 promoter or the CMV promoter.

The nucleic acid molecules of the invention may also be comprised in a vector or other cloning vehicles, such as plasmids, phagemids, phages, cosmids or artificial chromosomes. In a preferred embodiment, the nucleic acid molecule is comprised in a vector, particularly in an expression vector. Such an expression vector can include, aside from the regulatory sequences described above and a nucleic acid sequence encoding a genetic construct as defined in the invention, replication and control sequences derived from a species compatible with the host that is used for expression as well as selection markers conferring a selectable phenotype on transformed or transfected cells. Large numbers of suitable vectors are known in the art, and are commercially available.

In specific embodiments of the inventive method, the one or more genes comprised in the nucleotide sequence to be introduced into the one or more cells to be provided are selected from the group consisting of the mamG, mamF, mamD, and mamC genes of *M. gryphiswaldense* and functional equivalents thereof.

In preferred embodiments, the nucleotide sequence encodes a genetic construct selected from the group consisting of the mamG, mamF, mamD, mamC, mamGF, mamGD, mamGC, mamFD, mamFC mamDC, mamGFD, mamGFC, mamGDC, mamFDC, and mamGFDC, genes of *Magnetospirillum gryphiswaldense* and functional equivalents thereof. Preferably, the nucleotide sequence encodes a genetic construct selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, and SEQ ID NO: 14.

Within the scope of the present invention, the nucleic acid molecule introduced may be propagated and maintained as an independent genetic unit or it may become stably integrated into the genome of the one or more cells by means of genetic recombination. Such recombination may either occur at random positions of the genome by non-homologous recombination or at specific positions of the genome by homologous recombination or via site-specific integrases.

The nucleic acid molecule encoding a genetic construct of one or more copies of any of the one or more genes involved in the formation of the magnetic nanoparticles, particularly when comprised in a vector, can be introduced via various transformation, transduction or transformation methods all well known in the art (see, e.g., Sambrook, J., and Russel, D. W. (2001), supra) into a host (target) cell capable of expressing the nucleic acid molecule. Thus, the present invention is also directed to a host cell comprising a nucleic acid molecule as disclosed herein.

Host cells to be used in the invention may be any prokaryotic (i.e. bacterial or archeal) or eukaryotic cells being capable of producing magnetic nanoparticles. In preferred embodiments, the host cell is a magnetotactic bacterial cell, preferably members of the genus *Magnetospirillum*, with *M. gryphiswaldense* being particularly preferred.

After having modified the expression of one or more genes involved in the formation of magnetic nanoparticles the host cells disclosed herein are cultivated (propagated) under conditions allowing the formation magnetic nanoparticles which will clearly vary depending on the nature of the host cell employed. However, the skilled artisan is well aware of the growth conditions to be used in a particular case. Finally, the magnetic nanoparticles produced can be isolated from the host cells simply due to their magnetic behavior by applying a magnet to the host cell culture. Different methods for both the cultivation of magnetotactic bacteria and the isolation of magnetosomes thereof are well established in the art (U.S. Pat. Nos. 4,385,119 and 6,251,365; Heyen, U. and Schüler, D. (2003) *Appl. Microbial. Biotechnol.* 61, 536-544). The isolation of the magnetic particles from the host cells may comprise additional processing steps such as a selection of particular fractions of particles based on their magnetic properties, for example by applying to the particles magnetic fields of different field strengths.

In a further aspect, the invention relates to recombinantly produced magnetic nanoparticles having a defined size of 20 nm to 150 nm in diameter, that is, engineered, particularly dimensioned particles generated by means of recombinant gene technology as defined herein (see above). For example, the particles may have a size of 25-30 nm, 30-35 nm, 35-40 nm, 40-45 nm or 45-50 nm in diameter. In specific embodiments, the size of the particles is >50 nm in diameter, for example at least 52 nm, at least 55 nm, at least 60 nm, at least 65 nm or at least 70 nm. Preferably, the magnetic nanoparticle is monocrystalline (i.e. comprises only a single crystal). In some embodiments, the monocrystal consists of magnetite.

In other preferred embodiments, the magnetic nanoparticle further comprises a phospholipid outer membrane and/or is derived of a magnetotactic bacterial cell, preferably of *Magnetospirillum* spec.

In further preferred embodiments, the magnetic nanoparticles are produced by a method as disclosed herein.

In a forth aspect, the present invention relates to uses of the recombinant magnetic nanoparticles disclosed herein. Specific embodiments of the invention relate to the use of such a magnetic nanoparticle as an analytical tool for the detection and/or separation of biomolecules. For example, it may be possible to generate "functionalized" nanoparticles being coated with particular binding domains having affinity for biomolecule and thus allow their isolations. The term "coated", as used herein, also includes the modification of the membrane envelope surrounding the magnetic nanocrystals. Examples for such binding domains include inter alia oligo-dT stretches having affinity for poly(A)$^+$ RNAs, avidin or streptavidin allowing the binding of biotinylated molecules but also specific binding domains such as antibodies or antibody-like molecules enabling detection and binding of particular antigens. Thus, magnetic nanoparticles of the invention may also be used as a drug carrier for targeting pharmaceuticals to particular cells or organs within an organism.

In other embodiments, magnetic nanoparticles as defined herein are used as a contrast agent in magnetic resonance imaging. Further clinically relevant applications of the inventive nanoparticles include inter alia the magneto-hyperthermic treatment of cancerogenic tissues.

Other applications for using magnetic nanoparticles according to the invention are described, e.g., in Lu, A. et al. (2007), supra; and Lang, C. and Schüler, D. (2006) In: *Microbial Bionanotechnology: Biological Self-assembly Systems and Biopolymer-based Nanostructures*. B. Rehm (ed). Wymondham: Horizon Bioscience, pp. 107-124.

The invention is further described by the figures and the following examples, which are solely for the purpose of illustrating specific embodiments of this invention, and are not to be construed as limiting the scope of the invention in any way.

EXAMPLES

Example 1

Generation of ΔmamGFDC and ΔmamC Mutant Strains 1.1. Bacterial Strains, Media and Growth Conditions Liquid cultures of *Magnetospirillum* (*M.*) *gryphiswaldense* strain R3/S1 (Schultheiss, D. and Schüler, D. (2003) *Arch. Microbial.* 179, 89-94) were grown in modified FSM medium (Heyen, U. and Schüler, D. (2003) *Appl. Microbiol. Biotechnol.* 61, 536-544). Colonies of *M. gryphiswaldense* were obtained on activated charcoal agar medium (ACAM) that was incubated micro-aerobically at 28° C. (Schultheiss, D. and Schüler, D., 2003, supra). Growth experiments were carried out under micro-oxidic conditions in 1-1 flasks containing 100 ml low- or high iron containing medium. Low-iron containing medium (LIM) essentially is FSM medium lacking yeast extract and ferric citrate, whereas for high-iron medium ferric citrate was added to 500 µM to LIM. To grow magnetite free cells (no magnetic response), *M. gryphiswaldense* strains were passaged for three successive transfers in LIM. Optical densities and the magnetic response (Cmag) of *M. gryphiswaldense* cultures were measured turbidimetrically at 565 nm on immotile cells inactivated by addition of formaldehyde (Fluka, Switzerland) to a final concentration of 0.074% prior the measurement (Schüler, D. et al. (1995) *FEMS Microbiol. Lett.* 132, 139-145). Magnetosomes were isolated as described previously (Grünberg, K. et al. (2004) *Appl. Environ. Microbiol.* 70, 1040-1050) from cultures grown under micro-oxidic conditions. For conjugation experiments, *Escherichia coli* strain S17-1 (Simon, R. et al. (1983) *Biotechnology* 1, 784-791) was used as a donor and was cultivated as previously described (Sambrook, J., and Russel, D. W. (2001) *Molecular cloning: A laboratory manual* (3rd ed.). Cold Spring Harbor, N.Y.: Cold Spring Harbor Laboratory Press).

1.2. DNA Techniques

DNA isolation, digestion, ligation and transformation essentially followed standard methods (Sambrook, J. and Russel, D. W. (2001), supra). The primers and plasmids used are listed in the following Tables 1 and 2. PCR products and vector inserts were sequenced using BigDye Terminator v3.1 chemistry (Applied Biosystems, Darmstadt, Germany) on an ABI 3700 capillary sequencer. Sequence data were analyzed with Lasergene 6 (DNAstar Inc., Madison, Wis.) and MacVector 7.0 (Oxford Molecular Ltd., Oxford, United Kingdom) programs.

TABLE 1

Primers used in this study

| Name | Sequence (5'-3') |
|---|---|
| G/EcoRI-for | GATATCTTAAGCGAGGGCAAAGCAAT |
| G/PstI_rev | CTGCAGCATCTGATCTCCGGCAAGTGTA |
| C/PstI_for | CTGCAGGCCTGAAATATTGGGCTGGTTCAC |
| C/XbaI_rev | TCTAGAGTTGATGGGGGCGCGGAAGTTTC |
| AGmamCu_f/MunI | CAATTGATCTATTCTCAACTTTTTCGC |
| AGmamCu_r/NdeI-2 | CATATGCATCGCTGTTGTCCTTAATTCAA |
| AGmamCd_f/ApaI | GGGCCCGCCTGAAATATTGGGCTGGTTCAC |
| AGmamCd_r/SacI | GAGCTCGCTTCACCGTCGTCTCGCCG |

TABLE 1-continued

Primers used in this study

| Name | Sequence (5'-3') |
|---|---|
| a | CTCGAGCCCCAGGGGGGCAAACCATT |
| b | AAGGGCATCGCGGCGTTGGC |
| b* | CGCCAACGCGGCGATGCCCTTG |
| c | CAGGCTGAGGCCAGCGGTGAGCCTGCTTAA |
| c* | TTAAGCAGGCTCAGCGCTGGCCTCAGCCTG |
| d | ATCGAAACTAAAACAGCTGGCGGC |
| d* | GCCGCCAGCTGTTTTAGTTTCGAT |
| e | TCTGCCCCTTATAAGCCATGTAGTC |
| e* | GACTACATGGCTTATAAGGGGCAGA |
| f | CTTTTTCTCGGAAGGTCGAA |
| f* | TTCGACCTTCGCGAGAAAAAG |
| g | GGAACCGGTCAGCTTGTCATGATG |
| g* | CATCATGACAAGCTGACCGGTTCC |
| h | GGCGAGGAATAAGCCTGACCCTTGAATTCAGGACAACAG |
| h* | TTATTCCTCGCCGACAGCCGCCAGCAATGCATCATCGGAAAC |
| i | AGGAAGCCGCCGGTGCCGGGCTT |
| i* | AAGCCCGGCACCGGCGGCTTCCTTG |
| j | GCCCTAATCGCCGGTGTCGCCGC |
| j* | GCGGCGACACCGGCGATTAGGGC |
| k | GAGCTCGAATTCTCAGAGGCAGAGAGTGGGC |
| CL21 | CATATGGGAGGCGGAGGCGGTGGCGGAGGTGGCGGAGTGAGCAAGGGCGAGGAG |
| CL22 | GTGGATCCTTACTTGTACAGCTCGTC |
| CL23 | CTCGAGGGAGATCAGATGATCAAGGGCATC |
| CL24 | CATATGAGCAGGCTCGGCGGAGGC |
| CL9 | CTCGAGAGGGCAAAGCAATGGCCGAGAC |
| CL10 | CATATGGATCAGGGCGACTACATGGCTG |
| CL13 | CTCGAGAGGACAACAGCGATGAGCTTTC |
| CL14 | CATATGGGCCAATTCTTCCCTCAG |

Restriction sites are shown in italic and mismatch nucleotides in bold.

TABLE 2

Bacterial strains and plasmids used in this study

| Strain/Plasmid | Description | Reference |
|---|---|---|
| *M. gryph.* MSR-1 R3/S1 | Rifr, Smr spontaneous mutant | Schultheiss, D. et al. (2004) |
| *M. gryph.* ΔC::Kan | *M. gryph.* ΔmamC::Kan t | his study |
| *M. gryph.* ΔC | *M. gryph.* ΔmamC | this study |
| *M. gryph.* ΔC_C | ΔC(pAS35) | this study |
| *M. gryph.* ΔGFDC | *M. gryph.* ΔmamGFDC | this study |
| *M. gryph.* ΔGFDC_MCS2 | ΔGFDC(pBBR1MCS-2) | this study |
| *M. gryph.* ΔGFDC_GFDC | ΔGFDC(pAS31) | this study |

TABLE 2-continued

Bacterial strains and plasmids used in this study

| Strain/Plasmid | Description | Reference |
| --- | --- | --- |
| *M. gryph.* ΔGFDC_G | ΔGFDC(pAS32) | this study |
| *M. gryph.* ΔGFDC_F | ΔGFDC(pAS33) | this study |
| *M. gryph.* ΔGFDC_D | ΔGFDC(pAS34) | this study |
| *M. gryph.* ΔGFDC_C | ΔGFDC(pAS35) | this study |
| *M. gryph.* ΔGFDC_GD | ΔGFDC(pAS36) | this study |
| *M. gryph.* ΔGFDC_GC | ΔGFDC(pAS37) | this study |
| *M. gryph.* ΔGFDC_FD | ΔGFDC(pAS38) | this study |
| *M. gryph.* ΔGFDC_FC | ΔGFDC(pAS39) | this study |
| *M. gryph.* ΔGFDC_DC | ΔGFDC(pAS40) | this study |
| *M. gryph.* ΔGFDC_GFD | ΔGFDC(pAS41) | this study |
| *M. gryph.* ΔGFDC_GFC | ΔGFDC(pAS42) | this study |
| *M. gryph.* ΔGFDC_GDC | ΔGFDC(pAS43) | this study |
| *M. gryph.* ΔGFDC_FDC | ΔGFDC(pAS44) | this study |
| pBBR1MCS-2 | Kn$^r$, lacZα | Kovach, M. E. et a. (1995) |
| pK19mobsacB | Kn$^r$, sacB modif. from *B. subtilis*, lacZ | Schäfer, A. et al. (1994) |
| pCM184 | Ap$^r$; Kn$^r$ | Marx, C. J. et al. (2002) |
| pCM157 | Tc$^r$ | Marx, C. J. et al. (2002) |
| pEGFP-N1 | Ap$^r$; Egfp expression vector | Clontech, BD Biosciences |
| pDC2 | pK19mobsacB with mamGFDC cluster upstream and downstream flank | this study |
| pAG3 | pCM184 with mamC upstream flank between MunI/NdeI | this study |
| pAG4 | pAG3 with mamC downstream flank between ApaI/SacI | this study |
| pAS100 | pSP72 with 2.941 kb construct consisting of 2077 bp mamGFDC operon, 705 bp upstream and 159 bp downstream sequence between XhoI/SacI | this study |
| pAS101 | pAS100 cut with NaeI/Eco47III, self-ligated | this study |
| pAS102 | pAS100 cut with PvuII/PsiI, self-ligated | this study |
| pAS103 | pAS100 cut with NruI/BfrBI, blunted, self-ligated | this study |
| pAS104 | pAS100 cut with EcoRI, self-ligated | this study |
| pAS105 | pAS100 cut with NaeI/PsiI, self-ligated | this study |
| pAS106 | pAS100 cut with NaeI/BamHI, blunted, self-ligated | this study |
| pAS107 | pAS100 cut with PvuII/BamHI, blunted, self-ligated | this study |
| pAS109 | pAS105 cut with EcoRI, self-ligated, | this study |
| pAS110 | pAS100 cut with PvuII/EcoRI, blunted, self-ligated | this study |
| pAS111 | pAS101 cut with NruI/EcoRI, blunted, self-ligated | this study |
| pAS112 | pAS104 cut with PvuII/PsiI, self-ligated | this study |
| pAS113 | pAS104 cut with NaeI/Eco47III, self-ligated | this study |
| pAS114 | pAS101 cut with NruI/BamHI, blunted, self-ligated, | this study |
| pAS31 | pBBR1MCS-2 with 2941 bp XhoI-SacI fragment of pAS100, for mamGFDC expression | this study |
| pAS32 | pBBR1MCS-2 with 1014 bp XhoI-SacI fragment of pAS110, for mamG expression | this study |
| pAS33 | pBBR1MCS-2 with 1229 bp XhoI-SacI fragment of pAS111, for mamF expression | this study |
| pAS34 | pBBR1MCS-2 with 1826 bp XhoI-SacI fragment of pAS109, for mamD expression | this study |
| pAS35 | pBBR1MCS-2 with 1538 bp XhoI-SacI fragment of pAS106, for mamC expression | this study |
| pAS36 | pBBR1MCS-2 with 2104 bp XhoI-SacI fragment of pAS112, for mamGD expression | this study |
| pAS37 | pBBR1MCS-2 with 1819 bp XhoI-SacI fragment of pAS107, for mamGC expression | this study |
| pAS38 | pBBR1MCS-2 with 2165 bp XhoI-SacI fragment of pAS113, for mamFD expression | this study |
| pAS39 | pBBR1MCS-2 with 2038 bp XhoI-SacI fragment of pAS114, for mamFC expression | this study |
| pAS40 | pBBR1MCS-2 with 2375 bp XhoI-SacI fragment of pAS105, for mamDC expression | this study |
| pAS41 | pBBR1MCS-2 with 2401 kb XhoI-SacI fragment of pAS104, for mamGFD expression | this study |
| pAS42 | pBBR1MCS-2 with 2265 bp XhoI-SacI fragment of pAS103, for mamGFC expression | this study |
| pAS43 | pBBR1MCS-2 with 2668 kb XhoI-SacI fragment of pAS102, for mamGDC expression | this study |
| pAS44 | pBBR1MCS-2 with 2722 kb XhoI-SacI fragment of pAS101, for mamFDC expression | this study |
| pCL_EGFP | pBBR1MCS-2 with N-terminal modified egfp from pEGFP-N1, expresses His-(Gly)$_{10}$-EGFP | this study |
| pCL_C-EGFP | pBBR1MCS-2 with XhoI-NdeI mamC-egfp fusion, expresses MamC-His-(Gly)$_{10}$-EGFP | this study |
| pCL_F-EGFP | pBBR1MCS-2 with XhoI-NdeI mamF-egfp fusion, expresses MamF-His-(Gly)$_{10}$-EGFP | this study, |

TABLE 2-continued

Bacterial strains and plasmids used in this study

| Strain/Plasmid | Description | Reference |
|---|---|---|
| pCL_G-GFP | pBBR1MCS-2 with XhoI-NdeI mamG-egfp fusion expresses MamG-His-(Gly)$_{10}$-EGFP | this study, |

References:
Schultheiss, D. et al. (2004) *Appl. Environ. Microbiol.* 70, 3624-3631
Kovach, M. E. et al. (1995) *Gene* 166, 175-176
Schäfer, A. et al. (1994) *Gene* 145, 69-73
Marx, C. J., and Lidstrom, M. E. (2002) *BioTechniques* 33, 1062-1067

1.3. Construction of ΔmamGFDC and ΔmamC Mutant Strains

A *M. gryphiswaldense* mutant lacking the mamGFDC cluster was generated using plasmid pDC2. For construction of pDC2, 670 bp of the mamGFDC-upstream sequence including the ATG-start codon of mamG was amplified by primer pair G/EcoRI-for and G/PstI_rev and 810 bp of the mamGFDC-downstream sequence including TGA-stop codon of mamC by primer pair C/PstI-for and C/XbaI_rev, respectively. Both amplification products were fused in a three-fragment ligation between the EcoRI and XbaI sites of plasmid pK19mobsacB to obtain pDC2. Plasmid pDC2 was introduced into *M. gryphiswaldense* R3/S1 via conjugation from *E. coli* S-17 and clones having chromosomally integrated pDC2 were selected on kanamycin (Kan) containing ACAM medium. Since no double-crossovers mutants were obtained by sucrose selection due to instable sacB expression, 300 randomly selected colonies were replica-plated on ACAM medium (with and without Kan). Southern blotting on three clones that showed sensitivity to Kan confirmed deletion of the mamGFDC operon. One mutant clone, designated ΔGFDC, was selected for further studies.

For generating a mamC mutant, the broad-host-range Cre-loxP antibiotic marker recycling system was used (Marx, C. J., and Lidstrom, M. E. (2002) *BioTechniques* 33, 1062-1067) in order to test its usability in *M. gryphiswaldense*. Searches for lox sites (34 bp composed of a short core sequence between two inverted repeats) in the *M. gryphiswaldense* genome sequence identified no site identical to the characteristic lox sequence, which might have been targeted by the Cre recombinase. The Cre recombinase of bacteriophage P1 catalyzes the site specific recombination between lox sites and in particular the in vivo excision of DNA regions flanked by co-directional loxP recognition sites (Palmeros, B. et al., (2000) *Gene* 247, 255-264). Cre expression from plasmid pCM157 (Marx, C. J., and Lidstrom, M. E (2002), supra) in *M. gryphiswaldense* was verified by means of RT-PCR. Cells expressing Cre did not show any apparent change in growth or magnetosome biomineralization, suggesting that Cre does not catalyze recombination between sequence sites inherent to the chromosome of *M. gryphiswaldense*.

For the mamC deletion construct, the regions immediately flanking mamC were amplified via PCR using the following primer pairs: AGmamCu_f/MunI and AGmamCu_r/NdeI-2 for the upstream region as well as AGmamCDd_f/ApaI and AGmamCd_r/SacI for the downstream region. The 1822 bp mamC-upstream fragment was inserted between the MunI and NdeI sites of pCM184 (Marx, C. J., and Lidstrom, M. E (2002), supra), which is upstream of a loxP flanked Kan resistance marker to yield pAG3. Sequencing of the 1450 bp mamC-downstream fragment revealed 204 bp downstream of the 5' end an ApaI restriction site which is missing in the partial 35 kb sequence deposition (BX571797) of the magnetosome island used for primer construction. Subsequently, digestion of the 1450 bp mamC-downstream PCR product with ApaI and SacI yielded a 1246 bp fragment that was inserted downstream of the loxP flanked Kan resistance marker of ApaI/SacI digested pAG3, producing pAG4. Allelic exchange vector pAG4 was introduced into *M. gryphiswaldense* strain R3/S1 bp conjugation from *E. coli* S-17 and transconjugants were selected on solid ACAM-medium containing Kan. Kan-resistant transconjugants were found at frequency of 2.2·10$^{-6}$ per recipient cell. Several randomly selected clones were propagated for one passage in liquid medium and streaked out on solid medium without antibiotics. Colonies from those plates were screened by PCR for loss of mamC, which occurred at a frequency of 1.0·10$^{-1}$. For one clone, designated ΔC::Kan, replacement of mamC by a loxP flanked Kan resistance marker was confirmed by Southern blot analysis. For excision of the Kan marker gene from clone ΔC::Kan, plasmid pCM157 was introduced via conjugation from *E. coli* S-17, and transconjugants were selected on tetracycline. After one passage on solid medium with tetracycline, 96% of the tetracycline-resistant ΔC::Kan derived clones were Kan sensitive. For one clone designated ΔC loss of the Kan gene was confirmed by Southern blot analysis. Plasmid pCM157 was cured from ΔC by transfer to medium lacking tetracycline. Excision of the marker by Cre leaves behind a loxP-scar at the position of the mamC gene.

Example 2

In Vivo Localization of Mam Proteins 2.1. Construction of EGFP-Fusions for In Vivo Localization The EGFP protein was fused by a His-(Gly)$_{10}$ peptide linker to the C-terminus of MamG, MamF, and MamD, respectively. The egfp gene (primer CL21/CL22) was amplified from the pEGFP-N1 plasmid and cloned into the EcoRI site of the pBBR1MCS-2 to yield the plasmid pCL_EGFP expressing (Gly)$_{10}$-EGFP. The amplified genes of mamC (primer CL13/CL14), mamF (CL9/CL10), and mamG (CL23/CL24) were cloned into the XhoI and NdeI restriction sites of pCL_EGFP in order to generate plasmids pCL_C-EGFP (MamC-His-(Gly)$_{10}$-EGFP), pCL_F-EGFP (MamF-His-(Gly)$_{10}$-EGFP), and pCL_G-EGFP (MamG-His-(Gly)$_{10}$-EGFP), respectively. Despite various attempts and different and using different constructs no functional MamD-EGFP fusion could be generated. All plasmids were transferred into *M. gryphiswaldense* R3/S1 via conjugation from *E. coli* S17-1.

2.2. Fluorescence Microscopy

Cell membranes were stained with the fluorescent dye FM4-64 (Molecular Probes) at a final concentration of 1.5 µM. Cells were imaged with a Leica DMI 6000B microscope equipped with a DFC 350FX camera and a 100×HCX PL APO objective with a numerical aperture of 1.40. Pictures were captured and analyzed using a Leica Application Suite and ImageJ 1.36b software.

2.3. Specific Location of MamC, MamF, and MamG at the Magnetosome Membrane

The MamGFDC proteins were previously identified in the magnetosome sub-proteome, however, it was unknown if their presence is confined to the magnetosome membrane, or if they are shared by other subcellular compartments. To address this question, translational EGFP-fusions of MamC, MamF and MamG were constructed. While no functional EGFP fusion to the MamD protein was obtained, the MamC, MamG, and MamF fusion proteins generated a linear fluorescence pattern of 1-3 µm in length, and had a slightly punctuate appearance (FIG. 1). The fluorescence signal coincided with the typical position of the magnetosome chain predominantly at mid-cell and was mostly confined to the characteristic length of the magnetosome chain. No fluorescence signal was detected in either the cytoplasm or the cytoplasmic membrane, indicating that the MamG, MamF, and MamC proteins were exclusively targeted to the magnetosome compartment.

Example 3

Figure 2:
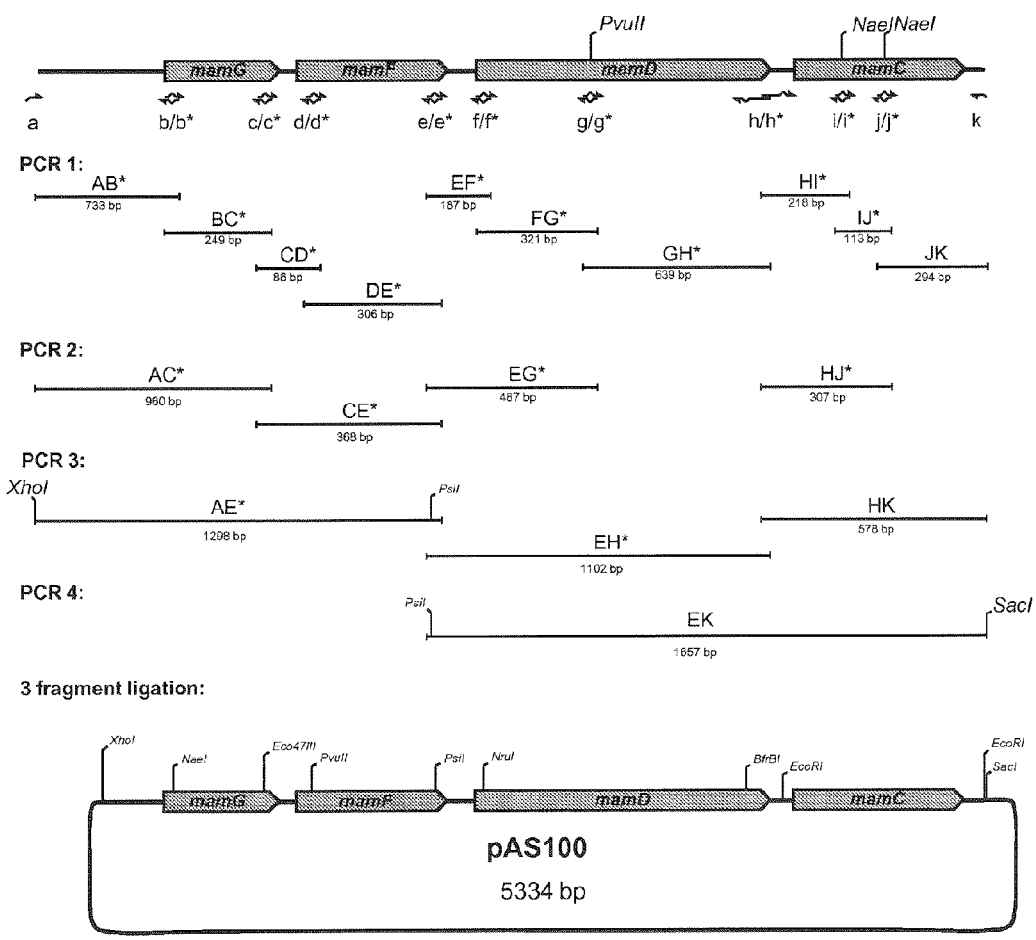
FIG. 2 illustrates the construction of engineered variants of mamGFDC cluster for the complementation studies.

Complementation Analyses, Effects on Crystal Size and Shape 3.1. Generation of Genetic Constructs For genetic complementation of the ΔC and the ΔGFDC mutant strains, a series of pBBR1MCS-2-based plasmids, harboring full-length (pAS31) or deletion-containing variants of the mamGFDC cluster (pAS32-pAS44), were generated. Sequence deletions within the recombinant mamGFDC cluster were generated in plasmid pAS100 by restriction digestion. Then, the mamGFDC cluster variants obtained were cloned between XhoI and SacI sites of pBBR1MCS-2 for expression in *M. gryphiswaldense*. Construction of plasmid pAS100, harboring a 2941 bp XhoI-SacI fragment consisting of a 705 bp mamGFDC upstream sequence, the mamGFDC cluster (2077 bp) containing silent mutations, and a 159 bp mamGFDC downstream sequence is illustrated in FIG. 2.

For constructing the 2941 bp fragment primer annealing to the 5' and the 3' sequence region of mamC (5' b/b*; 3' c/c*), mamF (5' d/d*; 3' e/e*), and mamD (5' f/f*; 3' h/h*), within mamD (g/g*), within mamC (i/i*; j/j*), upstream of the mamG start codon (a), and downstream of the mamC stop codon (k) were deduced from the magnetosome island sequence deposition BX571797. Primer annealing within the mamGFDC cluster contained mismatches to generate silent point mutations which either created or removed a restriction site: primer b/b* and c/c* created a NaeI and a Eco47III site within mamG, primer d/d* and e/e* a PvuII and a PsiI site within mamF, primer f/f* and h created a NruI and a BfrBI site within mamD, primer g/g* removed a PvuII site contained in mamD, primer h* created an EcoRI site 18 bp upstream of mamC, primer i/i* and j/j* removed NaeI sites contained in mamC. Assembly of the 2941 bp XhoI-SacI sequence fragment was accomplished via four rounds of PCR. The first round resulted in ten sequence fragments: AB* (primer pair a/b*), BC* (primer pair b/c*), CD* (primer pair c/d*), DE* (primer pair d/e*), EF* (primer pair e/f*), FG* (primer pair f/g*), GH* (primer pair g/h*), HI* (primer pair h/i*), IJ* (primer pair i/j*), JK (primer pair j/k). Next, the sequence fragments of the first PCR round were fused in three successive rounds of fusion PCR (Ho, S, N. et al. (1989) *Gene* 77, 51-59) until two sequence fragments remained (AE* and EK) which were ligated between XhoI and SacI digested pSP72 to produce pAS100.

Sequence deletions in modified variants of the mamGFDC cluster were created in pAS100 by parallel digestion with two restriction enzymes and subsequent re-ligation of the vector backbone. For instance, for excision of mamC, pAS100 was digested with EcoRI and recirculated producing pAS104, while for creating a large deletion with mamG pAS100 was digested with NaeI and Eco47111 producing pAS101. pBBR1MCS-2 based expression vectors containing single gene constructs were pAS32 (mamG), pAS33 (mamF), pAS34 (mamD), and pAS35 (mamC), vectors containing double gene constructs were pAS36 (mamGD), pAS37 (mamGC), pAS38 (mamFD), pAS39 (mamFC), and pAS40 (mamDC), and vectors containing triple gene constructs were pAS41 (mamGFD), pAS42 (mamGFC), pAS43 (mamGDC), and pAS44 (mamFDC). Vector pBBR1MCS-2 without insert was used as a negative control. Complementation constructs were introduced into the recipient mutant strains of *M. gryphiswaldense* by means of biparental conjugation with *E. coli* S17-1 as a donor. Expression of single, double and triple complementation constructs was verified by reverse transcription PCR, demonstrating that the deletions within the mamGFDC operon do not inhibit transcription of genes located downstream in the operon.

3.2. Electron Microscopy and Size Analysis of Membrane Vesicles and Magnetite Crystals Transmission electron microscopy was performed either on a Zeiss EM 10 on unstained cells adsorbed on carbon-coated copper grids, or on a Zeiss EM 912, equipped with an integrated OMEGA energy filter operated in the zero loss mode, on thin sections.

For thin sections, cells were fixed with 2.5% glutardialdehyde in 75 mM sodium cacodylate, 2 mM $MgCl_2$ (pH 7.0) for 1 h at room temperature. Post-fixation was performed for 1 h with 1% osmium tetroxide in a fixative buffer. Then, cells were stained en bloc with 1% uranyl acetate in 20% acetone for 30 min. Dehydration was performed with a graded acetone series. Samples were then infiltrated and embedded in "Spurr's" low-viscosity resin. Ultra thin sections were cut with a diamond knife and mounted on uncoated copper grids. The thin sections were post-stained with aqueous lead citrate (100 mM, pH 13.0).

For crystal analysis, *M. gryphiswaldense* cultures were grown at micro-oxidic conditions for 24 h at 28° C. Crystal parameters (crystal size and shape factor) were measured from digitized TEM micrographs using ImageJ 1.36b and the plugin Watersheds_514 developed by M. Pinchon and N. Bonnet, which allows the semi-automatic segmentation of particles from the images (http://helios.univ-reims.fr/Labos/INSERM514/ImageJ/). The twinned crystals which were occasionally observed (frequency of approximately 7%) were omitted from analysis because the segmentation algorithm often failed to detect the correct crystal edges. Mann-Whitney significance test (http://elegans.swmed.edu/~leon/stats/utest.html) was used to determine the significance of difference between crystal size and between shape factor distributions.

3.3. Loss of MamC has Only Minor Effects on Magnetite Crystal Formation

Figure 3A:
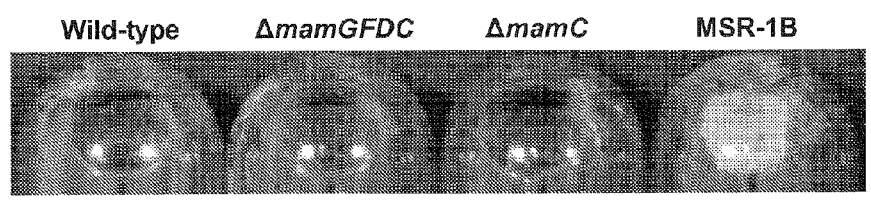
FIG. 3A shows the appearance of pellets of mutant and wild-type cells. For comparison a pellet of the magnetosome-free *M. gryphiswaldense* MSR-1B mutant is shown.
Figure 3B:
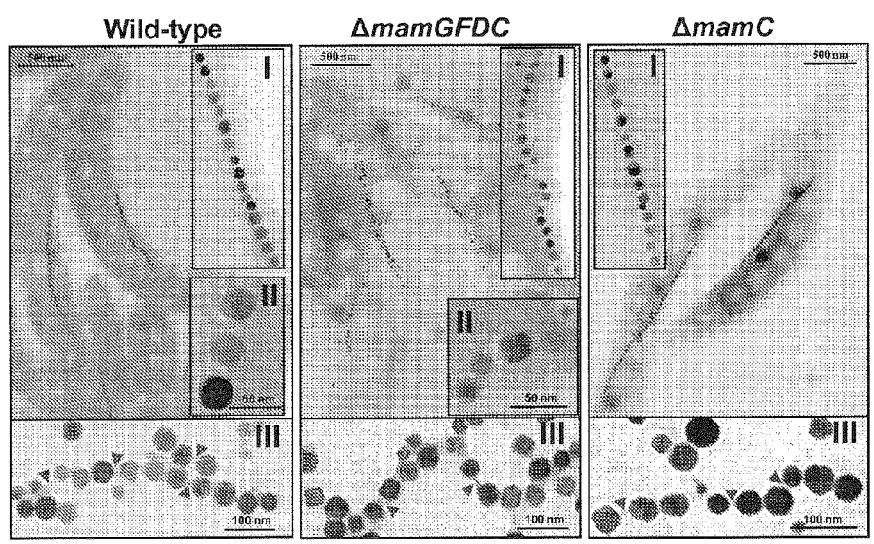
FIG. 3B illustrates transmission electron micrographs of wild-type, ΔmamC, and ΔmamGFDC cells.
Figure 3C:
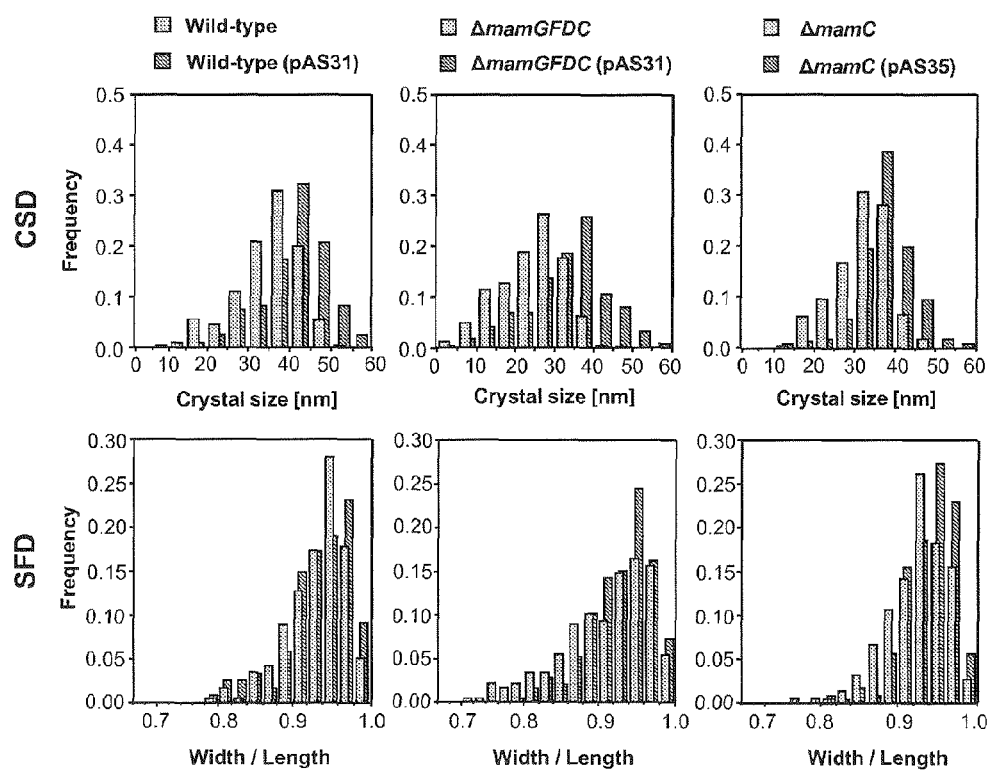
FIG. 3C depicts the crystal size and shape factor distributions for the wild-type, the mutant strains ΔmamC and ΔmamGFDC, and the complemented mutants.

Cells of the ΔmamC mutant exhibited a magnetic reaction both under the microscope and in the light scattering assay, and had a dark-brown appearance virtually identical to the wild-type (FIG. 3A). In electron micrographs, magnetosomes were found arranged in chains having sizes and shapes very similar to those of the wild-type (FIG. 3B). However, size measurements of 225 magnetosome particles from ΔmamC mutant cells revealed that mature magnetite crystals were on average slightly smaller compared to those of the wild-type (FIG. 3C, Tables 3 and 4). Complementation of the mutant strain by pAS35 restored the formation of magnetosome sizes close to the wild-type range.

population. In contrast, crystals of 35-40 nm in size were most abundant in the wild-type, thus crystals>30 nm occurred at a significantly higher frequency of 77.5%. Maximum sizes of crystals without obvious crystal defects, such as twinning, were 41.5 nm in mutant cells, and 50.1 nm for the wild-type. In addition, mutant crystals showed more often anisotropic

TABLE 3

Statistical parameters of crystal size and shape factor distributions (CSD and SFD) of magnetite crystals from wild-type and mutant strains of M. gryphiswaldense

| Strain | inter-crystal Space (nm) | No. of Crystals | CSD Maximum (nm) | CSD Mean (nm) | CSD Median (nm) | SFD Maximum (nm) | SFD Maximum | SFD Mean |
|---|---|---|---|---|---|---|---|---|
| Wild-type | 53 ± 5 | 236 | 35-40 | 34.8 | 36.2 | 50.4 | 0.94-0.96 | 0.932 |
| ΔGFDC | n.d. | 235 | 25-30 | 24.1 | 25.3 | 41.5 | 0.94-0.96 | 0.908 |
| ΔGFDC_GFDC | 51 ± 6.5 | 245 | 35-40 | 33.7 | 34.8 | 57.8 | 0.94-0.96 | 0.929 |
| ΔGFDC_MCS2 | n.d. | 139 | 25-30 | 28.1 | 28.4 | 42.0 | 0.94-0.96 | 0.922 |
| ΔGFDC_G | n.d. | 169 | 30-35 | 30.6 | 31.7 | 42.7 | 0.92-0.94 | 0.914 |
| ΔGFDC_F | n.d. | 160 | 30-35 | 31.3 | 31.4 | 46.4 | 0.92-0.94 | 0.917 |
| ΔGFDC_D | n.d. | 179 | 30-35 | 32.6 | 33.1 | 42.7 | 0.94-0.96 | 0.922 |
| ΔGFDC_C | n.d. | 230 | 30-35 | 33.3 | 33.1 | 47.7 | 0.94-0.96 | 0.921 |
| ΔGFDC_GD | n.d. | 110 | 30-35 | 30.3 | 30.9 | 45.1 | 0.94-0.96 | 0.920 |
| ΔGFDC_GC | n.d. | 187 | 30-35 | 31.8 | 32.3 | 45.2 | 0.92-0.94 | 0.921 |
| ΔGFDC_FD | n.d. | 199 | 35-40 | 35.5 | 36.9 | 54.9 | 0.94-0.96 | 0.932 |
| ΔGFDC_FC | n.d. | 177 | 30-35 | 31.3 | 32.6 | 43.4 | 0.92-0.94 | 0.917 |
| ΔGFDC_DC | n.d. | 184 | 35-40 | 32.9 | 33.5 | 44.3 | 0.94-0.96 | 0.933 |
| ΔGFDC_GFD | n.d. | 141 | 30-35 | 31.0 | 32.8 | 55.1 | 0.96-0.98 | 0.921 |
| ΔGFDC_GFC | n.d. | 204 | 35-40 | 34.7 | 35.5 | 51.4 | 0.94-0.96 | 0.929 |
| ΔGFDC_GDC | n.d | 182 | 35-40 | 33.0 | 34.5 | 46.3 | 0.90-0.92 | 0.917 |
| ΔGFDC_FDC | n.d | 143 | 35-40 | 34.9 | 35.5 | 49.6 | 0.94-0.96 | 0.921 |
| ΔC::Kan | 51 ± 8.5 | 225 | 30-35 | 31.9 | 33.4 | 49.1 | 0.92-0.94 | 0.925 |
| ΔC_C | 54 ± 4.5 | 230 | 35-40 | 37.5 | 37.8 | 56.0 | 0.94-0.96 | 0.939 |

Analysis of solubilized magnetosome membrane proteins (MMPs) from the mutant by SDS-PAGE and Western blotting revealed the absence of the highly abundant 12.4 kDa MamC band from the resolved polypeptide pattern, which was otherwise virtually unchanged compared to the wild-type (data not shown). In electron micrographs, isolated magnetosome particles from the mutant appeared identical to wild-type magnetosomes with respect to the presence of an organic membrane layer, the inter-particle spacing, and their tendency to rearrange in chains (FIG. 3B) suggesting that the absence of MamC did not markedly affect the formation of a functional magnetosome membrane.

3.4. ΔmamGFDC Mutant Strain Produces Magnetosome Crystals Having Only 75% of the Wild-Type Size The unexpected finding that loss of the most abundant magnetosome protein MamC had only a minor effect on magnetosome formation prompted the generation of a deletion mutant lacking the entire mamGFDC operon, which was designated strain ΔGFDC.

Cells of ΔGFDC exhibited a magnetic response if checked by microscopic observation. However, in contrast to the dark brown wild-type and ΔmamC mutant, colonies of strain AGFDC only had a slightly brownish color (FIG. 3A). TEM micrographs of mutant cells revealed the presence of small magnetosome crystals that frequently had a cuboidal shape, and were aligned in irregular, widely spaced chains (FIG. 3B, Table 3). Analysis of more than 220 crystals confirmed that the mutant crystal size distribution (CSD) is shifted towards smaller sizes (the Mann-Whitney probability value determined for CSD of wild-type and of ΔGFDC crystals is P=2.77E-8, indicating that the difference is statistically significant). For the mutant, crystals of 25-30 nm in size occurred at highest frequency, whereas crystals>30 nm were of low abundance, accounting for only 24.3% in the analyzed shapes (shape factor, SF) as only 37.4% of the crystals analyzed were equidimensional (SF>0.94), whereas 50.8% of the wild-type crystals had a SF>0.94.

Complementation of strain AGFDC with plasmid pAS31 harboring the entire mamGFDC cluster increased the size of mature magnetite crystals to wild-type size range. CSD and SF distributions of wild-type and complemented mutant strain were almost similar (P>1E-01), which substantiates that the effects on the AGFDC magnetosome crystals result from loss of the MamGFDC proteins (FIG. 3C, Tables 3 and 4).

TABLE 4

Results of the Mann-Whitney significance test for CSD and SFD of magnetite crystals from wild-type and mutant strains of M. gryphiswaldense

| Strain | CSD Wild-type | CSD ΔGFDC | SFD Wild-type | SFD ΔGFDC |
|---|---|---|---|---|
| Wild-type | | 2.77E-38* | | 2.54E-06* |
| ΔGFDC | 2.77E-38* | | 2.54E-06* | |
| ΔGFDC_GFDC | 2.11E-01 | 2.55E-27* | 4.17E-01 | 9.89E-04* |
| ΔGFDC_MCS2 | 1.19E-17* | 4.80E-06* | 6.22E-02 | 1.28E-01 |
| ΔGFDC_G | 3.87E-10* | 7.60E-17* | 4.16E-04* | 6.04E-01 |
| ΔGFDC_F | 2.52E-07* | 9.71E-18* | 1.75E-03 | 3.75E-01 |
| ΔGFDC_D | 4.32E-06* | 2.26E-28* | 2.97E-02 | 7.69E-02 |
| ΔGFDC_C | 1.21E-03 | 5.48E-34* | 1.02E-03 | 1.92E-01 |
| ΔGFDC_GD | 3.81E-08* | 4.81E-11* | 5.04E-02 | 1.70E-01 |
| ΔGFDC_GC | 1.64E-08* | 1.61E-24* | 1.87E-03 | 2.03E-01 |
| ΔGFDC_FD | 4.56E-01 | 1.42E-37* | 6.31E-01 | 4.34E-04* |
| ΔGFDC_FC | 4.29E-08* | 3.90E-20* | 1.41E-03 | 3.62E-01 |
| ΔGFDC_DC | 1.36E-04* | 2.75E-29* | 6.71E-01 | 8.40E-05* |
| ΔGFDC_GFD | 3.82E-06* | 1.57E-12* | 1.72E-02 | 1.83E-01 |
| ΔGFDC_GFC | 4.20E-01 | 1.44E-37* | 4.04E-01 | 1.58E-03 |
| ΔGFDC_GDC | 1.87E-03 | 2.62E-27* | 8.80E-05* | 6.26E-01 |
| ΔGFDC_FDC | 7.00E-01 | 5.00E-30* | 1.01E-02 | 1.83E-01 |

TABLE 4-continued

Results of the Mann-Whitney significance test for CSD and SFD of magnetite crystals from wild-type and mutant strains of *M. gryphiswaldense*

| Strain | CSD Wild-type | ΔGFDC | SFD Wild-type | ΔGFDC |
|---|---|---|---|---|
| ΔC::Kan | 6.12E−07* | 5.24E−25* | 1.95E−02 | 3.70E−02 |
| ΔC_C | 5.76E−04* | 2.35E−06* | 8.12E−02 | 2.31E−06* |

*Mann-Whitney probability test is statistically highly significant (P < 1E−03).

Figure 4:
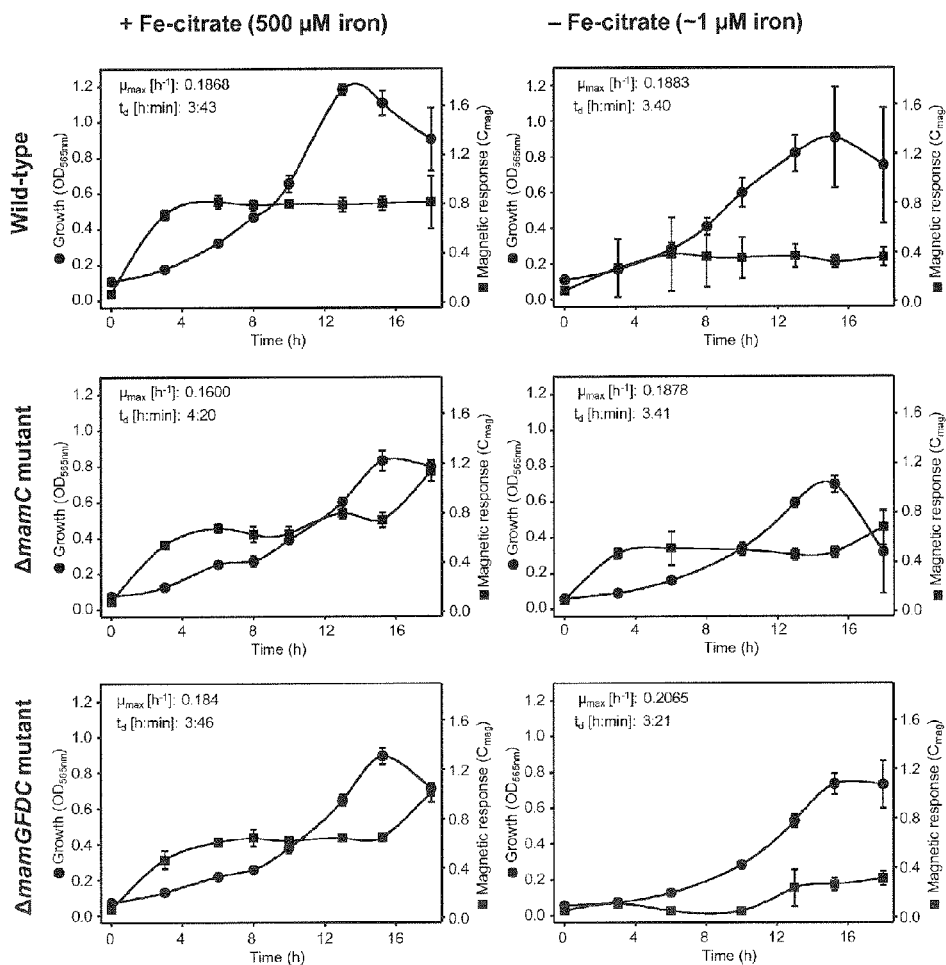
FIG. 4 depicts the growth rates and the magnetic responses of wild-type as well as the ΔmamC and ΔmamGFDC mutants under high and low iron conditions.

3.5 The Formation of Small Magnetosomes Cannot be Compensated by an Increased Iron Concentration One possible reason for the formation of smaller, growth-inhibited crystals could be a reduced flux of iron from the exterior into the magnetosome vesicles. Therefore, growth rates and magnetosome formation of the wild-type and the ΔmamC and the ΔmamGFDC mutant were compared at low (~1 μM) and high iron (~500 μM) concentrations (FIG. 4).

The formation of small magnetosomes could not be compensated by increased iron, as indicated by TEM and $C_{mag}$ measurements. Almost identical doubling times (3 h 40 min) were determined for the wild-type under both conditions, for ΔGFDC at 500 μM Fe, and for the ΔmamC mutant under low iron conditions, respectively. Even though strain ΔGFDC grew slightly faster at low iron, and growth of the ΔmamC mutant was slightly slower at 500 μM Fe, no substantial effect on growth caused by the deletion of mamC or mamGFDC genes was found. The development of magnetic responses after transfer to iron-sufficient conditions was similar in iron-starved wild-type and ΔmamC cultures (FIG. 4). Freshly inoculated cultures were nearly non-magnetic ($C_{mag}$<0.1), and magnetic responses increased within the first 3 h of cultivation to a level which remained almost unchanged during further growth, indicating that the dynamics of magnetite formation are unaffected in the ΔmamC mutant. Likewise, lack of the MamGFDC proteins did not affect the development of the magnetic response at high iron concentration. At low iron concentrations, however, magnetic response of the ΔmamGFDC cultures was close to detection limit during the first 10 h of cultivation, which might result from slower growth of crystals to sizes of permanent magnetic remanence. At non-limiting iron concentrations for magnetite formation, $C_{mag}$ values of ΔmamGFDC cultures were slightly lower than those of the wild-type due to the less regular chain arrangement and smaller crystal size.

3.6. The ΔmamGFDC Mutant Forms Wild-Type-Like Magnetosome Membrane Vesicles

Figure 5:
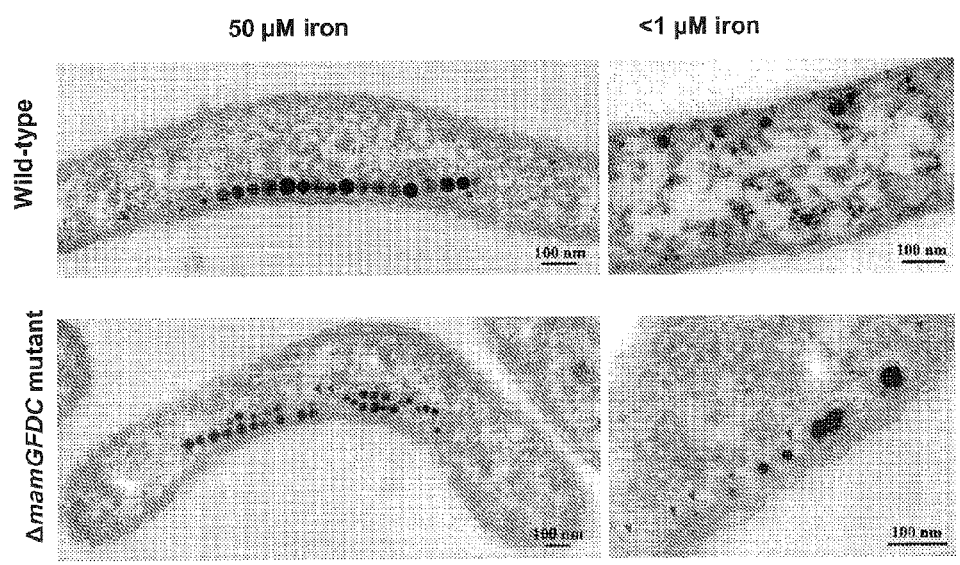
FIG. 5 illustrates transmission electron micrographs of magnetosome vesicles. Ultrathin sections were prepared from wild-type and ΔmamGFDC mutant strains grown under iron-sufficient (50 μM ferric citrate) and iron-limited (<1 μM iron) conditions. Arrows indicate empty and partially filled magnetosome membrane vesicles.
Figure 6:
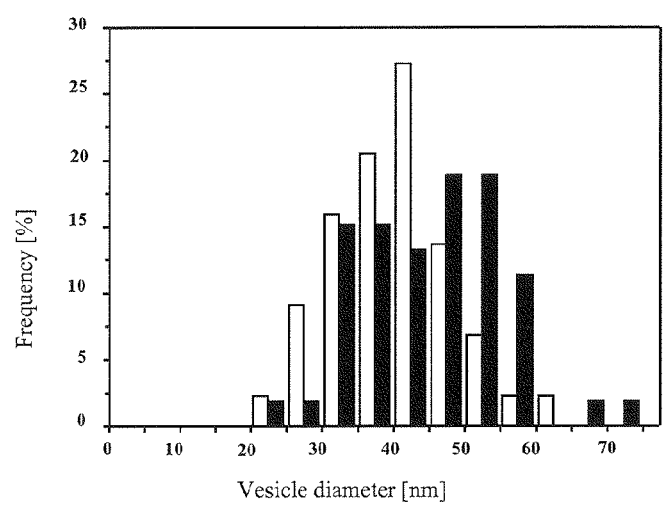
FIG. 6 depicts the size distribution of the diameters of empty magnetosome vesicles in iron-starved cells of the ΔmamGFDC mutant and the wild-type (P>1E-02). Solid bars represent the wild-type, empty bars the ΔmamGFDC mutant.

Another possible reason for the observed growth inhibition of magnetite crystals in the ΔmamGFDC mutant could be the formation of aberrantly shaped or sized membrane vesicles, which could constrain the growth of crystals by size limitation. Isolated ΔmamGFDC magnetosomes such as those from the wild-type were associated with an organic envelope (FIG. 3BIII), suggesting that the formation of the magnetosome membrane was not prevented by the deletion. The structure of the magnetosome membrane prior to magnetite synthesis was analyzed by TEM of thin-sectioned iron-starved cells. Both empty and partially filled magnetosome vesicles were visible in micrographs of the mutant. These vesicles had the same spherical shape and bilaminar structure as in the wild-type (FIG. 5). Slightly elongated vesicles were occasionally observed, but these were present in both the mutant and the wild-type. In wild-type and in mutant cells the membrane layer had a thickness of approximately 6 nm. Size measurements of about 50 vesicles in mutant and wild-type cells revealed that they are of variable sizes, and the average width of mutant vesicles appeared slightly decreased compared to the wild-type (wild-type: d=44.9 nm, ΔGFDC mutant: d=40.3 nm) (FIG. 6). Statistical comparison of vesicle size distributions, however, revealed that the difference is below significance (P>1E-2). In addition, in both strains the mean diameter of empty vesicles significantly exceeded the mean diameter of mature magnetite particles, suggesting that the growth of crystals is not limited by spatial constraints.

3.7. The MamGFDC Proteins Act in a Cumulative Manner on Crystal Size

After confirming that the phenotype can be restored to wild-type level in the ΔmamGFDC mutant by in trans-complementation (FIG. 3C, Tables 3 and 4), the contributions of the individual mamGFDC genes with respect to the observed effects on crystal size and shape development were assessed by performing complementation assays. Instead of generating numerous different knockout mutants, 13 variants of the mamGFDC operon were constructed, which permitted the in trans expression of all individual genes of the operon as well as any combination of them in the ΔmamGFDC mutant. Comparison of crystal sizes from different complemented mutants with those produced by the wild-type and the ΔmamGFDC mutant showed in most cases that differences between CSDs are statistically significant, indicating that complementation had a measurable effect on crystal size.

Figure 7:
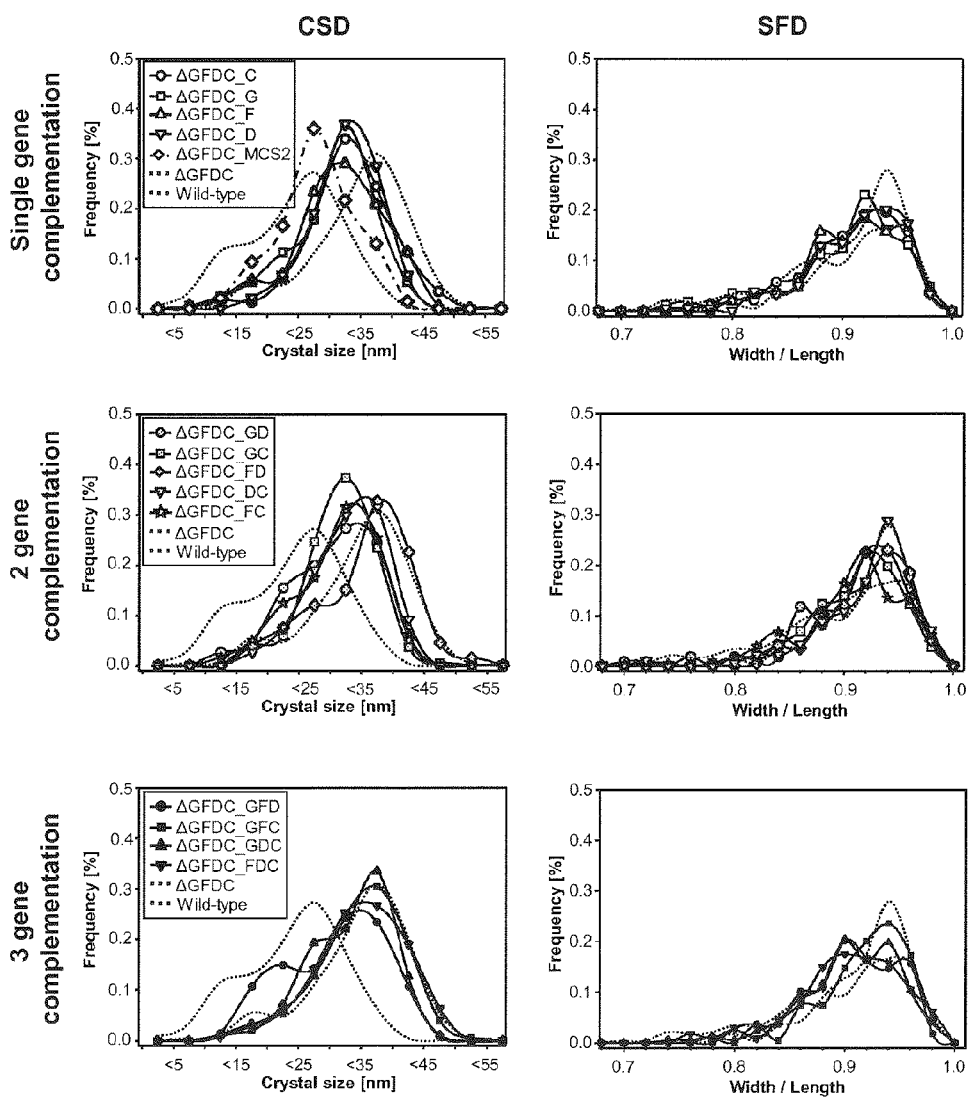
FIG. 7 shows the results of the complementation analysis of the ΔmamGFDC mutant, in particular the size and shape factor distributions of the magnetite crystals produced by ΔmamGFDC strains in trans complemented with engineered variants of the mamGFDC cluster.

Strains complemented with only one of the four mamGFDC genes (strains ΔGFDC_G, ΔGFDC_F, and ΔGFDC_D) or with any two genes (strains ΔGFDC_GD, ΔGFDC_GC, ΔGFDC_FC, and ΔGFDC_DC) produced mature crystals larger than those in the ΔmamGFDC mutant, but smaller than those in the wild-type, suggesting that crystal size is not controlled by a single gene of the mamGFDC cluster (FIG. 7, Tables 3 and 4). In contrast, strains complemented with any three of the four mamGFDC genes (strains ΔGFDC_GFC, ΔGFDC_GDC, and ΔGFDC_FDC) produced mature crystals of about wild-type size (P>1E-03) (FIG. 7, Tables 3 and 4). Although the CSDs of strains ΔGFDC_C, ΔGFDC_FD, and ΔGFDC_GFD represent minor deviations from the general trend, these data strongly argue that restoration of wild-type-like crystal sizes requires at least three of the four MamGFDC proteins, almost independently of their combination. This suggests the MamGFDC proteins to act in a cumulative manner on crystals size. In contrast, no significant effect of individual MamGFDC proteins on crystal shape was detected, as differences between SFDs of wild-type, ΔmamGFDC mutant, and complemented mutant strains were mostly below significance (FIG. 7, Tables 3 and 4).

Example 4

Summary/Discussion

In this study, the function of the abundant magnetosome membrane proteins (MMPs) encoded in the mamGFDC operon was analyzed by localization studies, deletion mutagenesis, and complementation analysis. Targeted mutagenesis was done by establishing an alternative mutagenesis approach utilizing the Cre-loxP system for antibiotic marker recycling (Marx, C. J., and Lidstrom, M. E (2002), supra) for generating the ΔmamC mutant strain. As most mam and mms genes are arranged in polycistronic operons, mutagenesis strategies require the construction of unmarked in frame deletions whose generation in magnetotactic bacteria has remained notoriously cumbersome due to difficulties in enforcing multiple double-crossover events. The present mutagenesis system was found to provide an advantage over the conventional techniques, and the exchange of the targeted locus by a selective marker allows selection against revertant growth. In addition, marker recycling by the site-specific Cre recombinase may enable the generation of strains bearing multiple genetic modifications with only a single selectable marker gene. In combination with the in trans-expression of mutant variants of entire operons, which circumvents the tedious chromosomal insertion of mutant alleles, this has proven a feasible strategy for genetic analysis in magnetotactic bacteria, whose genetic manipulation has remained cumbersome.

Although the MamGFDC proteins were previously identified by co-purification with the magnetosome particles, it was not clear if their localization is confined to the magnetosome membrane (MM), or if they are shared by other cellular compartments, e.g. by contributing to the assembly of filamentous structures implicated in magnetosome chain organization. The in vivo localization experiments demonstrated that all three proteins analyzed by EGFP fusions are localized at mid-cell in a linear manner. Both the length and width of the fluorescence signal as well as its position and slightly punctuate appearance are consistent with the position of the magnetosome chain. In contrast to the magnetosome proteins MamA, MamJ, and MamK, which localize as filament-like structures traversing the cell (Komeili, A. et al. (2004) *Proc. Natl. Acad. Sci. U.S.A.* 101, 3839-3844; Komeili, A. et al. (2006) *Science* 311, 242-245; Scheffel, A. et al. (2006) *Nature* 440, 110-115), the localization of EGFP fused to either MamC, MamG, and MamF appears confined to the presumed position of the magnetosome chain. This is in agreement with the previous observation that an orthologous MamC protein (named Mam12), was exclusively located in the MM in *Magnetospirillum magnetotacticum* (Taoka, A. et al. (2006) *J. Bacteriol.* 188, 3805-3812). Together with the results of mutagenesis studies these data argue that MamC, MamG, and MamF are specifically targeted to the magnetosome membrane, and suggest an involvement in the control of magnetite biomineralization rather then in magnetosome organization or general cell metabolism.

Surprisingly, neither of MamC, MamG, MamF, and MamD, which together account for approximately 35% of all MMPs, appears essential for magnetite biomineralization. The loss of the most abundant magnetosome protein MamC only had a minor effect on the size of mature crystals. Even the absence of all four proteins did not entirely abolish magnetosome formation. However, the loss of MamGFDC had a significant effect on crystal size and chain organization, indicating that these proteins might have regulatory or accessory functions. The complementation study of the ΔmamGFDC mutant suggested that they have overlapping and partially redundant functions and may collectively act on the crystal size. One possible explanation for the unexpectedly weak phenotype of the ΔmamGFDC mutant might be the presence of a further mamF-like gene (mmsF) identified within the mms6 operon, which could have a redundant function and may partially compensate the loss of the mamF gene and even the entire operon.

The data suggest that the mode of action of MamGFDC is correlated to the expression of these heterogeneous genes, and surprisingly the in trans-expression of additional copies of the entire mamGFDC operon in the wild-type yielded magnetite particles even larger then in the wild-type. In principle, there are several different factors that may affect the growth of magnetite crystals, such as the size and the shape of the vesicles, which spatially constrain crystal growth. It could have been envisioned, for instance, that the absence of four abundant integral membrane proteins accounting for as much as 35% of the total magnetosome-associated proteins would have a marked effect on the surface and curvature of magnetosome membrane vesicles. However, magnetosome vesicles of wild-type and ΔmamGFDC mutant cells had very similar sizes, shapes, and structures, and were, in both strains, on average larger than mature magnetite crystals. This argues against the idea that the smaller size of crystals in the mamGFDC mutant may simply be caused by a reduced vesicle size. However, the size determination from thin sections bears the risk of underestimation, as vesicles may not always been sliced exactly along their maximum widths but more peripherally or tangentially. Therefore, methods such as cryo-electrontomography might be used to determine the spatial dimensions from a statistical number of three-dimensional vesicles more precisely.

Another possible explanation for the data observed would be a reduced flux of iron into the magnetosome vesicles. However, crystal growth inhibition was independent from the availability of iron in the medium, and the heterogeneous MamGFDC proteins lack any similarity to known transporters, which seems to argue against their direct involvement in iron transport into the MM vesicles. It has been suggested that magnetosome vesicles need to be "activated" for magnetosome formation, for example by the action of the magnetosome protein MamA (Komeili, A. et al. (2004), supra). The observation that any combination of several different, unrelated proteins is capable of gradually restoring the mutant phenotype appears to argue against a similar role of MamGFDC proteins.

Alternatively, the MamGFDC proteins might act on the growth of magnetite crystals by regulating the physicochemical conditions with the interior of vesicles, such as the charge distribution at the inner surface of vesicles or the intravesicular pH and redox conditions. For example, it was shown that size and shape of crystals of *M. gryphiswaldense* are strongly affected by redox conditions during magnetite biomineralization, and an inhibition of crystal growth was observed under highly oxidizing conditions, resulting in small and imperfect particles resembling those in the ΔmamGFDC mutant strain (Heyen, U. and Schüler, D. (2003) *Appl. Microbial. Biotechnol.* 61, 536-544). Intriguingly, the selective expression of different magnetosome proteins resulted in distinct mean particle sizes that consistently differed by only a few nanometers, while the number of magnetosomes per cell was not affected. Thus, a further fine tuning of the MamGFDC gene expression might provide one strategy for the precise control of the particle size.

The present invention illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by embodiments and optional features, modifications and variations of the inventions embodied therein may be resorted to by those skilled in the art, and that such modifications and variations are considered to be within the scope of this invention.

The invention has been described broadly and generically herein. Each of the narrower species and sub-generic groupings falling within the generic disclosure also form part of the invention. This includes the generic description of the invention with a proviso or negative limitation removing any subject matter from the genus, regardless of whether or not the excised material is specifically recited herein.

Other embodiments are within the following claims. In addition, where features or aspects of the invention are described in terms of Markush groups, those skilled in the art will recognize that the invention is also thereby described in terms of any individual member or subgroup of members of the Markush group.

The invention claimed is:

1. A method for the recombinant production of magnetic nanoparticles, comprising:
   (a) providing one or more cells capable of producing magnetic nanoparticles, comprising one or more genes having a modified expression as compared to the expression of the corresponding one or more wild-type genes,
   (b) cultivating the cells; and
   (c) isolating the magnetic nanoparticles from the cultivated cells,
   wherein the one or more genes are selected from the group consisting of the mamG, mamF, mamD, and mamC genes of *Magnetospirillum gryphiswaldense*;
   wherein the modified expression results from a deletion in the one or more cells of the one or more genes, an introduction into the one or more cells of a nucleic acid molecule comprising a nucleotide sequence encoding one or more copies of the one or more genes, or combinations thereof;

wherein the nucleotide sequence encodes a genetic construct selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, and SEQ ID NO: 14;

wherein the magnetic nanoparticles have a defined size; and wherein said defined size varies depending on the type and the extent of the modification of gene expression performed.

2. The method of claim 1, wherein the size of the magnetic nanoparticles produced is 20 nm to 150 nm in diameter.

3. The method of claim 2, wherein the size of the magnetic nanoparticles produced is selected from the group consisting of 5 nm to 50 nm in diameter and greater than 50 nm in diameter.

4. The method of claim 2, wherein the size of at least 80% of the magnetic nanoparticles produced is within the range given by the mean diameter±10%.

5. The method of claim 1, wherein said one or more cells is selected from the group consisting of prokaryotic or eukaryotic cells.

6. The method of claim 5, wherein said one or more cells is a prokaryotic cell.

7. The method of claim 6, wherein said prokaryotic cell is a bacterial cell.

8. The method of claim 7, wherein said bacterial cell is a magnetotactic bacterial cell.

9. The method of claim 8, wherein said magnetotactic bacteria cell is from the genus *Magnetospirillum*.

10. The method of claim 1, wherein the magnetic nanoparticles are monocrystals consisting of magnetite.

11. The method of claim 10, wherein the monocrystals further comprise a phospholipid outer membrane.

* * * * *

SEQUENCE LISTING

<160> NUMBER OF SEQ ID NOS: 14

<210> SEQ ID NO 1
<211> LENGTH: 2077
<212> TYPE: DNA
<213> ORGANISM: Artificial Sequence
<220> FEATURE:
<223> OTHER INFORMATION: Fragment of the mamGFDC operon of
      Magnetospirillum gryphiswaldense
<220> FEATURE:
<221> NAME/KEY: CDS
<222> LOCATION: (1)..(255)
<223> OTHER INFORMATION: Coding sequence of the mamG gene of M.
      gryphiswaldense
<220> FEATURE:
<221> NAME/KEY: CDS
<222> LOCATION: (270)..(605)
<223> OTHER INFORMATION: Coding sequence of the mamF gene of M.
      gryphiswaldense
<220> FEATURE:
<221> NAME/KEY: CDS
<222> LOCATION: (726)..(1670)
<223> OTHER INFORMATION: Coding sequence of the mamD gene of M.
      gryphiswaldense
<220> FEATURE:
<221> NAME/KEY: CDS
<222> LOCATION: (1700)..(2077)
<223> OTHER INFORMATION: Coding sequence of the mamC gene of M.
      gryphiswaldense

<400> SEQUENCE: 1

```
atg atc aag ggc atc gcc ggc gtt ggc gga acc gcc ctt ggc gtc ggt        48
Met Ile Lys Gly Ile Ala Gly Val Gly Gly Thr Ala Leu Gly Val Gly
1               5                   10                  15 ggc gga gtt gcc gcc cct ccg gtc tct gcc gct gct gtc ggc agc acc       96
Gly Gly Val Ala Ala Pro Pro Val Ser Ala Ala Ala Val Gly Ser Thr
            20                  25                  30 ttg ctg gcc ggc aag ggg gtg tgc ctg ggg ctg ggg ctt ggc ctc ggt      144
Leu Leu Ala Gly Lys Gly Val Cys Leu Gly Leu Gly Leu Gly Leu Gly
        35                  40                  45 gct tgg ggt ccc gtt ctt ctc ggc gtt gcc gga ttg gct tgc gcc gcc      192
Ala Trp Gly Pro Val Leu Leu Gly Val Ala Gly Leu Ala Cys Ala Ala
    50                  55                  60 tcc cta tgt gat tat ctg aag aat cgc aaa gcg cag gct gag gcc agc      240
Ser Leu Cys Asp Tyr Leu Lys Asn Arg Lys Ala Gln Ala Glu Ala Ser
65                  70                  75                  80 gct gag cct gct taa gcgagggcaa agca atg gcc gag act att ttg atc     290
Ala Glu Pro Ala                   Met Ala Glu Thr Ile Leu Ile
                                  85                  90 gaa act aaa aca gct ggc ggc aac tgc cgt tca tat ctg atg gcg ggc      338
Glu Thr Lys Thr Ala Gly Gly Asn Cys Arg Ser Tyr Leu Met Ala Gly
            95                  100                 105 gct agc tat ctg ggc atc ctc tgc ttc gtc ccg ctt atg agc cgc          386
Ala Ser Tyr Leu Gly Ile Leu Cys Phe Val Pro Leu Leu Met Ser Arg
            110                 115                 120 gat gac gaa tat gtg tac ttc cat gcc aag cag ggg ctg gtg ctg tgg      434
Asp Asp Glu Tyr Val Tyr Phe His Ala Lys Gln Gly Leu Val Leu Trp
        125                 130                 135 atg tgg agc atc ctg gcc atg ttc gcg ctg cat ctg ccg ggc atc ggc      482
Met Trp Ser Ile Leu Ala Met Phe Ala Leu His Leu Pro Gly Ile Gly
140                 145                 150                 155
```

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| aag | tgg | ctc | ttc | ggc | ttc | tcg | tcc | atg | ggc | gtc | ctg | atg | ctg | tcc | gtg | 530  |
| Lys | Trp | Leu | Phe | Gly | Phe | Ser | Ser | Met | Gly | Val | Leu | Met | Leu | Ser | Val |      |
|     |     |     | 160 |     |     |     |     | 165 |     |     |     |     | 170 |     |     |      |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| gtc | ggc | ttg | gtc | tcg | gtg | gcg | ctg | cgc | cgc | acc | tgg | cgt | ctg | ccc | ctt | 578  |
| Val | Gly | Leu | Val | Ser | Val | Ala | Leu | Arg | Arg | Thr | Trp | Arg | Leu | Pro | Leu |      |
|     |     | 175 |     |     |     |     | 180 |     |     |     |     | 185 |     |     |     |      |

|     |     |     |     |     |     |     |     |                    |     |
|-----|-----|-----|-----|-----|-----|-----|-----|--------------------|-----|
| ata | agc | cat | gta | gtc | gcc | ctg | atc | tga cggcgagcga tctaacggac | 625 |
| Ile | Ser | His | Val | Val | Ala | Leu | Ile |                    |     |
|     |     | 190 |     |     |     | 195 |     |                    |     |

| ccggacagca gcgcaagcac gcgaccggag tcctttgctt tggagtccca agcggcttct | 685 |
|---|---|

|                                                       |     |     |     |     |     |      |
|-------------------------------------------------------|-----|-----|-----|-----|-----|------|
| gccatgtagg cgcagtttcg tctcaggaaa ggccaatacc | atg | cag | gac | ctt | ttt | 740  |
|                                                       | Met | Gln | Asp | Leu | Phe |      |
|                                                       |     |     |     |     | 200 |      |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| ctc | gcg | aag | gtc | gaa | agc | gcc | atg | cag | gcg | tcc | cag | gtc | ggg | gca | ctt | 788  |
| Leu | Ala | Lys | Val | Glu | Ser | Ala | Met | Gln | Ala | Ser | Gln | Val | Gly | Ala | Leu |      |
|     |     |     |     | 205 |     |     |     |     | 210 |     |     |     |     | 215 |     |      |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| gcc | ggt | cag | acg | gcg | acg | gtc | tcg | tca | gtc | tcg | gcc | acg | acc | aat | ctg | 836  |
| Ala | Gly | Gln | Thr | Ala | Thr | Val | Ser | Ser | Val | Ser | Ala | Thr | Thr | Asn | Leu |      |
|     |     |     | 220 |     |     |     |     | 225 |     |     |     |     | 230 |     |     |      |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| gcc | acc | ata | acc | cca | acc | acc | gcc | ggg | cag | gcc | cct | atc | atc | gtc | aaa | 884  |
| Ala | Thr | Ile | Thr | Pro | Thr | Thr | Ala | Gly | Gln | Ala | Pro | Ile | Ile | Val | Lys |      |
|     |     |     | 235 |     |     |     |     | 240 |     |     |     |     | 245 |     |     |      |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| ctg | gac | gcg | gca | cgg | cag | gtg | acg | gag | ttg | cag | gcc | ctg | atg | gga | aag | 932  |
| Leu | Asp | Ala | Ala | Arg | Gln | Val | Thr | Glu | Leu | Gln | Ala | Leu | Met | Gly | Lys |      |
|     | 250 |     |     |     |     | 255 |     |     |     |     | 260 |     |     |     |     |      |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| acc | gtg | ctg | gtc | gga | aag | acc | ccg | acc | acc | atc | ggc | ggc | atc | gga | aac | 980  |
| Thr | Val | Leu | Val | Gly | Lys | Thr | Pro | Thr | Thr | Ile | Gly | Gly | Ile | Gly | Asn |      |
| 265 |     |     |     |     | 270 |     |     |     |     | 275 |     |     |     |     | 280 |      |

|     |     |     |     |     |     |     |     |     |     |     |     |     |     |     |      |
|-----|-----|-----|-----|-----|-----|-----|-----|-----|-----|-----|-----|-----|-----|-----|------|
| tgg | att | gcc | ttg | acc | ccg | gcg | gcg | gga | gcc | aag | acc | ggc | gct | gcc | gtg | 1028 |
| Trp | Ile | Ala | Leu | Thr | Pro | Ala | Ala | Gly | Ala | Lys | Thr | Gly | Ala | Ala | Val |      |
|     |     |     | 285 |     |     |     |     | 290 |     |     |     |     | 295 |     |     |      |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| gcc | gga | acc | ggt | cag | ctt | gtc | atg | atg | aag | gtc | gag | ggc | acc | ggc | gcg | 1076 |
| Ala | Gly | Thr | Gly | Gln | Leu | Val | Met | Met | Lys | Val | Glu | Gly | Thr | Gly | Ala |      |
|     |     | 300 |     |     |     |     | 305 |     |     |     |     | 310 |     |     |     |      |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| gcc | atc | aag | ctt | ccc | gcc | ctg | gcg | ggt | aag | agc | ttc | atc | gtc | gcc | cag | 1124 |
| Ala | Ile | Lys | Leu | Pro | Ala | Leu | Ala | Gly | Lys | Ser | Phe | Ile | Val | Ala | Gln |      |
|     | 315 |     |     |     |     | 320 |     |     |     |     | 325 |     |     |     |     |      |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| ccc | ccc | gta | gcc | gcc | gga | acc | aaa | gcg | gcg | ggc | atg | ctc | tat | ctg | aat | 1172 |
| Pro | Pro | Val | Ala | Ala | Gly | Thr | Lys | Ala | Ala | Gly | Met | Leu | Tyr | Leu | Asn |      |
| 330 |     |     |     |     | 335 |     |     |     |     | 340 |     |     |     |     |     |      |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| ccg | gtt | ggc | ggt | ggt | gat | atg | gtg | gcc | atc | aac | att | cag | aac | gcc | atg | 1220 |
| Pro | Val | Gly | Gly | Gly | Asp | Met | Val | Ala | Ile | Asn | Ile | Gln | Asn | Ala | Met |      |
| 345 |     |     |     |     | 350 |     |     |     |     | 355 |     |     |     |     | 360 |      |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| acc | cag | acc | ggc | ggc | ttg | gtc | ggc | aag | acc | ttc | acc | gtc | gcc | ccc | agc | 1268 |
| Thr | Gln | Thr | Gly | Gly | Leu | Val | Gly | Lys | Thr | Phe | Thr | Val | Ala | Pro | Ser |      |
|     |     |     | 365 |     |     |     |     | 370 |     |     |     |     | 375 |     |     |      |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| ccc | gtc | att | ggc | ggc | acc | acc | ggt | aaa | ttc | ctg | gtc | ctg | aag | ccc | atg | 1316 |
| Pro | Val | Ile | Gly | Gly | Thr | Thr | Gly | Lys | Phe | Leu | Val | Leu | Lys | Pro | Met |      |
|     |     |     | 380 |     |     |     |     | 385 |     |     |     |     | 390 |     |     |      |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| gcg | acc | ggg | gtc | ggc | aag | gcg | gtg | ggc | agc | ggc | gcc | gtc | gtc | gcc | aag | 1364 |
| Ala | Thr | Gly | Val | Gly | Lys | Ala | Val | Gly | Ser | Gly | Ala | Val | Val | Ala | Lys |      |
|     |     | 395 |     |     |     |     | 400 |     |     |     |     | 405 |     |     |     |      |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| ttc | gta | ccc | gcc | gcc | gtc | acc | ggc | acg | ggc | gga | gcg | gcg | gct | atc | ggg | 1412 |
| Phe | Val | Pro | Ala | Ala | Val | Thr | Gly | Thr | Gly | Gly | Ala | Ala | Ala | Ile | Gly |      |
|     | 410 |     |     |     |     | 415 |     |     |     |     | 420 |     |     |     |     |      |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| gcc | gga | tcc | gcc | acc | acc | ctg | atg | gcc | acg | ggc | gcc | agt | acg | atc | acc | 1460 |
| Ala | Gly | Ser | Ala | Thr | Thr | Leu | Met | Ala | Thr | Gly | Ala | Ser | Thr | Ile | Thr |      |
| 425 |     |     |     |     | 430 |     |     |     |     | 435 |     |     |     |     | 440 |      |

```
ccc gtc act gcc gcc gcc gct ggc agc gcc atg ctg aca gcc aaa ggt      1508
Pro Val Thr Ala Ala Ala Ala Gly Ser Ala Met Leu Thr Ala Lys Gly
            445                 450                 455 gtt ggc ctc ggg ctt ggc ctg ggc ctc ggc gcc tgg ggg ccg ttc gcc      1556
Val Gly Leu Gly Leu Gly Leu Gly Leu Gly Ala Trp Gly Pro Phe Ala
        460                 465                 470 cta ggg gct atc ggc cta gcg ggt gtt gtc gcg ctt tat acc tgg gcg      1604
Leu Gly Ala Ile Gly Leu Ala Gly Val Val Ala Leu Tyr Thr Trp Ala
        475                 480                 485 cgc cgc cgc cat ggc gct ccc gat gtt tcc gat gat gca ttg ctg gcg      1652
Arg Arg Arg His Gly Ala Pro Asp Val Ser Asp Asp Ala Leu Leu Ala
    490                 495                 500 gct gtc ggc gag gaa taa gcctgaccct tgaattcagg acaacagcg atg agc      1705
Ala Val Gly Glu Glu                                     Met Ser
505                                                     510 ttt caa ctt gcg ccg tac ttg gcg aaa tcc gtc cct gga atc ggc att      1753
Phe Gln Leu Ala Pro Tyr Leu Ala Lys Ser Val Pro Gly Ile Gly Ile
            515                 520                 525 ctc ggc ggc att gtc ggt ggc gcc gcc gcc ctt gcc aag aat gcc cgc      1801
Leu Gly Gly Ile Val Gly Gly Ala Ala Ala Leu Ala Lys Asn Ala Arg
        530                 535                 540 ctt ttg aag gac aag cag ata acc ggc aca gaa gcg gcc atc gac acc      1849
Leu Leu Lys Asp Lys Gln Ile Thr Gly Thr Glu Ala Ala Ile Asp Thr
    545                 550                 555 ggc aag gaa gcc gcc ggt gcc ggg ctt gcc acc gct ttc tcc gcc gtc      1897
Gly Lys Glu Ala Ala Gly Ala Gly Leu Ala Thr Ala Phe Ser Ala Val
560                 565                 570                 575 gcc gcc acc gcc gtc ggc ggt ggg ttg gtg gtc tcg ttg gga acc gcc      1945
Ala Ala Thr Ala Val Gly Gly Gly Leu Val Val Ser Leu Gly Thr Ala
            580                 585                 590 cta atc gcc ggt gtc gcc gcc aaa tac gcc tgg gac ctg ggt gtc gat      1993
Leu Ile Ala Gly Val Ala Ala Lys Tyr Ala Trp Asp Leu Gly Val Asp
        595                 600                 605 ttc atc gag aag gaa ttg cgt cac ggc aag tcc gcc gag gcg aca gcg      2041
Phe Ile Glu Lys Glu Leu Arg His Gly Lys Ser Ala Glu Ala Thr Ala
        610                 615                 620 tcc gac gaa gac att ctg agg gaa gaa ttg gcc tga                       2077
Ser Asp Glu Asp Ile Leu Arg Glu Glu Leu Ala
    625                 630

<210> SEQ ID NO 2
<211> LENGTH: 1855
<212> TYPE: DNA
<213> ORGANISM: Artificial sequence
<220> FEATURE:
<223> OTHER INFORMATION: Fragment of the mamGFDC operon of M.
      gryphiswaldense ((delta)mamG)
<220> FEATURE:
<221> NAME/KEY: CDS
<222> LOCATION: (1)..(33)
<223> OTHER INFORMATION: Remnant coding sequence of the mamG gene of M.
      gryphiswaldense
<220> FEATURE:
<221> NAME/KEY: CDS
<222> LOCATION: (48)..(383)
<223> OTHER INFORMATION: Coding sequence of the mamF gene of M.
      gryphiswaldense
<220> FEATURE:
<221> NAME/KEY: CDS
<222> LOCATION: (504)..(1448)
<223> OTHER INFORMATION: Coding sequence of the mamD gene of M.
      gryphiswaldense
<220> FEATURE:
<221> NAME/KEY: CDS
<222> LOCATION: (1478)..(1855)
<223> OTHER INFORMATION: Coding sequence of the mamC gene of M.
      gryphiswaldense
```

-continued

```
<400> SEQUENCE: 2 atg atc aag ggc atc gcc gct gag cct gct taa gcgagggcaa agca atg      50
Met Ile Lys Gly Ile Ala Ala Glu Pro Ala                    Met
1               5              10 gcc gag act att ttg atc gaa act aaa aca gct ggc ggc aac tgc cgt      98
Ala Glu Thr Ile Leu Ile Glu Thr Lys Thr Ala Gly Gly Asn Cys Arg
        15                  20                  25 tca tat ctg atg gcg ggc gct agc tat ctg ggc atc ctc tgc ttc gtc     146
Ser Tyr Leu Met Ala Gly Ala Ser Tyr Leu Gly Ile Leu Cys Phe Val
            30                  35                  40 ccg ctg ctt atg agc cgc gat gac gaa tat gtg tac ttc cat gcc aag     194
Pro Leu Leu Met Ser Arg Asp Asp Glu Tyr Val Tyr Phe His Ala Lys
            45                  50                  55 cag ggg ctg gtg ctg tgg atg tgg agc atc ctg gcc atg ttc gcg ctg     242
Gln Gly Leu Val Leu Trp Met Trp Ser Ile Leu Ala Met Phe Ala Leu
60                  65                  70                  75 cat ctg ccg ggc atc ggc aag tgg ctc ttc ggc ttc tcg tcc atg ggc     290
His Leu Pro Gly Ile Gly Lys Trp Leu Phe Gly Phe Ser Ser Met Gly
                80                  85                  90 gtc ctg atg ctg tcc gtg gtc ggc ttg gtc tcg gtg gcg ctg cgc cgc     338
Val Leu Met Leu Ser Val Val Gly Leu Val Ser Val Ala Leu Arg Arg
                95                 100                 105 acc tgg cgt ctg ccc ctt ata agc cat gta gtc gcc ctg atc tga         383
Thr Trp Arg Leu Pro Leu Ile Ser His Val Val Ala Leu Ile
            110                 115                 120 cggcgagcga tctaacggac ccggacagca gcgcaagcac gcgaccggag tcctttgctt    443
tggagtccca agcggcttct gccatgtagg cgcagtttcg tctcaggaaa ggccaatacc    503 atg cag gac ctt ttt ctc gcg aag gtc gaa agc gcc atg cag gcg tcc     551
Met Gln Asp Leu Phe Leu Ala Lys Val Glu Ser Ala Met Gln Ala Ser
                125                 130                 135 cag gtc ggg gca ctt gcc ggt cag acg gcg acg gtc tcg tca gtc tcg     599
Gln Val Gly Ala Leu Ala Gly Gln Thr Ala Thr Val Ser Ser Val Ser
        140                 145                 150 gcc acg acc aat ctg gcc acc ata acc cca acc acc gcc ggg cag gcc     647
Ala Thr Thr Asn Leu Ala Thr Ile Thr Pro Thr Thr Ala Gly Gln Ala
    155                 160                 165 cct atc atc gtc aaa ctg gac gcg gca cgg cag gtg acg gag ttg cag     695
Pro Ile Ile Val Lys Leu Asp Ala Ala Arg Gln Val Thr Glu Leu Gln
170                 175                 180                 185 gcc ctg atg gga aag acc gtg ctg gtc gga aag acc ccg acc acc atc     743
Ala Leu Met Gly Lys Thr Val Leu Val Gly Lys Thr Pro Thr Thr Ile
                190                 195                 200 ggc ggc atc gga aac tgg att gcc ttg acc ccg gcg gcg gga gcc aag     791
Gly Gly Ile Gly Asn Trp Ile Ala Leu Thr Pro Ala Ala Gly Ala Lys
                205                 210                 215 acc ggc gct gcc gtg gcc gga acc ggt cag ctt gtc atg atg aag gtc     839
Thr Gly Ala Ala Val Ala Gly Thr Gly Gln Leu Val Met Met Lys Val
            220                 225                 230 gag ggc acc ggc gcg gcc atc aag ctt ccc gcc ctg gcg ggt aag agc     887
Glu Gly Thr Gly Ala Ala Ile Lys Leu Pro Ala Leu Ala Gly Lys Ser
235                 240                 245 ttc atc gtc gcc cag ccc ccc gta gcc gcc gga acc aaa gcg gcg ggc     935
Phe Ile Val Ala Gln Pro Pro Val Ala Ala Gly Thr Lys Ala Ala Gly
250                 255                 260                 265 atg ctc tat ctg aat ccg gtt ggc ggt ggt gat atg gtg gcc atc aac     983
Met Leu Tyr Leu Asn Pro Val Gly Gly Gly Asp Met Val Ala Ile Asn
                270                 275                 280
```

```
att cag aac gcc atg acc cag acc ggc ggc ttg gtc ggc aag acc ttc       1031
Ile Gln Asn Ala Met Thr Gln Thr Gly Gly Leu Val Gly Lys Thr Phe
            285                 290                 295 acc gtc gcc ccc agc ccc gtc att ggc ggc acc acc ggt aaa ttc ctg       1079
Thr Val Ala Pro Ser Pro Val Ile Gly Gly Thr Thr Gly Lys Phe Leu
        300                 305                 310 gtc ctg aag ccc atg gcg acc ggg gtc ggc aag gcg gtg ggc agc ggc       1127
Val Leu Lys Pro Met Ala Thr Gly Val Gly Lys Ala Val Gly Ser Gly
    315                 320                 325 gcc gtc gtc gcc aag ttc gta ccc gcc gcc gtc acc ggc acg ggc gga       1175
Ala Val Val Ala Lys Phe Val Pro Ala Ala Val Thr Gly Thr Gly Gly
330                 335                 340                 345 gcg gcg gct atc ggg gcc gga tcc gcc acc acc ctg atg gcc acg ggc       1223
Ala Ala Ala Ile Gly Ala Gly Ser Ala Thr Thr Leu Met Ala Thr Gly
                350                 355                 360 gcc agt acg atc acc ccc gtc act gcc gcc gcc gct ggc agc gcc atg       1271
Ala Ser Thr Ile Thr Pro Val Thr Ala Ala Ala Ala Gly Ser Ala Met
            365                 370                 375 ctg aca gcc aaa ggt gtt ggc ctc ggg ctt ggc ctg ggc ctc ggc gcc       1319
Leu Thr Ala Lys Gly Val Gly Leu Gly Leu Gly Leu Gly Leu Gly Ala
        380                 385                 390 tgg ggg ccg ttc gcc cta ggg gct atc ggc cta gcg ggt gtt gtc gcg       1367
Trp Gly Pro Phe Ala Leu Gly Ala Ile Gly Leu Ala Gly Val Val Ala
    395                 400                 405 ctt tat acc tgg gcg cgc cgc cgc cat ggc gct ccc gat gtt tcc gat       1415
Leu Tyr Thr Trp Ala Arg Arg Arg His Gly Ala Pro Asp Val Ser Asp
410                 415                 420                 425 gat gca ttg ctg gcg gct gtc ggc gag gaa taa gcctgaccct tgaattcagg    1468
Asp Ala Leu Leu Ala Ala Val Gly Glu Glu
                430                 435 acaacagcg atg agc ttt caa ctt gcg ccg tac ttg gcg aaa tcc gtc cct    1519
          Met Ser Phe Gln Leu Ala Pro Tyr Leu Ala Lys Ser Val Pro
          440                 445 gga atc ggc att ctc ggc ggc att gtc ggt ggc gcc gcc gcc ctt gcc      1567
Gly Ile Gly Ile Leu Gly Gly Ile Val Gly Gly Ala Ala Ala Leu Ala
450                 455                 460                 465 aag aat gcc cgc ctt ttg aag gac aag cag ata acc ggc aca gaa gcg      1615
Lys Asn Ala Arg Leu Leu Lys Asp Lys Gln Ile Thr Gly Thr Glu Ala
                470                 475                 480 gcc atc gac acc ggc aag gaa gcc gcc ggt gcc ggg ctt gcc acc gct      1663
Ala Ile Asp Thr Gly Lys Glu Ala Ala Gly Ala Gly Leu Ala Thr Ala
            485                 490                 495 ttc tcc gcc gtc gcc gcc acc gcc gtc ggc ggt ggg ttg gtg gtc tcg      1711
Phe Ser Ala Val Ala Ala Thr Ala Val Gly Gly Gly Leu Val Val Ser
        500                 505                 510 ttg gga acc gcc cta atc gcc ggt gtc gcc gcc aaa tac gcc tgg gac      1759
Leu Gly Thr Ala Leu Ile Ala Gly Val Ala Ala Lys Tyr Ala Trp Asp
    515                 520                 525 ctg ggt gtc gat ttc atc gag aag gaa ttg cgt cac ggc aag tcc gcc      1807
Leu Gly Val Asp Phe Ile Glu Lys Glu Leu Arg His Gly Lys Ser Ala
530                 535                 540                 545 gag gcg aca gcg tcc gac gaa gac att ctg agg gaa gaa ttg gcc tga      1855
Glu Ala Thr Ala Ser Asp Glu Asp Ile Leu Arg Glu Glu Leu Ala
                550                 555                 560

<210> SEQ ID NO 3
<211> LENGTH: 1801
<212> TYPE: DNA
<213> ORGANISM: Artificial sequence
<220> FEATURE:
<223> OTHER INFORMATION: Fragment of the mamGFDC operon of M.
      gryphiswaldense ((delta)mamF)
```

```
<220> FEATURE:
<221> NAME/KEY: CDS
<222> LOCATION: (1)..(255)
<223> OTHER INFORMATION: Coding sequence of the mamG gene of M.
      gryphiswaldense
<220> FEATURE:
<221> NAME/KEY: CDS
<222> LOCATION: (270)..(329)
<223> OTHER INFORMATION: Coding sequence of the mamF gene of M.
      gryphiswaldense
<220> FEATURE:
<221> NAME/KEY: CDS
<222> LOCATION: (450)..(1394)
<223> OTHER INFORMATION: Coding sequence of the mamD gene of M.
      gryphiswaldense
<220> FEATURE:
<221> NAME/KEY: CDS
<222> LOCATION: (1424)..(1801)
<223> OTHER INFORMATION: Coding sequence of the mamD gene of M.
      gryphiswaldense

<400> SEQUENCE: 3
```

| | | | | | | | | | | | | | | | | |
|---|---|---|---|---|---|---|---|---|---|---|---|---|---|---|---|---|
| atg | atc | aag | ggc | atc | gcc | ggc | gtt | ggc | gga | acc | gcc | ctt | ggc | gtc | ggt | 48 |
| Met | Ile | Lys | Gly | Ile | Ala | Gly | Val | Gly | Gly | Thr | Ala | Leu | Gly | Val | Gly | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| ggc | gga | gtt | gcc | gcc | cct | ccg | gtc | tct | gcc | gct | gct | gtc | ggc | agc | acc | 96 |
| Gly | Gly | Val | Ala | Ala | Pro | Pro | Val | Ser | Ala | Ala | Ala | Val | Gly | Ser | Thr | |
| | | | 20 | | | | | 25 | | | | | 30 | | | |

| | | | | | | | | | | | | | | | | |
|---|---|---|---|---|---|---|---|---|---|---|---|---|---|---|---|---|
| ttg | ctg | gcc | ggc | aag | ggg | gtg | tgc | ctg | ggg | ctg | ggg | ctt | ggc | ctc | ggt | 144 |
| Leu | Leu | Ala | Gly | Lys | Gly | Val | Cys | Leu | Gly | Leu | Gly | Leu | Gly | Leu | Gly | |
| | 35 | | | | | 40 | | | | | 45 | | | | | |

| | | | | | | | | | | | | | | | | |
|---|---|---|---|---|---|---|---|---|---|---|---|---|---|---|---|---|
| gct | tgg | ggt | ccc | gtt | ctt | ctc | ggc | gtt | gcc | gga | ttg | gct | tgc | gcc | gcc | 192 |
| Ala | Trp | Gly | Pro | Val | Leu | Leu | Gly | Val | Ala | Gly | Leu | Ala | Cys | Ala | Ala | |
| 50 | | | | | 55 | | | | | 60 | | | | | | |

| | | | | | | | | | | | | | | | | |
|---|---|---|---|---|---|---|---|---|---|---|---|---|---|---|---|---|
| tcc | cta | tgt | gat | tat | ctg | aag | aat | cgc | aaa | gcg | cag | gct | gag | gcc | agc | 240 |
| Ser | Leu | Cys | Asp | Tyr | Leu | Lys | Asn | Arg | Lys | Ala | Gln | Ala | Glu | Ala | Ser | |
| 65 | | | | | 70 | | | | | 75 | | | | | 80 | |

| | | | | | | | | | | | | | |
|---|---|---|---|---|---|---|---|---|---|---|---|---|---|
| gct | gag | cct | gct | taa | gcgagggcaa | agca | atg | gcc | gag | act | att | ttg | atc | 290 |
| Ala | Glu | Pro | Ala | | | | Met | Ala | Glu | Thr | Ile | Leu | Ile |
| | | | | | | | 85 | | | | | | 90 |

| | | | | | | | | | | |
|---|---|---|---|---|---|---|---|---|---|---|
| gaa | act | aaa | aca | gta | agc | cat | gta | gtc | gcc | ctg | atc | tga | cggcgagcga | 339 |
| Glu | Thr | Lys | Thr | Val | Ser | His | Val | Val | Ala | Leu | Ile | | | |
| | | 95 | | | | | 100 | | | | | | | |

| | | |
|---|---|---|
| tctaacggac | ccggacagca | gcgcaagcac | gcgaccggag | tcctttgctt | tggagtccca | 399 |

| | | | | |
|---|---|---|---|---|
| agcggcttct | gccatgtagg | cgcagtttcg | tctcaggaaa | ggccaatacc | atg | cag | 455 |
| | | | | | Met | Gln | |
| | | | | | | 105 | |

| | | | | | | | | | | | | | | | | |
|---|---|---|---|---|---|---|---|---|---|---|---|---|---|---|---|---|
| gac | ctt | ttt | ctc | gcg | aag | gtc | gaa | agc | gcc | atg | cag | gcg | tcc | cag | gtc | 503 |
| Asp | Leu | Phe | Leu | Ala | Lys | Val | Glu | Ser | Ala | Met | Gln | Ala | Ser | Gln | Val | |
| | | | 110 | | | | | 115 | | | | | 120 | | | |

| | | | | | | | | | | | | | | | | |
|---|---|---|---|---|---|---|---|---|---|---|---|---|---|---|---|---|
| ggg | gca | ctt | gcc | ggt | cag | acg | gcg | acg | gtc | tcg | tca | gtc | tcg | gcc | acg | 551 |
| Gly | Ala | Leu | Ala | Gly | Gln | Thr | Ala | Thr | Val | Ser | Ser | Val | Ser | Ala | Thr | |
| | | | 125 | | | | | 130 | | | | | 135 | | | |

| | | | | | | | | | | | | | | | | |
|---|---|---|---|---|---|---|---|---|---|---|---|---|---|---|---|---|
| acc | aat | ctg | gcc | acc | ata | acc | cca | acc | acc | gcg | ggg | cag | gcc | cct | atc | 599 |
| Thr | Asn | Leu | Ala | Thr | Ile | Thr | Pro | Thr | Thr | Ala | Gly | Gln | Ala | Pro | Ile | |
| | | 140 | | | | | 145 | | | | | 150 | | | | |

| | | | | | | | | | | | | | | | | |
|---|---|---|---|---|---|---|---|---|---|---|---|---|---|---|---|---|
| atc | gtc | aaa | ctg | gac | gcg | gca | cgg | cag | gtg | acg | gag | ttg | cag | gcc | ctg | 647 |
| Ile | Val | Lys | Leu | Asp | Ala | Ala | Arg | Gln | Val | Thr | Glu | Leu | Gln | Ala | Leu | |
| | 155 | | | | | 160 | | | | | 165 | | | | | |

| | | | | | | | | | | | | | | | | |
|---|---|---|---|---|---|---|---|---|---|---|---|---|---|---|---|---|
| atg | gga | aag | acc | gtg | ctg | gtc | gga | aag | acc | ccg | acc | acc | atc | ggc | ggc | 695 |
| Met | Gly | Lys | Thr | Val | Leu | Val | Gly | Lys | Thr | Pro | Thr | Thr | Ile | Gly | Gly | |
| 170 | | | | | 175 | | | | | 180 | | | | | 185 | |

| | | | | | | | | | | | | | | | | |
|---|---|---|---|---|---|---|---|---|---|---|---|---|---|---|---|---|
| atc | gga | aac | tgg | att | gcc | ttg | acc | ccg | gcg | gcg | gga | gcc | aag | acc | ggc | 743 |
| Ile | Gly | Asn | Trp | Ile | Ala | Leu | Thr | Pro | Ala | Ala | Gly | Ala | Lys | Thr | Gly | |
| | | | 190 | | | | | 195 | | | | | 200 | | | |

```
gct gcc gtg gcc gga acc ggt cag ctt gtc atg atg aag gtc gag ggc        791
Ala Ala Val Ala Gly Thr Gly Gln Leu Val Met Met Lys Val Glu Gly
            205                 210                 215 acc ggc gcg gcc atc aag ctt ccc gcc ctg gcg ggt aag agc ttc atc        839
Thr Gly Ala Ala Ile Lys Leu Pro Ala Leu Ala Gly Lys Ser Phe Ile
        220                 225                 230 gtc gcc cag ccc ccc gta gcc gcc gga acc aaa gcg gcg ggc atg ctc        887
Val Ala Gln Pro Pro Val Ala Ala Gly Thr Lys Ala Ala Gly Met Leu
    235                 240                 245 tat ctg aat ccg gtt ggc ggt ggt gat atg gtg gcc atc aac att cag        935
Tyr Leu Asn Pro Val Gly Gly Gly Asp Met Val Ala Ile Asn Ile Gln
250                 255                 260                 265 aac gcc atg acc cag acc ggc ggc ttg gtc ggc aag acc ttc acc gtc        983
Asn Ala Met Thr Gln Thr Gly Gly Leu Val Gly Lys Thr Phe Thr Val
            270                 275                 280 gcc ccc agc ccc gtc att ggc ggc acc acc ggt aaa ttc ctg gtc ctg       1031
Ala Pro Ser Pro Val Ile Gly Gly Thr Thr Gly Lys Phe Leu Val Leu
        285                 290                 295 aag ccc atg gcg acc ggg gtc ggc aag gcg gtg ggc agc ggc gcc gtc       1079
Lys Pro Met Ala Thr Gly Val Gly Lys Ala Val Gly Ser Gly Ala Val
    300                 305                 310 gtc gcc aag ttc gta ccc gcc gcc gtc acc ggc acg ggc gga gcg gcg       1127
Val Ala Lys Phe Val Pro Ala Ala Val Thr Gly Thr Gly Gly Ala Ala
315                 320                 325 gct atc ggg gcc gga tcc gcc acc acc ctg atg gcc acg ggc gcc agt       1175
Ala Ile Gly Ala Gly Ser Ala Thr Thr Leu Met Ala Thr Gly Ala Ser
330                 335                 340                 345 acg atc acc ccc gtc act gcc gcc gcc gct ggc agc gcc atg ctg aca       1223
Thr Ile Thr Pro Val Thr Ala Ala Ala Ala Gly Ser Ala Met Leu Thr
            350                 355                 360 gcc aaa ggt gtt ggc ctc ggg ctt ggc ctg ggc ctc ggc gcc tgg ggg       1271
Ala Lys Gly Val Gly Leu Gly Leu Gly Leu Gly Leu Gly Ala Trp Gly
        365                 370                 375 ccg ttc gcc cta ggg gct atc ggc cta gcg ggt gtt gtc gcg ctt tat       1319
Pro Phe Ala Leu Gly Ala Ile Gly Leu Ala Gly Val Val Ala Leu Tyr
    380                 385                 390 acc tgg gcg cgc cgc cgc cat ggc gct ccc gat gtt tcc gat gat gca       1367
Thr Trp Ala Arg Arg Arg His Gly Ala Pro Asp Val Ser Asp Asp Ala
395                 400                 405 ttg ctg gcg gct gtc ggc gag gaa taa gcctgaccct tgaattcagg             1414
Leu Leu Ala Ala Val Gly Glu Glu
410                 415 acaacagcg atg agc ttt caa ctt gcg ccg tac ttg gcg aaa tcc gtc cct      1465
          Met Ser Phe Gln Leu Ala Pro Tyr Leu Ala Lys Ser Val Pro
              420                 425                 430 gga atc ggc att ctc ggc ggc att gtc ggt ggc gcc gcc gcc ctt gcc       1513
Gly Ile Gly Ile Leu Gly Gly Ile Val Gly Gly Ala Ala Ala Leu Ala
            435                 440                 445 aag aat gcc cgc ctt ttg aag gac aag cag ata acc ggc aca gaa gcg       1561
Lys Asn Ala Arg Leu Leu Lys Asp Lys Gln Ile Thr Gly Thr Glu Ala
        450                 455                 460 gcc atc gac acc ggc aag gaa gcc gcc ggt gcc ggg ctt gcc acc gct       1609
Ala Ile Asp Thr Gly Lys Glu Ala Ala Gly Ala Gly Leu Ala Thr Ala
    465                 470                 475 ttc tcc gcc gtc gcc gcc acc gcc gtc ggc ggt ggg ttg gtg gtc tcg       1657
Phe Ser Ala Val Ala Ala Thr Ala Val Gly Gly Gly Leu Val Val Ser
480                 485                 490                 495 ttg gga acc gcc cta atc gcc ggt gtc gcc gcc aaa tac gcc tgg gac       1705
Leu Gly Thr Ala Leu Ile Ala Gly Val Ala Ala Lys Tyr Ala Trp Asp
            500                 505                 510
```

```
ctg ggt gtc gat ttc atc gag aag gaa ttg cgt cac ggc aag tcc gcc      1753
Leu Gly Val Asp Phe Ile Glu Lys Glu Leu Arg His Gly Lys Ser Ala
            515                 520                 525 gag gcg aca gcg tcc gac gaa gac att ctg agg gaa gaa ttg gcc tga      1801
Glu Ala Thr Ala Ser Asp Glu Asp Ile Leu Arg Glu Glu Leu Ala
        530                 535                 540

<210> SEQ ID NO 4
<211> LENGTH: 1178
<212> TYPE: DNA
<213> ORGANISM: Artificial sequence
<220> FEATURE:
<223> OTHER INFORMATION: Fragment of the mamGFDC operon of M.
      gryphiswaldense ((delta)mamD)
<220> FEATURE:
<221> NAME/KEY: CDS
<222> LOCATION: (1)..(225)
<223> OTHER INFORMATION: Coding sequence of the mamG gene of M.
      gryphiswaldense
<220> FEATURE:
<221> NAME/KEY: CDS
<222> LOCATION: (270)..(605)
<223> OTHER INFORMATION: Coding sequence of the mamF gene of M.
      gryphiswaldense
<220> FEATURE:
<221> NAME/KEY: CDS
<222> LOCATION: (801)..(1178)
<223> OTHER INFORMATION: Coding sequence of the mamC gene of M.
      gryphiswaldense

<400> SEQUENCE: 4 atg atc aag ggc atc gcc ggc gtt ggc gga acc gcc ctt ggc gtc ggt       48
Met Ile Lys Gly Ile Ala Gly Val Gly Gly Thr Ala Leu Gly Val Gly
1               5                   10                  15 ggc gga gtt gcc gcc cct ccg gtc tct gcc gct gct gtc ggc agc acc      96
Gly Gly Val Ala Ala Pro Pro Val Ser Ala Ala Ala Val Gly Ser Thr
            20                  25                  30 ttg ctg gcc ggc aag ggg gtg tgc ctg ggg ctg ggg ctt ggc ctc ggt      144
Leu Leu Ala Gly Lys Gly Val Cys Leu Gly Leu Gly Leu Gly Leu Gly
        35                  40                  45 gct tgg ggt ccc gtt ctt ctc ggc gtt gcc gga ttg gct tgc gcc gcc      192
Ala Trp Gly Pro Val Leu Leu Gly Val Ala Gly Leu Ala Cys Ala Ala
    50                  55                  60 tcc cta tgt gat tat ctg aag aat cgc aaa gcg caggctgagg ccagcgctga   245
Ser Leu Cys Asp Tyr Leu Lys Asn Arg Lys Ala
65                  70                  75 gcctgcttaa gcgagggcaa agca atg gcc gag act att ttg atc gaa act      296
                          Met Ala Glu Thr Ile Leu Ile Glu Thr
                                            80 aaa aca gct ggc ggc aac tgc cgt tca tat ctg atg gcg ggc gct agc      344
Lys Thr Ala Gly Gly Asn Cys Arg Ser Tyr Leu Met Ala Gly Ala Ser
85                  90                  95                  100 tat ctg ggc atc ctc tgc ttc gtc ccg ctg ctt atg agc cgc gat gac      392
Tyr Leu Gly Ile Leu Cys Phe Val Pro Leu Leu Met Ser Arg Asp Asp
                105                 110                 115 gaa tat gtg tac ttc cat gcc aag cag ggg ctg gtg ctg tgg atg tgg      440
Glu Tyr Val Tyr Phe His Ala Lys Gln Gly Leu Val Leu Trp Met Trp
            120                 125                 130 agc atc ctg gcc atg ttc gcg ctg cat ctg ccg ggc atc ggc aag tgg      488
Ser Ile Leu Ala Met Phe Ala Leu His Leu Pro Gly Ile Gly Lys Trp
        135                 140                 145 ctc ttc ggc ttc tcg tcc atg ggc gtc ctg atg ctg tcc gtg gtc ggc      536
Leu Phe Gly Phe Ser Ser Met Gly Val Leu Met Leu Ser Val Val Gly
    150                 155                 160
```

```
ttg gtc tcg gtg gcg ctg cgc cgc acc tgg cgt ctg ccc ctt ata agc    584
Leu Val Ser Val Ala Leu Arg Arg Thr Trp Arg Leu Pro Leu Ile Ser
165                 170                 175                 180 cat gta gtc gcc ctg atc tga cggcgagcga tctaacggac ccggacagca       635
His Val Val Ala Leu Ile
            185 gcgcaagcac gcgaccggag tcctttgctt tggagtccca agcggcttct gccatgtagg  695 cgcagtttcg tctcaggaaa ggccaatacc atgcaggacc ttttctcgt tgctggcggc   755 tgtcggcgag gaataagcct gacccttgaa ttcaggacaa cagcg atg agc ttt caa  812
                                                  Met Ser Phe Gln
                                                      190 ctt gcg ccg tac ttg gcg aaa tcc gtc cct gga atc ggc att ctc ggc    860
Leu Ala Pro Tyr Leu Ala Lys Ser Val Pro Gly Ile Gly Ile Leu Gly
            195                 200                 205 ggc att gtc ggt ggc gcc gcc gcc ctt gcc aag aat gcc cgc ctt ttg    908
Gly Ile Val Gly Gly Ala Ala Ala Leu Ala Lys Asn Ala Arg Leu Leu
        210                 215                 220 aag gac aag cag ata acc ggc aca gaa gcg gcc atc gac acc ggc aag    956
Lys Asp Lys Gln Ile Thr Gly Thr Glu Ala Ala Ile Asp Thr Gly Lys
    225                 230                 235 gaa gcc gcc ggt gcc ggg ctt gcc acc gct ttc tcc gcc gtc gcc gcc    1004
Glu Ala Ala Gly Ala Gly Leu Ala Thr Ala Phe Ser Ala Val Ala Ala
240                 245                 250 acc gcc gtc ggc ggt ggg ttg gtg gtc tcg ttg gga acc gcc cta atc    1052
Thr Ala Val Gly Gly Gly Leu Val Val Ser Leu Gly Thr Ala Leu Ile
255                 260                 265                 270 gcc ggt gtc gcc gcc aaa tac gcc tgg gac ctg ggt gtc gat ttc atc    1100
Ala Gly Val Ala Ala Lys Tyr Ala Trp Asp Leu Gly Val Asp Phe Ile
                275                 280                 285 gag aag gaa ttg cgt cac ggc aag tcc gcc gag gcg aca gcg tcc gac    1148
Glu Lys Glu Leu Arg His Gly Lys Ser Ala Glu Ala Thr Ala Ser Asp
            290                 295                 300 gaa gac att ctg agg gaa gaa ttg gcc tga                            1178
Glu Asp Ile Leu Arg Glu Glu Leu Ala
        305                 310

<210> SEQ ID NO 5
<211> LENGTH: 1670
<212> TYPE: DNA
<213> ORGANISM: Artificial sequence
<220> FEATURE:
<223> OTHER INFORMATION: Fragment of the mamGFDC operon of M.
      gryphiswaldesnse ((delta)mamC)
<220> FEATURE:
<221> NAME/KEY: CDS
<222> LOCATION: (1)..(255)
<223> OTHER INFORMATION: Coding sequence of the mamG gene of M.
      gryphiswaldense
<220> FEATURE:
<221> NAME/KEY: CDS
<222> LOCATION: (270)..(605)
<223> OTHER INFORMATION: Coding sequence of the mamF gene of M.
      gryphiswaldense
<220> FEATURE:
<221> NAME/KEY: CDS
<222> LOCATION: (726)..(1670)
<223> OTHER INFORMATION: Coding sequence of the mamD gene of M.
      gryphiswaldense

<400> SEQUENCE: 5 atg atc aag ggc atc gcc ggc gtt ggc gga acc gcc ctt ggc gtc ggt    48
Met Ile Lys Gly Ile Ala Gly Val Gly Gly Thr Ala Leu Gly Val Gly
1               5                   10                  15
```

| | | | | | | | | | | | | | | | |
|---|---|---|---|---|---|---|---|---|---|---|---|---|---|---|---|
| ggc | gga | gtt | gcc | gcc | cct | ccg | gtc | tct | gcc | gct | gct | gtc | ggc | agc | acc | 96 |
| Gly | Gly | Val | Ala | Ala | Pro | Pro | Val | Ser | Ala | Ala | Ala | Val | Gly | Ser | Thr |
| | | | 20 | | | | 25 | | | | | 30 | | | |

| | | | | | | | | | | | | | | | |
|---|---|---|---|---|---|---|---|---|---|---|---|---|---|---|---|
| ttg | ctg | gcc | ggc | aag | ggg | gtg | tgc | ctg | ggg | ctg | ggg | ctt | ggc | ctc | ggt | 144 |
| Leu | Leu | Ala | Gly | Lys | Gly | Val | Cys | Leu | Gly | Leu | Gly | Leu | Gly | Leu | Gly |
| | | 35 | | | | | 40 | | | | | 45 | | | |

| | | | | | | | | | | | | | | | |
|---|---|---|---|---|---|---|---|---|---|---|---|---|---|---|---|
| gct | tgg | ggt | ccc | gtt | ctt | ctc | ggc | gtt | gcc | gga | ttg | gct | tgc | gcc | gcc | 192 |
| Ala | Trp | Gly | Pro | Val | Leu | Leu | Gly | Val | Ala | Gly | Leu | Ala | Cys | Ala | Ala |
| | 50 | | | | | 55 | | | | | 60 | | | | |

| | | | | | | | | | | | | | | | |
|---|---|---|---|---|---|---|---|---|---|---|---|---|---|---|---|
| tcc | cta | tgt | gat | tat | ctg | aag | aat | cgc | aaa | gcg | cag | gct | gag | gcc | agc | 240 |
| Ser | Leu | Cys | Asp | Tyr | Leu | Lys | Asn | Arg | Lys | Ala | Gln | Ala | Glu | Ala | Ser |
| 65 | | | | | 70 | | | | | 75 | | | | | 80 |

| | | | | | | | | | | | | |
|---|---|---|---|---|---|---|---|---|---|---|---|---|
| gct | gag | cct | gct | taa | gcgagggcaa | agca | atg | gcc | gag | act | att | ttg | atc | 290 |
| Ala | Glu | Pro | Ala | | | | Met | Ala | Glu | Thr | Ile | Leu | Ile |
| | | | | | | | 85 | | | | | 90 | |

| | | | | | | | | | | | | | | | |
|---|---|---|---|---|---|---|---|---|---|---|---|---|---|---|---|
| gaa | act | aaa | aca | gct | ggc | ggc | aac | tgc | cgt | tca | tat | ctg | atg | gcg | ggc | 338 |
| Glu | Thr | Lys | Thr | Ala | Gly | Gly | Asn | Cys | Arg | Ser | Tyr | Leu | Met | Ala | Gly |
| | | | 95 | | | | 100 | | | | | 105 | | | |

| | | | | | | | | | | | | | | | |
|---|---|---|---|---|---|---|---|---|---|---|---|---|---|---|---|
| gct | agc | tat | ctg | ggc | atc | ctc | tgc | ttc | gtc | ccg | ctg | ctt | atg | agc | cgc | 386 |
| Ala | Ser | Tyr | Leu | Gly | Ile | Leu | Cys | Phe | Val | Pro | Leu | Leu | Met | Ser | Arg |
| | | | 110 | | | | 115 | | | | | 120 | | | |

| | | | | | | | | | | | | | | | |
|---|---|---|---|---|---|---|---|---|---|---|---|---|---|---|---|
| gat | gac | gaa | tat | gtg | tac | ttc | cat | gcc | aag | cag | ggg | ctg | gtg | ctg | tgg | 434 |
| Asp | Asp | Glu | Tyr | Val | Tyr | Phe | His | Ala | Lys | Gln | Gly | Leu | Val | Leu | Trp |
| | | 125 | | | | | 130 | | | | | 135 | | | |

| | | | | | | | | | | | | | | | |
|---|---|---|---|---|---|---|---|---|---|---|---|---|---|---|---|
| atg | tgg | agc | atc | ctg | gcc | atg | ttc | gcg | ctg | cat | ctg | ccg | ggc | atc | ggc | 482 |
| Met | Trp | Ser | Ile | Leu | Ala | Met | Phe | Ala | Leu | His | Leu | Pro | Gly | Ile | Gly |
| 140 | | | | | 145 | | | | | 150 | | | | | 155 |

| | | | | | | | | | | | | | | | |
|---|---|---|---|---|---|---|---|---|---|---|---|---|---|---|---|
| aag | tgg | ctc | ttc | ggc | ttc | tcg | tcc | atg | ggc | gtc | ctg | atg | ctg | tcc | gtg | 530 |
| Lys | Trp | Leu | Phe | Gly | Phe | Ser | Ser | Met | Gly | Val | Leu | Met | Leu | Ser | Val |
| | | | | 160 | | | | | 165 | | | | | 170 | |

| | | | | | | | | | | | | | | | |
|---|---|---|---|---|---|---|---|---|---|---|---|---|---|---|---|
| gtc | ggc | ttg | gtc | tcg | gtg | gcg | ctg | cgc | cgc | acc | tgg | cgt | ctg | ccc | ctt | 578 |
| Val | Gly | Leu | Val | Ser | Val | Ala | Leu | Arg | Arg | Thr | Trp | Arg | Leu | Pro | Leu |
| | | | 175 | | | | | 180 | | | | | 185 | | |

| | | | | | | | |
|---|---|---|---|---|---|---|---|
| ata | agc | cat | gta | gtc | gcc | ctg | atc | tga | cggcgagcga | tctaacggac | 625 |
| Ile | Ser | His | Val | Val | Ala | Leu | Ile |
| | | 190 | | | | | 195 |

| | | | | | |
|---|---|---|---|---|---|
| ccggacagca | gcgcaagcac | gcgaccggag | tcctttgctt | tggagtccca | agcggcttct | 685 |

| | | | | | | |
|---|---|---|---|---|---|---|
| gccatgtagg | cgcagtttcg | tctcaggaaa | ggccaatacc | atg | cag | gac | ctt | ttt | 740 |
| | | | | Met | Gln | Asp | Leu | Phe |
| | | | | | | | | 200 |

| | | | | | | | | | | | | | | | |
|---|---|---|---|---|---|---|---|---|---|---|---|---|---|---|---|
| ctc | gcg | aag | gtc | gaa | agc | gcc | atg | cag | gcg | tcc | cag | gtc | ggg | gca | ctt | 788 |
| Leu | Ala | Lys | Val | Glu | Ser | Ala | Met | Gln | Ala | Ser | Gln | Val | Gly | Ala | Leu |
| | | | | 205 | | | | | 210 | | | | | 215 | |

| | | | | | | | | | | | | | | | |
|---|---|---|---|---|---|---|---|---|---|---|---|---|---|---|---|
| gcc | ggt | cag | acg | gcg | acg | gtc | tcg | tca | gtc | tcg | gcc | acg | acc | aat | ctg | 836 |
| Ala | Gly | Gln | Thr | Ala | Thr | Val | Ser | Ser | Val | Ser | Ala | Thr | Thr | Asn | Leu |
| | | | 220 | | | | | 225 | | | | | 230 | | |

| | | | | | | | | | | | | | | | |
|---|---|---|---|---|---|---|---|---|---|---|---|---|---|---|---|
| gcc | acc | ata | acc | cca | acc | acc | gcc | ggg | cag | gcc | cct | atc | atc | gtc | aaa | 884 |
| Ala | Thr | Ile | Thr | Pro | Thr | Thr | Ala | Gly | Gln | Ala | Pro | Ile | Ile | Val | Lys |
| | | 235 | | | | | 240 | | | | | 245 | | | |

| | | | | | | | | | | | | | | | |
|---|---|---|---|---|---|---|---|---|---|---|---|---|---|---|---|
| ctg | gac | gcg | gca | cgg | cag | gtg | acg | gag | ttg | cag | gcc | ctg | atg | gga | aag | 932 |
| Leu | Asp | Ala | Ala | Arg | Gln | Val | Thr | Glu | Leu | Gln | Ala | Leu | Met | Gly | Lys |
| | 250 | | | | | 255 | | | | | 260 | | | | |

| | | | | | | | | | | | | | | | |
|---|---|---|---|---|---|---|---|---|---|---|---|---|---|---|---|
| acc | gtg | ctg | gtc | gga | aag | acc | ccg | acc | acc | atc | ggc | ggc | atc | gga | aac | 980 |
| Thr | Val | Leu | Val | Gly | Lys | Thr | Pro | Thr | Thr | Ile | Gly | Gly | Ile | Gly | Asn |
| 265 | | | | | 270 | | | | | 275 | | | | | 280 |

| | | | | | | | | | | | | | | | |
|---|---|---|---|---|---|---|---|---|---|---|---|---|---|---|---|
| tgg | att | gcc | ttg | acc | ccg | gcg | gcg | gga | gcc | aag | acc | ggc | gct | gcc | gtg | 1028 |
| Trp | Ile | Ala | Leu | Thr | Pro | Ala | Ala | Gly | Ala | Lys | Thr | Gly | Ala | Ala | Val |
| | | | 285 | | | | | 290 | | | | | 295 | | |

```
gcc gga acc ggt cag ctt gtc atg atg aag gtc gag ggc acc ggc gcg       1076
Ala Gly Thr Gly Gln Leu Val Met Met Lys Val Glu Gly Thr Gly Ala
            300                 305                 310 gcc atc aag ctt ccc gcc ctg gcg ggt aag agc ttc atc gtc gcc cag       1124
Ala Ile Lys Leu Pro Ala Leu Ala Gly Lys Ser Phe Ile Val Ala Gln
        315                 320                 325 ccc ccc gta gcc gcc gga acc aaa gcg gcg ggc atg ctc tat ctg aat       1172
Pro Pro Val Ala Ala Gly Thr Lys Ala Ala Gly Met Leu Tyr Leu Asn
    330                 335                 340 ccg gtt ggc ggt ggt gat atg gtg gcc atc aac att cag aac gcc atg       1220
Pro Val Gly Gly Gly Asp Met Val Ala Ile Asn Ile Gln Asn Ala Met
345                 350                 355                 360 acc cag acc ggc ggc ttg gtc ggc aag acc ttc acc gtc gcc ccc agc       1268
Thr Gln Thr Gly Gly Leu Val Gly Lys Thr Phe Thr Val Ala Pro Ser
                365                 370                 375 ccc gtc att ggc ggc acc acc ggt aaa ttc ctg gtc ctg aag ccc atg       1316
Pro Val Ile Gly Gly Thr Thr Gly Lys Phe Leu Val Leu Lys Pro Met
            380                 385                 390 gcg acc ggg gtc ggc aag gcg gtg ggc agc ggc gcc gtc gtc gcc aag       1364
Ala Thr Gly Val Gly Lys Ala Val Gly Ser Gly Ala Val Val Ala Lys
        395                 400                 405 ttc gta ccc gcc gcc gtc acc ggc acg ggc gga gcg gcg gct atc ggg       1412
Phe Val Pro Ala Ala Val Thr Gly Thr Gly Gly Ala Ala Ala Ile Gly
    410                 415                 420 gcc gga tcc gcc acc acc ctg atg gcc acg ggc gcc agt acg atc acc       1460
Ala Gly Ser Ala Thr Thr Leu Met Ala Thr Gly Ala Ser Thr Ile Thr
425                 430                 435                 440 ccc gtc act gcc gcc gcc gct ggc agc gcc atg ctg aca gcc aaa ggt       1508
Pro Val Thr Ala Ala Ala Ala Gly Ser Ala Met Leu Thr Ala Lys Gly
                445                 450                 455 gtt ggc ctc ggg ctt ggc ctg ggc ctc ggc gcc tgg ggg ccg ttc gcc       1556
Val Gly Leu Gly Leu Gly Leu Gly Leu Gly Ala Trp Gly Pro Phe Ala
            460                 465                 470 cta ggg gct atc ggc cta gcg ggt gtt gtc gcg ctt tat acc tgg gcg       1604
Leu Gly Ala Ile Gly Leu Ala Gly Val Val Ala Leu Tyr Thr Trp Ala
        475                 480                 485 cgc cgc cgc cat ggc gct ccc gat gtt tcc gat gat gca ttg ctg gcg       1652
Arg Arg Arg His Gly Ala Pro Asp Val Ser Asp Asp Ala Leu Leu Ala
    490                 495                 500 gct gtc ggc gag gaa taa                                               1670
Ala Val Gly Glu Glu
505

<210> SEQ ID NO 6
<211> LENGTH: 1516
<212> TYPE: DNA
<213> ORGANISM: Artificial sequence
<220> FEATURE:
<223> OTHER INFORMATION: Fragment of the mamGFDC operon of M.
      gryphiswaldense ((delta)mamGF)
<220> FEATURE:
<221> NAME/KEY: CDS
<222> LOCATION: (1)..(21)
<223> OTHER INFORMATION: Remnant coding sequence of the mamG gene of M.
      gryphiswaldense
<220> FEATURE:
<221> NAME/KEY: CDS
<222> LOCATION: (165)..(1109)
<223> OTHER INFORMATION: Coding sequence of the mamD gene of M.
      gryphiswaldense
<220> FEATURE:
<221> NAME/KEY: CDS
<222> LOCATION: (1139)..(1516)
<223> OTHER INFORMATION: Coding sequence of the mamC gene of M.
      gryphiswaldense
```

```
<400> SEQUENCE: 6 atg atc aag ggc atc gcc taa gccatgtagt cgccctgatc tgacggcgag        51
Met Ile Lys Gly Ile Ala
 1               5 cgatctaacg gacccggaca gcagcgcaag cacgcgaccg gagtcctttg ctttggagtc   111
ccaagcggct tctgccatgt aggcgcagtt tcgtctcagg aaaggccaat acc atg      167
                                                             Met cag gac ctt ttt ctc gcg aag gtc gaa agc gcc atg cag gcg tcc cag    215
Gln Asp Leu Phe Leu Ala Lys Val Glu Ser Ala Met Gln Ala Ser Gln
         10              15                  20 gtc ggg gca ctt gcc ggt cag acg gcg acg gtc tcg tca gtc tcg gcc    263
Val Gly Ala Leu Ala Gly Gln Thr Ala Thr Val Ser Ser Val Ser Ala
     25                  30                  35 acg acc aat ctg gcc acc ata acc cca acc acc gcc ggg cag gcc cct    311
Thr Thr Asn Leu Ala Thr Ile Thr Pro Thr Thr Ala Gly Gln Ala Pro
 40                  45                  50                  55 atc atc gtc aaa ctg gac gcg gca cgg cag gtg acg gag ttg cag gcc    359
Ile Ile Val Lys Leu Asp Ala Ala Arg Gln Val Thr Glu Leu Gln Ala
                     60                  65                  70 ctg atg gga aag acc gtg ctg gtc gga aag acc ccg acc acc atc ggc    407
Leu Met Gly Lys Thr Val Leu Val Gly Lys Thr Pro Thr Thr Ile Gly
                 75                  80                  85 ggc atc gga aac tgg att gcc ttg acc ccg gcg gcg gga gcc aag acc    455
Gly Ile Gly Asn Trp Ile Ala Leu Thr Pro Ala Ala Gly Ala Lys Thr
             90                  95                 100 ggc gct gcc gtg gcc gga acc ggt cag ctt gtc atg atg aag gtc gag    503
Gly Ala Ala Val Ala Gly Thr Gly Gln Leu Val Met Met Lys Val Glu
105                 110                 115 ggc acc ggc gcg gcc atc aag ctt ccc gcc ctg gcg ggt aag agc ttc    551
Gly Thr Gly Ala Ala Ile Lys Leu Pro Ala Leu Ala Gly Lys Ser Phe
120                 125                 130                 135 atc gtc gcc cag ccc ccc gta gcc gcc gga acc aaa gcg gcg ggc atg    599
Ile Val Ala Gln Pro Pro Val Ala Ala Gly Thr Lys Ala Ala Gly Met
                140                 145                 150 ctc tat ctg aat ccg gtt ggc ggt ggt gat atg gtg gcc atc aac att    647
Leu Tyr Leu Asn Pro Val Gly Gly Gly Asp Met Val Ala Ile Asn Ile
            155                 160                 165 cag aac gcc atg acc cag acc ggc ggc ttg gtc ggc aag acc ttc acc    695
Gln Asn Ala Met Thr Gln Thr Gly Gly Leu Val Gly Lys Thr Phe Thr
        170                 175                 180 gtc gcc ccc agc ccc gtc att ggc ggc acc acc ggt aaa ttc ctg gtc    743
Val Ala Pro Ser Pro Val Ile Gly Gly Thr Thr Gly Lys Phe Leu Val
    185                 190                 195 ctg aag ccc atg gcg acc ggg gtc ggc aag gcg gtg ggc agc ggc gcc    791
Leu Lys Pro Met Ala Thr Gly Val Gly Lys Ala Val Gly Ser Gly Ala
200                 205                 210                 215 gtc gtc gcc aag ttc gta ccc gcc gcc gtc acc ggc acg ggc gga gcg    839
Val Val Ala Lys Phe Val Pro Ala Ala Val Thr Gly Thr Gly Gly Ala
                220                 225                 230 gcg gct atc ggg gcc gga tcc gcc acc acc ctg atg gcc acg ggc gcc    887
Ala Ala Ile Gly Ala Gly Ser Ala Thr Thr Leu Met Ala Thr Gly Ala
            235                 240                 245 agt acg atc acc ccc gtc act gcc gcc gct ggc agc gcc atg ctg        935
Ser Thr Ile Thr Pro Val Thr Ala Ala Ala Gly Ser Ala Met Leu
        250                 255                 260 aca gcc aaa ggt gtt ggc ctc ggg ctt ggc ctg ggc ctc ggc gcc tgg    983
Thr Ala Lys Gly Val Gly Leu Gly Leu Gly Leu Gly Leu Gly Ala Trp
    265                 270                 275
```

```
ggg ccg ttc gcc cta ggg gct atc ggc cta gcg ggt gtt gtc gcg ctt    1031
Gly Pro Phe Ala Leu Gly Ala Ile Gly Leu Ala Gly Val Val Ala Leu
280                 285                 290                 295 tat acc tgg gcg cgc cgc cat ggc gct ccc gat gtt tcc gat gat        1079
Tyr Thr Trp Ala Arg Arg Arg His Gly Ala Pro Asp Val Ser Asp Asp
                300                 305                 310 gca ttg ctg gcg gct gtc ggc gag gaa taa gcctgaccct tgaattcagg      1129
Ala Leu Leu Ala Ala Val Gly Glu Glu
            315                 320 acaacagcg atg agc ttt caa ctt gcg ccg tac ttg gcg aaa tcc gtc cct  1180
          Met Ser Phe Gln Leu Ala Pro Tyr Leu Ala Lys Ser Val Pro
              325                 330 gga atc ggc att ctc ggc ggc att gtc ggt ggc gcc gcc gcc ctt gcc    1228
Gly Ile Gly Ile Leu Gly Gly Ile Val Gly Gly Ala Ala Ala Leu Ala
335                 340                 345                 350 aag aat gcc cgc ctt ttg aag gac aag cag ata acc ggc aca gaa gcg    1276
Lys Asn Ala Arg Leu Leu Lys Asp Lys Gln Ile Thr Gly Thr Glu Ala
                355                 360                 365 gcc atc gac acc ggc aag gaa gcc gcc ggt gcc ggg ctt gcc acc gct    1324
Ala Ile Asp Thr Gly Lys Glu Ala Ala Gly Ala Gly Leu Ala Thr Ala
            370                 375                 380 ttc tcc gcc gtc gcc gcc acc gcc gtc ggc ggt ggg ttg gtg gtc tcg    1372
Phe Ser Ala Val Ala Ala Thr Ala Val Gly Gly Gly Leu Val Val Ser
385                 390                 395 ttg gga acc gcc cta atc gcc ggt gtc gcc gcc aaa tac gcc tgg gac    1420
Leu Gly Thr Ala Leu Ile Ala Gly Val Ala Ala Lys Tyr Ala Trp Asp
400                 405                 410 ctg ggt gtc gat ttc atc gag aag gaa ttg cgt cac ggc aag tcc gcc    1468
Leu Gly Val Asp Phe Ile Glu Lys Glu Leu Arg His Gly Lys Ser Ala
415                 420                 425                 430 gag gcg aca gcg tcc gac gaa gac att ctg agg gaa gaa ttg gcc tga    1516
Glu Ala Thr Ala Ser Asp Glu Asp Ile Leu Arg Glu Glu Leu Ala
                435                 440                 445

<210> SEQ ID NO 7
<211> LENGTH: 960
<212> TYPE: DNA
<213> ORGANISM: Artificial sequence
<220> FEATURE:
<223> OTHER INFORMATION: Fragment of the mamGFDC operon of M.
      gryphiswaldense ((delta)mamFD)
<220> FEATURE:
<221> NAME/KEY: CDS
<222> LOCATION: (1)..(255)
<223> OTHER INFORMATION: Coding sequence of the mamG gene of M.
      gryphiswaldense
<220> FEATURE:
<221> NAME/KEY: CDS
<222> LOCATION: (583)..(960)
<223> OTHER INFORMATION: Coding sequence of the mamC gene of M.
      gryphiswaldense

<400> SEQUENCE: 7 atg atc aag ggc atc gcc ggc gtt ggc gga acc gcc ctt ggc gtc ggt    48
Met Ile Lys Gly Ile Ala Gly Val Gly Gly Thr Ala Leu Gly Val Gly
1               5                   10                  15 ggc gga gtt gcc gcc cct ccg gtc tct gcc gct gct gtc ggc agc acc    96
Gly Gly Val Ala Ala Pro Pro Val Ser Ala Ala Ala Val Gly Ser Thr
                20                  25                  30 ttg ctg gcc ggc aag ggg gtg tgc ctg ggg ctg ggg ctt ggc ctc ggt    144
Leu Leu Ala Gly Lys Gly Val Cys Leu Gly Leu Gly Leu Gly Leu Gly
            35                  40                  45 gct tgg ggt ccc gtt ctt ctc ggc gtt gcc gga ttg gct tgc gcc gcc    192
Ala Trp Gly Pro Val Leu Leu Gly Val Ala Gly Leu Ala Cys Ala Ala
50                  55                  60
```

```
tcc cta tgt gat tat ctg aag aat cgc aaa gcg cag gct gag gcc agc        240
Ser Leu Cys Asp Tyr Leu Lys Asn Arg Lys Ala Gln Ala Glu Ala Ser
65                  70                  75                  80 gct gag cct gct taa gcgagggcaa agcaatggcc gagactattt tgatcgaaac        295
Ala Glu Pro Ala taaaacagcg ccaccaccct gatggccacg ggcgccagta cgatcacccc cgtcactgcc      355
gccgccgctg gcagcgccat gctgacagcc aaaggtgttg gcctcgggct tggcctgggc      415
ctcggcgcct gggggccgtt cgccctaggg gctatcggcc tagcgggtgt tgtcgcgctt      475
tatacctggg cgcgccgccg ccatggcgct cccgatgttt ccgatgatgc attgctggcg      535
gctgtcggcg aggaataagc ctgacccttg aattcaggac aacagcg atg agc ttt        591
                                                    Met Ser Phe
                                                         85 caa ctt gcg ccg tac ttg gcg aaa tcc gtc cct gga atc ggc att ctc        639
Gln Leu Ala Pro Tyr Leu Ala Lys Ser Val Pro Gly Ile Gly Ile Leu
            90                  95                  100 ggc ggc att gtc ggt ggc gcc gcc gcc ctt gcc aag aat gcc cgc ctt        687
Gly Gly Ile Val Gly Gly Ala Ala Ala Leu Ala Lys Asn Ala Arg Leu
        105                 110                 115 ttg aag gac aag cag ata acc ggc aca gaa gcg gcc atc gac acc ggc        735
Leu Lys Asp Lys Gln Ile Thr Gly Thr Glu Ala Ala Ile Asp Thr Gly
120                 125                 130                 135 aag gaa gcc gcc ggt gcc ggg ctt gcc acc gct ttc tcc gcc gtc gcc        783
Lys Glu Ala Ala Gly Ala Gly Leu Ala Thr Ala Phe Ser Ala Val Ala
                140                 145                 150 gcc acc gcc gtc ggc ggt ggg ttg gtg gtc tcg ttg gga acc gcc cta        831
Ala Thr Ala Val Gly Gly Gly Leu Val Val Ser Leu Gly Thr Ala Leu
            155                 160                 165 atc gcc ggt gtc gcc gcc aaa tac gcc tgg gac ctg ggt gtc gat ttc        879
Ile Ala Gly Val Ala Ala Lys Tyr Ala Trp Asp Leu Gly Val Asp Phe
        170                 175                 180 atc gag aag gaa ttg cgt cac ggc aag tcc gcc gag gcg aca gcg tcc        927
Ile Glu Lys Glu Leu Arg His Gly Lys Ser Ala Glu Ala Thr Ala Ser
    185                 190                 195 gac gaa gac att ctg agg gaa gaa ttg gcc tga                            960
Asp Glu Asp Ile Leu Arg Glu Glu Leu Ala
200                 205

<210> SEQ ID NO 8
<211> LENGTH: 1393
<212> TYPE: DNA
<213> ORGANISM: Artificial sequence
<220> FEATURE:
<223> OTHER INFORMATION: Fragment of the mamGFDC operon of M.
      gryphiswaldense ((delta)mamFC)
<220> FEATURE:
<221> NAME/KEY: CDS
<222> LOCATION: (1)..(255)
<223> OTHER INFORMATION: Coding sequence of the mamG gene of M.
      gryphiswaldense
<220> FEATURE:
<221> NAME/KEY: CDS
<222> LOCATION: (270)..(305)
<223> OTHER INFORMATION: Remnant coding sequence of the mamF gene of M.
      gryphiswaldense
<220> FEATURE:
<221> NAME/KEY: CDS
<222> LOCATION: (449)..(1393)
<223> OTHER INFORMATION: Coding sequence of the mamD gene of M.
      gryphiswaldense

<400> SEQUENCE: 8 atg atc aag ggc atc gcc ggc gtt ggc gga acc gcc ctt ggc gtc ggt         48
Met Ile Lys Gly Ile Ala Gly Val Gly Gly Thr Ala Leu Gly Val Gly
1               5                   10                  15
```

|  |  |
|---|---|
| ggc gga gtt gcc gcc cct ccg gtc tct gcc gct gct gtc ggc agc acc<br>Gly Gly Val Ala Ala Pro Pro Val Ser Ala Ala Ala Val Gly Ser Thr<br>            20                      25                      30 | 96 |
| ttg ctg gcc ggc aag ggg gtg tgc ctg ggg ctg ggg ctt ggc ctc ggt<br>Leu Leu Ala Gly Lys Gly Val Cys Leu Gly Leu Gly Leu Gly Leu Gly<br>        35                      40                      45 | 144 |
| gct tgg ggt ccc gtt ctt ctc ggc gtt gcc gga ttg gct tgc gcc gcc<br>Ala Trp Gly Pro Val Leu Leu Gly Val Ala Gly Leu Ala Cys Ala Ala<br>    50                      55                      60 | 192 |
| tcc cta tgt gat tat ctg aag aat cgc aaa gcg cag gct gag gcc agc<br>Ser Leu Cys Asp Tyr Leu Lys Asn Arg Lys Ala Gln Ala Glu Ala Ser<br>65                      70                      75                      80 | 240 |
| gct gag cct gct taa gcgagggcaa agca atg gcc gag act att ttg atc<br>Ala Glu Pro Ala                         Met Ala Glu Thr Ile Leu Ile<br>                                                    85                      90 | 290 |
| gaa act aaa aca taa gccatgtagt cgccctgatc tgacggcgag cgatctaacg<br>Glu Thr Lys Thr<br>95 | 345 |
| gacccggaca gcagcgcaag cacgcgaccg gagtcctttg ctttggagtc ccaagcggct | 405 |
| tctgccatgt aggcgcagtt tcgtctcagg aaaggccaat acc atg cag gac ctt<br>                                                                Met Gln Asp Leu | 460 |
| ttt ctc gcg aag gtc gaa agc gcc atg cag gcg tcc cag gtc ggg gca<br>Phe Leu Ala Lys Val Glu Ser Ala Met Gln Ala Ser Gln Val Gly Ala<br>100                      105                      110                      115 | 508 |
| ctt gcc ggt cag acg gcg acg gtc tcg tca gtc tcg gcc acg acc aat<br>Leu Ala Gly Gln Thr Ala Thr Val Ser Ser Val Ser Ala Thr Thr Asn<br>                    120                      125                      130 | 556 |
| ctg gcc acc ata acc cca acc acc gcc ggg cag gcc cct atc atc gtc<br>Leu Ala Thr Ile Thr Pro Thr Thr Ala Gly Gln Ala Pro Ile Ile Val<br>                135                      140                      145 | 604 |
| aaa ctg gac gcg gca cgg cag gtg acg gag ttg cag gcc ctg atg gga<br>Lys Leu Asp Ala Ala Arg Gln Val Thr Glu Leu Gln Ala Leu Met Gly<br>150                      155                      160 | 652 |
| aag acc gtg ctg gtc gga aag acc ccg acc acc atc ggc ggc atc gga<br>Lys Thr Val Leu Val Gly Lys Thr Pro Thr Thr Ile Gly Gly Ile Gly<br>        165                      170                      175 | 700 |
| aac tgg att gcc ttg acc ccg gcg gcg gga gcc aag acc ggc gct gcc<br>Asn Trp Ile Ala Leu Thr Pro Ala Ala Gly Ala Lys Thr Gly Ala Ala<br>180                      185                      190                      195 | 748 |
| gtg gcc gga acc ggt cag ctt gtc atg atg aag gtc gag ggc acc ggc<br>Val Ala Gly Thr Gly Gln Leu Val Met Met Lys Val Glu Gly Thr Gly<br>                    200                      205                      210 | 796 |
| gcg gcc atc aag ctt ccc gcc ctg gcg ggt aag agc ttc atc gtc gcc<br>Ala Ala Ile Lys Leu Pro Ala Leu Ala Gly Lys Ser Phe Ile Val Ala<br>                215                      220                      225 | 844 |
| cag ccc ccc gta gcc gcc gga acc aaa gcg gcg ggc atg ctc tat ctg<br>Gln Pro Pro Val Ala Ala Gly Thr Lys Ala Ala Gly Met Leu Tyr Leu<br>        230                      235                      240 | 892 |
| aat ccg gtt ggc ggt ggt gat atg gtg gcc atc aac att cag aac gcc<br>Asn Pro Val Gly Gly Gly Asp Met Val Ala Ile Asn Ile Gln Asn Ala<br>    245                      250                      255 | 940 |
| atg acc cag acc ggc ggc ttg gtc ggc aag acc ttc acc gtc gcc ccc<br>Met Thr Gln Thr Gly Gly Leu Val Gly Lys Thr Phe Thr Val Ala Pro<br>260                      265                      270                      275 | 988 |
| agc ccc gtc att ggc ggc acc acc ggt aaa ttc ctg gtc ctg aag ccc<br>Ser Pro Val Ile Gly Gly Thr Thr Gly Lys Phe Leu Val Leu Lys Pro<br>                    280                      285                      290 | 1036 |
| atg gcg acc ggg gtc ggc aag gcg gtg ggc agc ggc gcc gtc gtc gcc<br>Met Ala Thr Gly Val Gly Lys Ala Val Gly Ser Gly Ala Val Val Ala<br>                    295                      300                      305 | 1084 |

-continued

| | | | | | | | | | | | | | | |
|---|---|---|---|---|---|---|---|---|---|---|---|---|---|---|
| aag | ttc | gta | ccc | gcc | gcc | gtc | acc | ggc | acg | ggc | gga | gcg | gcg | gct atc | 1132 |
| Lys | Phe | Val | Pro | Ala | Ala | Val | Thr | Gly | Thr | Gly | Gly | Ala | Ala | Ala Ile |
| | | 310 | | | | | 315 | | | | | 320 | | |

| ggg | gcc | gga | tcc | gcc | acc | acc | ctg | atg | gcc | acg | ggc | gcc | agt | acg atc | 1180 |
| Gly | Ala | Gly | Ser | Ala | Thr | Thr | Leu | Met | Ala | Thr | Gly | Ala | Ser | Thr Ile |
| 325 | | | | | 330 | | | | | 335 | | | | |

| acc | ccc | gtc | act | gcc | gcc | gcc | gct | ggc | agc | gcc | atg | ctg | aca | gcc aaa | 1228 |
| Thr | Pro | Val | Thr | Ala | Ala | Ala | Ala | Gly | Ser | Ala | Met | Leu | Thr | Ala Lys |
| 340 | | | | 345 | | | | | 350 | | | | | 355 |

| ggt | gtt | ggc | ctc | ggg | ctt | ggc | ctg | ggc | ctc | ggc | gcc | tgg | ggg | ccg ttc | 1276 |
| Gly | Val | Gly | Leu | Gly | Leu | Gly | Leu | Gly | Leu | Gly | Ala | Trp | Gly | Pro Phe |
| | | | | 360 | | | | | 365 | | | | | 370 |

| gcc | cta | ggg | gct | atc | ggc | cta | gcg | ggt | gtt | gtc | gcg | ctt | tat | acc tgg | 1324 |
| Ala | Leu | Gly | Ala | Ile | Gly | Leu | Ala | Gly | Val | Val | Ala | Leu | Tyr | Thr Trp |
| | | | 375 | | | | 380 | | | | | 385 | | |

| gcg | cgc | cgc | cgc | cat | ggc | gct | ccc | gat | gtt | tcc | gat | gat | gca | ttg ctg | 1372 |
| Ala | Arg | Arg | Arg | His | Gly | Ala | Pro | Asp | Val | Ser | Asp | Asp | Ala | Leu Leu |
| | | | 390 | | | | | 395 | | | | | 400 | |

| gcg | gct | gtc | ggc | gag | gaa | taa | | | | | | | | | 1393 |
| Ala | Ala | Val | Gly | Glu | Glu | | | | | | | | | | |
| 405 | | | | | | | | | | | | | | | |

<210> SEQ ID NO 9
<211> LENGTH: 1448
<212> TYPE: DNA
<213> ORGANISM: Artificial sequence
<220> FEATURE:
<223> OTHER INFORMATION: Fragment of the mamGFDC operon of M.
      gryphiswaldense ((delta)mamGC)
<220> FEATURE:
<221> NAME/KEY: CDS
<222> LOCATION: (1)..(33)
<223> OTHER INFORMATION: Remnant coding sequence of the mamG gene of M.
      gryphiswaldense
<220> FEATURE:
<221> NAME/KEY: CDS
<222> LOCATION: (48)..(383)
<223> OTHER INFORMATION: Coding sequence of the mamF gene of M.
      gryphiswaldense
<220> FEATURE:
<221> NAME/KEY: CDS
<222> LOCATION: (504)..(1448)
<223> OTHER INFORMATION: Coding sequence of the mamD gene of M.
      gryphiswaldense

<400> SEQUENCE: 9

| atg | atc | aag | ggc | atc | gcc | gct | gag | cct | gct | taa | gcgagggcaa | agca | atg | 50 |
|---|---|---|---|---|---|---|---|---|---|---|---|---|---|---|
| Met | Ile | Lys | Gly | Ile | Ala | Ala | Glu | Pro | Ala | | | | Met |
| 1 | | | 5 | | | | | 10 | | | | | |

| gcc | gag | act | att | ttg | atc | gaa | act | aaa | aca | gct | ggc | ggc | aac | tgc cgt | 98 |
| Ala | Glu | Thr | Ile | Leu | Ile | Glu | Thr | Lys | Thr | Ala | Gly | Gly | Asn | Cys Arg |
| | | | 15 | | | | | 20 | | | | | 25 | |

| tca | tat | ctg | atg | gcg | ggc | gct | agc | tat | ctg | ggc | atc | ctc | tgc | ttc gtc | 146 |
| Ser | Tyr | Leu | Met | Ala | Gly | Ala | Ser | Tyr | Leu | Gly | Ile | Leu | Cys | Phe Val |
| | | 30 | | | | | 35 | | | | | 40 | | |

| ccg | ctg | ctt | atg | agc | cgc | gat | gac | gaa | tat | gtg | tac | ttc | cat | gcc aag | 194 |
| Pro | Leu | Leu | Met | Ser | Arg | Asp | Asp | Glu | Tyr | Val | Tyr | Phe | His | Ala Lys |
| 45 | | | | | 50 | | | | | 55 | | | | |

| cag | ggg | ctg | gtg | ctg | tgg | atg | tgg | agc | atc | ctg | gcc | atg | ttc | gcg ctg | 242 |
| Gln | Gly | Leu | Val | Leu | Trp | Met | Trp | Ser | Ile | Leu | Ala | Met | Phe | Ala Leu |
| 60 | | | | 65 | | | | | 70 | | | | | 75 |

| cat | ctg | ccg | ggc | atc | ggc | aag | tgg | ctc | ttc | ggc | ttc | tcg | tcc | atg ggc | 290 |
| His | Leu | Pro | Gly | Ile | Gly | Lys | Trp | Leu | Phe | Gly | Phe | Ser | Ser | Met Gly |
| | | | | 80 | | | | | 85 | | | | | 90 |

```
gtc ctg atg ctg tcc gtg gtc ggc ttg gtc tcg gtg gcg ctg cgc cgc       338
Val Leu Met Leu Ser Val Val Gly Leu Val Ser Val Ala Leu Arg Arg
            95                  100                 105 acc tgg cgt ctg ccc ctt ata agc cat gta gtc gcc ctg atc tga           383
Thr Trp Arg Leu Pro Leu Ile Ser His Val Val Ala Leu Ile
        110                 115                 120 cggcgagcga tctaacggac ccggacagca gcgcaagcac gcgaccggag tcctttgctt     443
tggagtccca agcggcttct gccatgtagg cgcagtttcg tctcaggaaa ggccaatacc     503 atg cag gac ctt ttt ctc gcg aag gtc gaa agc gcc atg cag gcg tcc       551
Met Gln Asp Leu Phe Leu Ala Lys Val Glu Ser Ala Met Gln Ala Ser
                125                 130                 135 cag gtc ggg gca ctt gcc ggt cag acg gcg acg gtc tcg tca gtc tcg       599
Gln Val Gly Ala Leu Ala Gly Gln Thr Ala Thr Val Ser Ser Val Ser
        140                 145                 150 gcc acg acc aat ctg gcc acc ata acc cca acc acc gcc ggg cag gcc       647
Ala Thr Thr Asn Leu Ala Thr Ile Thr Pro Thr Thr Ala Gly Gln Ala
    155                 160                 165 cct atc atc gtc aaa ctg gac gcg gca cgg cag gtg acg gag ttg cag       695
Pro Ile Ile Val Lys Leu Asp Ala Ala Arg Gln Val Thr Glu Leu Gln
170                 175                 180                 185 gcc ctg atg gga aag acc gtg ctg gtc gga aag acc ccg acc acc atc       743
Ala Leu Met Gly Lys Thr Val Leu Val Gly Lys Thr Pro Thr Thr Ile
                190                 195                 200 ggc ggc atc gga aac tgg att gcc ttg acc ccg gcg gcg gga gcc aag       791
Gly Gly Ile Gly Asn Trp Ile Ala Leu Thr Pro Ala Ala Gly Ala Lys
            205                 210                 215 acc ggc gct gcc gtg gcc gga acc ggt cag ctt gtc atg atg aag gtc       839
Thr Gly Ala Ala Val Ala Gly Thr Gly Gln Leu Val Met Met Lys Val
        220                 225                 230 gag ggc acc ggc gcg gcc atc aag ctt ccc gcc ctg gcg ggt aag agc       887
Glu Gly Thr Gly Ala Ala Ile Lys Leu Pro Ala Leu Ala Gly Lys Ser
235                 240                 245 ttc atc gtc gcc cag ccc ccc gta gcc gcc gga acc aaa gcg gcg ggc       935
Phe Ile Val Ala Gln Pro Pro Val Ala Ala Gly Thr Lys Ala Ala Gly
250                 255                 260                 265 atg ctc tat ctg aat ccg gtt ggc ggt ggt gat atg gtg gcc atc aac       983
Met Leu Tyr Leu Asn Pro Val Gly Gly Gly Asp Met Val Ala Ile Asn
                270                 275                 280 att cag aac gcc atg acc cag acc ggc ggc ttg gtc ggc aag acc ttc      1031
Ile Gln Asn Ala Met Thr Gln Thr Gly Gly Leu Val Gly Lys Thr Phe
            285                 290                 295 acc gtc gcc ccc agc ccc gtc att ggc ggc acc acc ggt aaa ttc ctg      1079
Thr Val Ala Pro Ser Pro Val Ile Gly Gly Thr Thr Gly Lys Phe Leu
        300                 305                 310 gtc ctg aag ccc atg gcg acc ggg gtc ggc aag gcg gtg ggc agc ggc      1127
Val Leu Lys Pro Met Ala Thr Gly Val Gly Lys Ala Val Gly Ser Gly
    315                 320                 325 gcc gtc gtc gcc aag ttc gta ccc gcc gcc gtc acc ggc acg ggc gga      1175
Ala Val Val Ala Lys Phe Val Pro Ala Ala Val Thr Gly Thr Gly Gly
330                 335                 340                 345 gcg gcg gct atc ggg gcc gga tcc gcc acc acc ctg atg gcc acg ggc      1223
Ala Ala Ala Ile Gly Ala Gly Ser Ala Thr Thr Leu Met Ala Thr Gly
                350                 355                 360 gcc agt acg atc acc ccc gtc act gcc gcc gcc gct ggc agc gcc atg      1271
Ala Ser Thr Ile Thr Pro Val Thr Ala Ala Ala Ala Gly Ser Ala Met
            365                 370                 375 ctg aca gcc aaa ggt gtt ggc ctc ggg ctt ggc ctg ggc ctc ggc gcc      1319
Leu Thr Ala Lys Gly Val Gly Leu Gly Leu Gly Leu Gly Leu Gly Ala
        380                 385                 390
```

```
tgg ggg ccg ttc gcc cta ggg gct atc ggc cta gcg ggt gtt gtc gcg    1367
Trp Gly Pro Phe Ala Leu Gly Ala Ile Gly Leu Ala Gly Val Val Ala
    395                 400                 405 ctt tat acc tgg gcg cgc cgc cgc cat ggc gct ccc gat gtt tcc gat    1415
Leu Tyr Thr Trp Ala Arg Arg Arg His Gly Ala Pro Asp Val Ser Asp
410                 415                 420                 425 gat gca ttg ctg gcg gct gtc ggc gag gaa taa                        1448
Asp Ala Leu Leu Ala Ala Val Gly Glu Glu
                430                 435

<210> SEQ ID NO 10
<211> LENGTH: 1179
<212> TYPE: DNA
<213> ORGANISM: Artificial sequence
<220> FEATURE:
<223> OTHER INFORMATION: Fragment of the mamGFDC operon of M.
      gryphiswaldense ((delta)mamGD)
<220> FEATURE:
<221> NAME/KEY: CDS
<222> LOCATION: (1)..(33)
<223> OTHER INFORMATION: Remnant coding sequence of the mamG gene of M.
      gryphiswaldense
<220> FEATURE:
<221> NAME/KEY: CDS
<222> LOCATION: (48)..(383)
<223> OTHER INFORMATION: Coding sequence of the mamF gene of M.
      gryphiswaldense
<220> FEATURE:
<221> NAME/KEY: CDS
<222> LOCATION: (504)..(536)
<223> OTHER INFORMATION: Remnant coding sequence of the mamD gene of the
      M. gryphiswaldense
<220> FEATURE:
<221> NAME/KEY: CDS
<222> LOCATION: (802)..(1179)
<223> OTHER INFORMATION: Coding sequence of the mamC gene of the M.
      gryphiswaldense

<400> SEQUENCE: 10 atg atc aag ggc atc gcc gct gag cct gct taa gcgagggcaa agca atg    50
Met Ile Lys Gly Ile Ala Ala Glu Pro Ala                     Met
1               5                   10 gcc gag act att ttg atc gaa act aaa aca gct ggc ggc aac tgc cgt    98
Ala Glu Thr Ile Leu Ile Glu Thr Lys Thr Ala Gly Gly Asn Cys Arg
            15                  20                  25 tca tat ctg atg gcg ggc gct agc tat ctg ggc atc ctc tgc ttc gtc    146
Ser Tyr Leu Met Ala Gly Ala Ser Tyr Leu Gly Ile Leu Cys Phe Val
        30                  35                  40 ccg ctg ctt atg agc cgc gat gac gaa tat gtg tac ttc cat gcc aag    194
Pro Leu Leu Met Ser Arg Asp Asp Glu Tyr Val Tyr Phe His Ala Lys
    45                  50                  55 cag ggg ctg gtg ctg tgg atg tgg agc atc ctg gcc atg ttc gcg ctg    242
Gln Gly Leu Val Leu Trp Met Trp Ser Ile Leu Ala Met Phe Ala Leu
60                  65                  70                  75 cat ctg ccg ggc atc ggc aag tgg ctc ttc ggc ttc tcg tcc atg ggc    290
His Leu Pro Gly Ile Gly Lys Trp Leu Phe Gly Phe Ser Ser Met Gly
                80                  85                  90 gtc ctg atg ctg tcc gtg gtc ggc ttg gtc tcg gtg gcg ctg cgc cgc    338
Val Leu Met Leu Ser Val Val Gly Leu Val Ser Val Ala Leu Arg Arg
            95                  100                 105 acc tgg cgt ctg ccc ctt ata agc cat gta gtc gcc ctg atc tga        383
Thr Trp Arg Leu Pro Leu Ile Ser His Val Val Ala Leu Ile
        110                 115                 120 cggcgagcga tctaacggac ccggacagca gcgcaagcac gcgaccggag tcctttgctt    443
tggagtccca agcggcttct gccatgtagg cgcagtttcg tctcaggaaa ggccaatacc    503
```

```
atg cag gac ctt ttt ctc gcg cca cca ccc tga tggccacggg cgccagtacg      556
Met Gln Asp Leu Phe Leu Ala Pro Pro Pro
    125                 130 atcaccccg tcactgccgc cgccgctggc agcgccatgc tgacagccaa aggtgttggc       616
ctcgggcttg gcctgggcct cggcgcctgg gggccgttcg ccctaggggc tatcggccta     676
gcgggtgttg tcgcgcttta tacctgggcg cgccgccgcc atggcgctcc cgatgtttcc     736
gatgatgcat tgctggcggc tgtcggcgag gaataagcct gacccttgaa ttcaggacaa     796 cagcg atg agc ttt caa ctt gcg ccg tac ttg gcg aaa tcc gtc cct gga      846
      Met Ser Phe Gln Leu Ala Pro Tyr Leu Ala Lys Ser Val Pro Gly
          135                 140                 145 atc ggc att ctc ggc ggc att gtc ggt ggc gcc gcc gcc ctt gcc aag        894
Ile Gly Ile Leu Gly Gly Ile Val Gly Gly Ala Ala Ala Leu Ala Lys
                150                 155                 160 aat gcc cgc ctt ttg aag gac aag cag ata acc ggc aca gaa gcg gcc        942
Asn Ala Arg Leu Leu Lys Asp Lys Gln Ile Thr Gly Thr Glu Ala Ala
        165                 170                 175 atc gac acc ggc aag gaa gcc gcc ggt gcc ggg ctt gcc acc gct ttc        990
Ile Asp Thr Gly Lys Glu Ala Ala Gly Ala Gly Leu Ala Thr Ala Phe
    180                 185                 190 tcc gcc gtc gcc gcc acc gcc gtc ggc ggt ggg ttg gtg gtc tcg ttg       1038
Ser Ala Val Ala Ala Thr Ala Val Gly Gly Gly Leu Val Val Ser Leu
195                 200                 205                 210 gga acc gcc cta atc gcc ggt gtc gcc gcc aaa tac gcc tgg gac ctg       1086
Gly Thr Ala Leu Ile Ala Gly Val Ala Ala Lys Tyr Ala Trp Asp Leu
                215                 220                 225 ggt gtc gat ttc atc gag aag gaa ttg cgt cac ggc aag tcc gcc gag       1134
Gly Val Asp Phe Ile Glu Lys Glu Leu Arg His Gly Lys Ser Ala Glu
        230                 235                 240 gcg aca gcg tcc gac gaa gac att ctg agg gaa gaa ttg gcc tga           1179
Ala Thr Ala Ser Asp Glu Asp Ile Leu Arg Glu Glu Leu Ala
    245                 250                 255

<210> SEQ ID NO 11
<211> LENGTH: 675
<212> TYPE: DNA
<213> ORGANISM: Artificial sequence
<220> FEATURE:
<223> OTHER INFORMATION: Fragment of the mamGFDC operon of M.
      gryphiswaldense ((delta)mamGFD)
<220> FEATURE:
<221> NAME/KEY: CDS
<222> LOCATION: (298)..(675)
<223> OTHER INFORMATION: Coding sequence of the mamC gene of M.
      gryphiswaldense

<400> SEQUENCE: 11
atgatcaagg gcatcgcccg ccaccaccct gatggccacg ggcgccagta cgatcacccc       60
cgtcactgcc gccgccgctg gcagcgccat gctgacagcc aaaggtgttg gcctcgggct      120
tggcctgggc ctcggcgcct gggggccgtt cgccctaggg gctatcggcc tagcgggtgt      180
tgtcgcgctt tatacctggg cgcgccgccg ccatggcgct cccgatgttt ccgatgatgc      240
attgctggcg gctgtcggcg aggaataagc ctgacccttg aattcaggac aacagcg        297 atg agc ttt caa ctt gcg ccg tac ttg gcg aaa tcc gtc cct gga atc        345
Met Ser Phe Gln Leu Ala Pro Tyr Leu Ala Lys Ser Val Pro Gly Ile
1               5                   10                  15 ggc att ctc ggc ggc att gtc ggt ggc gcc gcc gcc ctt gcc aag aat        393
Gly Ile Leu Gly Gly Ile Val Gly Gly Ala Ala Ala Leu Ala Lys Asn
            20                  25                  30
```

```
gcc cgc ctt ttg aag gac aag cag ata acc ggc aca gaa gcg gcc atc      441
Ala Arg Leu Leu Lys Asp Lys Gln Ile Thr Gly Thr Glu Ala Ala Ile
        35                  40                  45 gac acc ggc aag gaa gcc gcc ggt gcc ggg ctt gcc acc gct ttc tcc      489
Asp Thr Gly Lys Glu Ala Ala Gly Ala Gly Leu Ala Thr Ala Phe Ser
 50                  55                  60 gcc gtc gcc gcc acc gcc gtc ggc ggt ggg ttg gtg gtc tcg ttg gga      537
Ala Val Ala Ala Thr Ala Val Gly Gly Gly Leu Val Val Ser Leu Gly
 65                  70                  75                  80 acc gcc cta atc gcc ggt gtc gcc gcc aaa tac gcc tgg gac ctg ggt      585
Thr Ala Leu Ile Ala Gly Val Ala Ala Lys Tyr Ala Trp Asp Leu Gly
                 85                  90                  95 gtc gat ttc atc gag aag gaa ttg cgt cac ggc aag tcc gcc gag gcg      633
Val Asp Phe Ile Glu Lys Glu Leu Arg His Gly Lys Ser Ala Glu Ala
            100                 105                 110 aca gcg tcc gac gaa gac att ctg agg gaa gaa ttg gcc tga              675
Thr Ala Ser Asp Glu Asp Ile Leu Arg Glu Glu Leu Ala
        115                 120                 125

<210> SEQ ID NO 12
<211> LENGTH: 1109
<212> TYPE: DNA
<213> ORGANISM: Artificial sequence
<220> FEATURE:
<223> OTHER INFORMATION: Fragment of the mamGFDC operon of M.
      gryphiswaldense ((delta)mamGFC)
<220> FEATURE:
<221> NAME/KEY: CDS
<222> LOCATION: (1)..(21)
<223> OTHER INFORMATION: Remnant coding sequence of the mamG gene of M.
      gryphiswaldense
<220> FEATURE:
<221> NAME/KEY: CDS
<222> LOCATION: (165)..(1109)
<223> OTHER INFORMATION: Coding sequence of the mamD gene fo M.
      gryphiswaldense

<400> SEQUENCE: 12 atg atc aag ggc atc gcc taa gccatgtagt cgccctgatc tgacggcgag          51
Met Ile Lys Gly Ile Ala
 1               5 cgatctaacg gacccggaca gcagcgcaag cacgcgaccg gagtcctttg ctttggagtc    111
ccaagcggct tctgccatgt aggcgcagtt tcgtctcagg aaaggccaat acc atg      167
                                                            Met cag gac ctt ttt ctc gcg aag gtc gaa agc gcc atg cag gcg tcc cag      215
Gln Asp Leu Phe Leu Ala Lys Val Glu Ser Ala Met Gln Ala Ser Gln
         10                  15                  20 gtc ggg gca ctt gcc ggt cag acg gcg acg gtc tcg tca gtc tcg gcc      263
Val Gly Ala Leu Ala Gly Gln Thr Ala Thr Val Ser Ser Val Ser Ala
 25                  30                  35 acg acc aat ctg gcc acc ata acc cca acc acc gcc ggg cag gcc cct      311
Thr Thr Asn Leu Ala Thr Ile Thr Pro Thr Thr Ala Gly Gln Ala Pro
 40                  45                  50                  55 atc atc gtc aaa ctg gac gcg gca cgg cag gtg acg gag ttg cag gcc      359
Ile Ile Val Lys Leu Asp Ala Ala Arg Gln Val Thr Glu Leu Gln Ala
             60                  65                  70 ctg atg gga aag acc gtg ctg gtc gga aag acc ccg acc acc atc ggc      407
Leu Met Gly Lys Thr Val Leu Val Gly Lys Thr Pro Thr Thr Ile Gly
         75                  80                  85 ggc atc gga aac tgg att gcc ttg acc ccg gcg gcg gga gcc aag acc      455
Gly Ile Gly Asn Trp Ile Ala Leu Thr Pro Ala Ala Gly Ala Lys Thr
     90                  95                 100
```

```
ggc gct gcc gtg gcc gga acc ggt cag ctt gtc atg atg aag gtc gag      503
Gly Ala Ala Val Ala Gly Thr Gly Gln Leu Val Met Met Lys Val Glu
        105                 110                 115 ggc acc ggc gcg gcc atc aag ctt ccc gcc ctg gcg ggt aag agc ttc      551
Gly Thr Gly Ala Ala Ile Lys Leu Pro Ala Leu Ala Gly Lys Ser Phe
120                 125                 130                 135 atc gtc gcc cag ccc ccc gta gcc gcc gga acc aaa gcg gcg ggc atg      599
Ile Val Ala Gln Pro Pro Val Ala Ala Gly Thr Lys Ala Ala Gly Met
            140                 145                 150 ctc tat ctg aat ccg gtt ggc ggt ggt gat atg gtg gcc atc aac att      647
Leu Tyr Leu Asn Pro Val Gly Gly Gly Asp Met Val Ala Ile Asn Ile
                155                 160                 165 cag aac gcc atg acc cag acc ggc ggc ttg gtc ggc aag acc ttc acc      695
Gln Asn Ala Met Thr Gln Thr Gly Gly Leu Val Gly Lys Thr Phe Thr
    170                 175                 180 gtc gcc ccc agc ccc gtc att ggc ggc acc acc ggt aaa ttc ctg gtc      743
Val Ala Pro Ser Pro Val Ile Gly Gly Thr Thr Gly Lys Phe Leu Val
185                 190                 195 ctg aag ccc atg gcg acc ggg gtc ggc aag gcg gtg ggc agc ggc gcc      791
Leu Lys Pro Met Ala Thr Gly Val Gly Lys Ala Val Gly Ser Gly Ala
200                 205                 210                 215 gtc gtc gcc aag ttc gta ccc gcc gcc gtc acc ggc acg ggc gga gcg      839
Val Val Ala Lys Phe Val Pro Ala Ala Val Thr Gly Thr Gly Gly Ala
            220                 225                 230 gcg gct atc ggg gcc gga tcc gcc acc acc ctg atg gcc acg ggc gcc      887
Ala Ala Ile Gly Ala Gly Ser Ala Thr Thr Leu Met Ala Thr Gly Ala
                235                 240                 245 agt acg atc acc ccc gtc act gcc gcc gcc gct ggc agc gcc atg ctg      935
Ser Thr Ile Thr Pro Val Thr Ala Ala Ala Ala Gly Ser Ala Met Leu
    250                 255                 260 aca gcc aaa ggt gtt ggc ctc ggg ctt ggc ctg ggc ctc ggc gcc tgg      983
Thr Ala Lys Gly Val Gly Leu Gly Leu Gly Leu Gly Leu Gly Ala Trp
265                 270                 275 ggg ccg ttc gcc cta ggg gct atc ggc cta gcg ggt gtt gtc gcg ctt     1031
Gly Pro Phe Ala Leu Gly Ala Ile Gly Leu Ala Gly Val Val Ala Leu
280                 285                 290                 295 tat acc tgg gcg cgc cgc cgc cat ggc gct ccc gat gtt tcc gat gat     1079
Tyr Thr Trp Ala Arg Arg Arg His Gly Ala Pro Asp Val Ser Asp Asp
            300                 305                 310 gca ttg ctg gcg gct gtc ggc gag gaa taa                             1109
Ala Leu Leu Ala Ala Val Gly Glu Glu
                315                 320

<210> SEQ ID NO 13
<211> LENGTH: 255
<212> TYPE: DNA
<213> ORGANISM: Artificial sequence
<220> FEATURE:
<223> OTHER INFORMATION: Fragment of the mamGFDC operon of M.
      gryphiswaldense ((delta)mamFDC)
<220> FEATURE:
<221> NAME/KEY: CDS
<222> LOCATION: (1)..(255)
<223> OTHER INFORMATION: Coding sequence of the mamG gene fo M.
      gryphiswaldense

<400> SEQUENCE: 13 atg atc aag ggc atc gcc ggc gtt ggc gga acc gcc ctt ggc gtc ggt       48
Met Ile Lys Gly Ile Ala Gly Val Gly Gly Thr Ala Leu Gly Val Gly
1               5                   10                  15 ggc gga gtt gcc gcc cct ccg gtc tct gcc gct gct gtc ggc agc acc       96
Gly Gly Val Ala Ala Pro Pro Val Ser Ala Ala Ala Val Gly Ser Thr
            20                  25                  30
```

```
                                                     -continued
ttg ctg gcc ggc aag ggg gtg tgc ctg ggg ctg ggg ctt ggc ctc ggt        144
Leu Leu Ala Gly Lys Gly Val Cys Leu Gly Leu Gly Leu Gly Leu Gly
        35                  40                  45 gct tgg ggt ccc gtt ctt ctc ggc gtt gcc gga ttg gct tgc gcc gcc        192
Ala Trp Gly Pro Val Leu Leu Gly Val Ala Gly Leu Ala Cys Ala Ala
50                  55                  60 tcc cta tgt gat tat ctg aag aat cgc aaa gcg cag gct gag gcc agc        240
Ser Leu Cys Asp Tyr Leu Lys Asn Arg Lys Ala Gln Ala Glu Ala Ser
65                  70                  75                  80 gct gag cct gct taa                                                    255
Ala Glu Pro Ala <210> SEQ ID NO 14
<211> LENGTH: 383
<212> TYPE: DNA
<213> ORGANISM: Artificial sequence
<220> FEATURE:
<223> OTHER INFORMATION: Fragment of the mamGFDC operon of M.
      gryphiswaldense ((delta)mamGDC)
<220> FEATURE:
<221> NAME/KEY: CDS
<222> LOCATION: (1)..(33)
<223> OTHER INFORMATION: Remnant of coding sequence of the mamG gene of
      M. gryphiswaldense
<220> FEATURE:
<221> NAME/KEY: CDS
<222> LOCATION: (48)..(383)
<223> OTHER INFORMATION: Coding sequence of the mamF gene of M.
      gryphiswaldense

<400> SEQUENCE: 14 atg atc aag ggc atc gcc gct gag cct gct taa gcgagggcaa agca atg        50
Met Ile Lys Gly Ile Ala Ala Glu Pro Ala                      Met
1               5                   10 gcc gag act att ttg atc gaa act aaa aca gct ggc ggc aac tgc cgt        98
Ala Glu Thr Ile Leu Ile Glu Thr Lys Thr Ala Gly Gly Asn Cys Arg
            15                  20                  25 tca tat ctg atg gcg ggc gct agc tat ctg ggc atc ctc tgc ttc gtc        146
Ser Tyr Leu Met Ala Gly Ala Ser Tyr Leu Gly Ile Leu Cys Phe Val
        30                  35                  40 ccg ctg ctt atg agc cgc gat gac gaa tat gtg tac ttc cat gcc aag        194
Pro Leu Leu Met Ser Arg Asp Asp Glu Tyr Val Tyr Phe His Ala Lys
    45                  50                  55 cag ggg ctg gtg ctg tgg atg tgg agc atc ctg gcc atg ttc gcg ctg        242
Gln Gly Leu Val Leu Trp Met Trp Ser Ile Leu Ala Met Phe Ala Leu
60                  65                  70                  75 cat ctg ccg ggc atc ggc aag tgg ctc ttc ggc ttc tcg tcc atg ggc        290
His Leu Pro Gly Ile Gly Lys Trp Leu Phe Gly Phe Ser Ser Met Gly
                80                  85                  90 gtc ctg atg ctg tcc gtg gtc ggc ttg gtc tcg gtg gcg ctg cgc cgc        338
Val Leu Met Leu Ser Val Val Gly Leu Val Ser Val Ala Leu Arg Arg
            95                  100                 105 acc tgg cgt ctg ccc ctt ata agc cat gta gtc gcc ctg atc tga           383
Thr Trp Arg Leu Pro Leu Ile Ser His Val Val Ala Leu Ile
        110                 115                 120
```